US012030896B2

(12) United States Patent
Bram et al.

(10) Patent No.: US 12,030,896 B2
(45) Date of Patent: Jul. 9, 2024

(54) PIKFYVE INHIBITORS

(71) Applicants: Mayo Foundation for Medical Education and Research, Rochester, MN (US); Sanford Burnham Prebys Medical Discovery Institute, La Jolla, CA (US)

(72) Inventors: Richard J. Bram, Rochester, MN (US); Anthony B. Pinkerton, Rancho Santa Fe, CA (US); Eduard Serguienko, San Diego, CA (US)

(73) Assignees: Mayo Foundation for Medical Education and Research, Rochester, MN (US); Sanford Burnham Prebys Medical Discovery Institute, La Jolla, CA (US)

( * ) Notice: Subject to any disclaimer, the term of this patent is extended or adjusted under 35 U.S.C. 154(b) by 646 days.

(21) Appl. No.: 17/255,810

(22) PCT Filed: Jul. 1, 2019

(86) PCT No.: PCT/US2019/040080
§ 371 (c)(1),
(2) Date: Dec. 23, 2020

(87) PCT Pub. No.: WO2020/009971
PCT Pub. Date: Jan. 9, 2020

(65) Prior Publication Data
US 2021/0139505 A1 May 13, 2021

Related U.S. Application Data

(60) Provisional application No. 62/694,296, filed on Jul. 5, 2018.

(51) Int. Cl.
| | | |
|---|---|---|
| *C07D 498/08* | (2006.01) | |
| *A61P 35/00* | (2006.01) | |
| *C07D 251/66* | (2006.01) | |
| *C07D 401/12* | (2006.01) | |
| *C07D 401/14* | (2006.01) | |
| *C07D 403/12* | (2006.01) | |
| *C07D 403/14* | (2006.01) | |
| *C07D 405/12* | (2006.01) | |
| *C07D 409/12* | (2006.01) | |
| *C07D 413/14* | (2006.01) | |
| *C07D 487/04* | (2006.01) | |
| *C07D 495/04* | (2006.01) | |

(52) U.S. Cl.
CPC ............ *C07D 498/08* (2013.01); *A61P 35/00* (2018.01); *C07D 251/66* (2013.01); *C07D 401/12* (2013.01); *C07D 401/14* (2013.01); *C07D 403/12* (2013.01); *C07D 403/14* (2013.01); *C07D 405/12* (2013.01); *C07D 409/12* (2013.01); *C07D 413/14* (2013.01); *C07D 487/04* (2013.01); *C07D 495/04* (2013.01)

(58) Field of Classification Search
CPC .. C07D 498/08; C07D 251/66; C07D 401/12; C07D 401/14; C07D 403/12; C07D 403/14; C07D 405/12; C07D 409/12; C07D 413/14; C07D 487/04; C07D 495/04; A61P 35/00
USPC .................................................... 514/210.21
See application file for complete search history.

(56) References Cited

U.S. PATENT DOCUMENTS

| | | | |
|---|---|---|---|
| 5,304,121 | A | 4/1994 | Sahatjian |
| 5,886,026 | A | 3/1999 | Hunter et al. |
| 6,099,562 | A | 8/2000 | Ding et al. |
| 6,803,031 | B2 | 10/2004 | Rabinowitz et al. |
| 2008/0058297 | A1 | 3/2008 | Ono et al. |

(Continued)

FOREIGN PATENT DOCUMENTS

| | | |
|---|---|---|
| WO | WO 2006/128129 | 11/2006 |
| WO | WO 2008/132502 | 11/2008 |

(Continued)

OTHER PUBLICATIONS

Cai et al., "PIKfyve, a Class III PI Kinase, Is the Target of the Small Molecular IL-12/IL-23 Inhibitor Apilimod and a Player in Toll-like Receptor Signaling," Chem. Biology, Jul. 25, 2013, 20(7):912-921.

(Continued)

*Primary Examiner* — Kristin A Vajda
(74) *Attorney, Agent, or Firm* — Fish & Richardson P.C.

(57) ABSTRACT

The present application provides, inter alia, a compound of Formula (I):

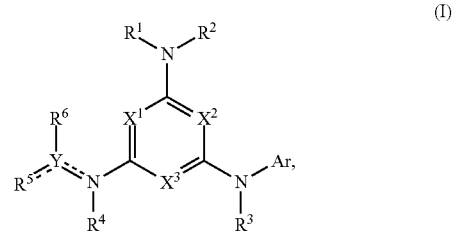

or a pharmaceutically acceptable salt thereof, wherein Y, Ar, $X^1$, $X^2$, $X^3$, $R^1$, $R^2$, $R^3$, $R^4$, $R^5$, and $R^6$ are as described herein. Methods of making these compounds and methods of using these compound for treating diseases such as cancer are also provided.

18 Claims, 22 Drawing Sheets

(56) References Cited

U.S. PATENT DOCUMENTS

2009/0163545 A1　6/2009　Goldfarb
2018/0050041 A1　2/2018　Conrad et al.

FOREIGN PATENT DOCUMENTS

| WO | WO 2009/091388 | 7/2009 | |
|---|---|---|---|
| WO | WO 2017/040971 | 3/2017 | |
| WO | WO-2017106367 A1 * | 6/2017 | ........... A61K 31/496 |
| WO | WO 2019/046316 | 3/2019 | |

OTHER PUBLICATIONS

Choi, "Cyclophilin B Supports Myc and Mutant p53-Dependent Survival of Glioblastoma Multiforme Cells," Cancer Research, Jan. 2014, 74(2):484-496.

Ekins et al., "Bayesian Models Leveraging Bioactivity and Cytotoxicity Information for Drug Discovery," Chem. Biology, Mar. 21, 2013, 20(3):370-378.

EP Extended Search Report in in European Appln. No. 19830599.7, dated Jun. 24, 2021, 7 pages.

Fabian et al., "A small molecule-kinase interaction map for clinical kinase inhibitors," Nat. Biotechnology, Feb. 13, 2005, 23(3):329-336.

Gayle et al., "Identification of apilimod as a first-in-class PIKfyve kinase inhibitor for treatment of B-cell non-Hodgkin lymphoma," Blood, Jan. 19, 2017, 129(13):1768-1778.

Guan et al., "Discovery of novel Jak2-Stat pathway inhibitors with extended residence time on target," Bioorg. Med. Chem. Letters, Mar. 7, 2013, 23(10):3105-3110.

Ilium, "Transport of drugs from the nasal cavity to the central nervous system," Eur. J. Pharm. Sciences, Jul. 2000, 11(1):1-18.

Ilium, "Is nose-to-brain transport of drugs in man a reality?," J. Pharm, Pharmacology, Jan. 2004, 56(1):3-17.

Karaman et al., "A quantitative analysis of kinase inhibitor selectivity," Nat. Biotechnology, Jan. 2008, 26(1):127-132.

Maltese et al., "Methuosis: Nonapoptotic Cell Death Associated with Vacuolization of Macropinosome and Endosome Compartments," Am. J. Pathology, Apr. 13, 2014, 184(6):1630-1642.

PCT International Preliminary Report on Patentability in International Appln. No. PCT/US2019/040080, dated Jan. 5, 2021, 7 pages.

PCT International Search Report and Written Opinion in International Appln. No. PCT/US2019/040080, dated Nov. 1, 2019, 10 pages.

Sharma et al., "A family of PIKFYVE inhibitors with therapeutic potential against autophagy-dependent cancer cells disrupt multiple events in lysosome homeostasis," Autophagy, Mar. 8, 2019, 15(10):1694-1718.

Shubin et al., "Cytoplasmic vacuolization in cell death and survival," Oncotarget, Jun. 17, 2016, 7(34):55863-55889.

Wada et al., "Apilimod Inhibits the Production of IL-12 and IL-23 and Reduces Dendritic Cell Infiltration in Psoriasis," PLoS One, Apr. 6, 2012, 7(4):e35069, 10 pages.

Wang et al., "Cycloheximide promotes paraptosis induced by inhibition of cyclophilins in glioblastoma multiforme," Cell Death and Disease, May 18, 2017, 8:e2807, 11 pages.

PubChem [online], "1H-indole-3-carbaldehyde {4-[(4-methylphenyl)amino]-6- morpholin-4-yl-1,3,5-triazin-2-yl}hydrazone," PubChem SID 17510082, created Feb. 6, 2007, last updated Mar. 1, 2012, retrieved on Feb. 22, 2024, retrieved from URL< https://pubchem.ncbi.nlm.nih.gov/substance/17510082>, 6 pages.

* cited by examiner

Name: EM2016-02380_0001
Specimen: E2409 Control
Sample ID: Block #1
Indicated Magnification: 12kx 1μm
Accelerating Voltage: 80kV
Acquisition date: 4/8/2016
Operator: ScottG Name: EM2016-02381_0002
Specimen: E2409 042
Sample ID: Block #1
Indicated Magnification: 12kx 1μm
Accelerating Voltage: 80kV
Acquisition date: 4/8/2016
Operator: ScottG

| Log-rank (Mantel-Cox) Test | |
|---|---|
| Chi square | 6.146 |
| df | 1 |
| P value | 0.0132 |
| P value summary | * |
| Are the survival curves sig different? | Yes |

PIKFYVE INHIBITORS

CROSS-REFERENCE TO RELATED APPLICATIONS

This application is a National Stage application under 35 U.S.C. § 371 of International Application No. PCT/US2019/040080, having an International Filing Date of Jul. 1, 2019 which claims priority to U.S. Application Ser. No. 62/694,296, filed on Jul. 5, 2018. The disclosure of the prior application is considered part of the disclosure of this application, and is incorporated in its entirety into this application.

STATEMENT AS TO FEDERALLY SPONSORED RESEARCH

This invention was made with government support under NS083937 awarded by the National Institutes of Health. The government has certain rights in the invention.

TECHNICAL FIELD

This invention relates to chemical compounds, in particular to compounds capable of inhibiting PIKfyve kinase and useful in treating cancer such as lymphoblastic leukemia, lymphoma, colorectal cancer, medulloblastoma, osteosarcoma, pancreatic cancer, or glioblastoma multiforme (GBM).

BACKGROUND

Phosphorylated derivatives of phosphatidylinositol (PI) regulate cytoskeletal functions, membrane trafficking, and receptor signaling by recruiting protein complexes to cell- and endosomal-membranes. Humans have multiple phosphatidylinositol proteins that differ by the degree and position of phosphorylation of the inositol ring. PIKfyve (also known as phosphatidylinositol-3-phosphate 5-kinase type III or PIPKIII) is an enzyme that phosphorylates phosphatidylinositol 3-phosphate (P3P) to produce phosphatidylinositol 3,5-bisphosphate (PI(3,5)P$_2$). PIKfyve activity is responsible for the production of both PI(3,5)P$_2$ and phosphatidylinositol 5-phosphate (PI5P) (See FIG. 1), which regulate cellular endosomal operations (fission and fusion) that maintain endomembrane homeostasis and proper performance of the trafficking pathways. PIKfyve is a large protein, containing a number of functional domains and expressed in several spliced forms. The reported full-length mouse and human cDNA clones encode proteins of 2052 and 2098 amino acid residues, respectively. By directly binding membrane PI3P, the FYVE finger domain of PIKfyve is essential in localizing the protein to the cytosolic leaflet of endosomes. Impaired PIKfyve enzymatic activity causes endosome enlargement and cytoplasmic vacuolation due to impaired PI(3,5)P$_2$ synthesis.

SUMMARY

In a first general aspect, the present application provides a compound of Formula (I):

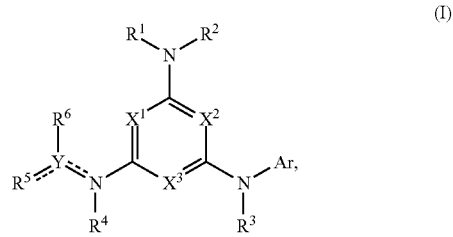

or a pharmaceutically acceptable salt thereof, wherein Y, Ar, $X^1$, $X^2$, $X^3$, $R^1$, $R^2$, $R^3$, $R^4$, $R^5$, and $R^6$ are as described herein.

In a second general aspect, the present application provides a pharmaceutical composition comprising a compound of Formula (I), or a pharmaceutically acceptable salt thereof, and a pharmaceutically acceptable carrier.

In a third general aspect, the present disclosure provides a method of inhibiting phosphatidylinositol-3-phosphate 5-kinase type III (PIKfyve) in a cancer cell, the method comprising contacting the cell with an effective amount of a compound of Formula (I), or a pharmaceutically acceptable salt thereof.

In a fourth general aspect, the present application provides a method of inducing cytoplasmic vacuolization in a cancer cell, the method comprising contacting the cell with an effective amount of a compound of Formula (I), or a pharmaceutically acceptable salt thereof.

In a fifth general aspect, the present application provides a method of inhibiting phosphatidylinositol-3-phosphate 5-kinase type III (PIKfyve) a subject, the method comprising administering to the subject in need thereof a therapeutically effective amount of a compound of Formula (I), or a pharmaceutically acceptable salt thereof, or a pharmaceutical composition comprising the compound of Formula (I), or a pharmaceutically acceptable salt thereof.

In a sixth general aspect, the present application provides a method of inducing cytoplasmic vacuolization in a cancer cell of a subject, the method comprising administering to the subject in need thereof a therapeutically effective amount of a compound of Formula (I), or a pharmaceutically acceptable salt thereof, or a pharmaceutical composition comprising the compound of Formula (I), or a pharmaceutically acceptable salt thereof.

In a seventh general aspect, the present application provides a method of treating a cancer in a subject the method comprising administering to a subject in need thereof a therapeutically effective amount of a compound of Formula (I), or a pharmaceutically acceptable salt thereof, or a pharmaceutical composition comprising the compound of Formula (I), or a pharmaceutically acceptable salt thereof.

In an eighth general aspect, the present application provides a method of treating cancer in a subject, the method comprising administering to the subject in need thereof a therapeutically effective amount of a compound of Formula (I), or a pharmaceutically acceptable salt thereof, in combination with a BRAF-V600E inhibitor (e.g., vemurafenib), or a pharmaceutically acceptable salt thereof.

In a ninth general aspect, the present application provides a method of blocking secretion of IL12/23 in a cell, the method comprising contacting the cell with an effective amount of a compound of Formula (I), or a pharmaceutically acceptable salt thereof.

In a tenth general aspect, the present application provides a method of blocking secretion of IL12/23 in a subject, the method comprising administering to the subject a therapeutically effective amount of a compound of Formula (I), or a pharmaceutically acceptable salt thereof, or a pharmaceutical composition comprising the compound of Formula (I), or a pharmaceutically acceptable salt thereof.

In a eleventh general aspect, the present application provides a method of treating an inflammatory disease or condition in a subject, the method comprising administering to the subject a therapeutically effective amount of a compound of Formula (I), or a pharmaceutically acceptable salt thereof, or a pharmaceutical composition comprising the compound of Formula (I), or a pharmaceutically acceptable salt thereof.

Certain implementations of these general aspects are described herein.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DETAILED DESCRIPTION

Figure 1:
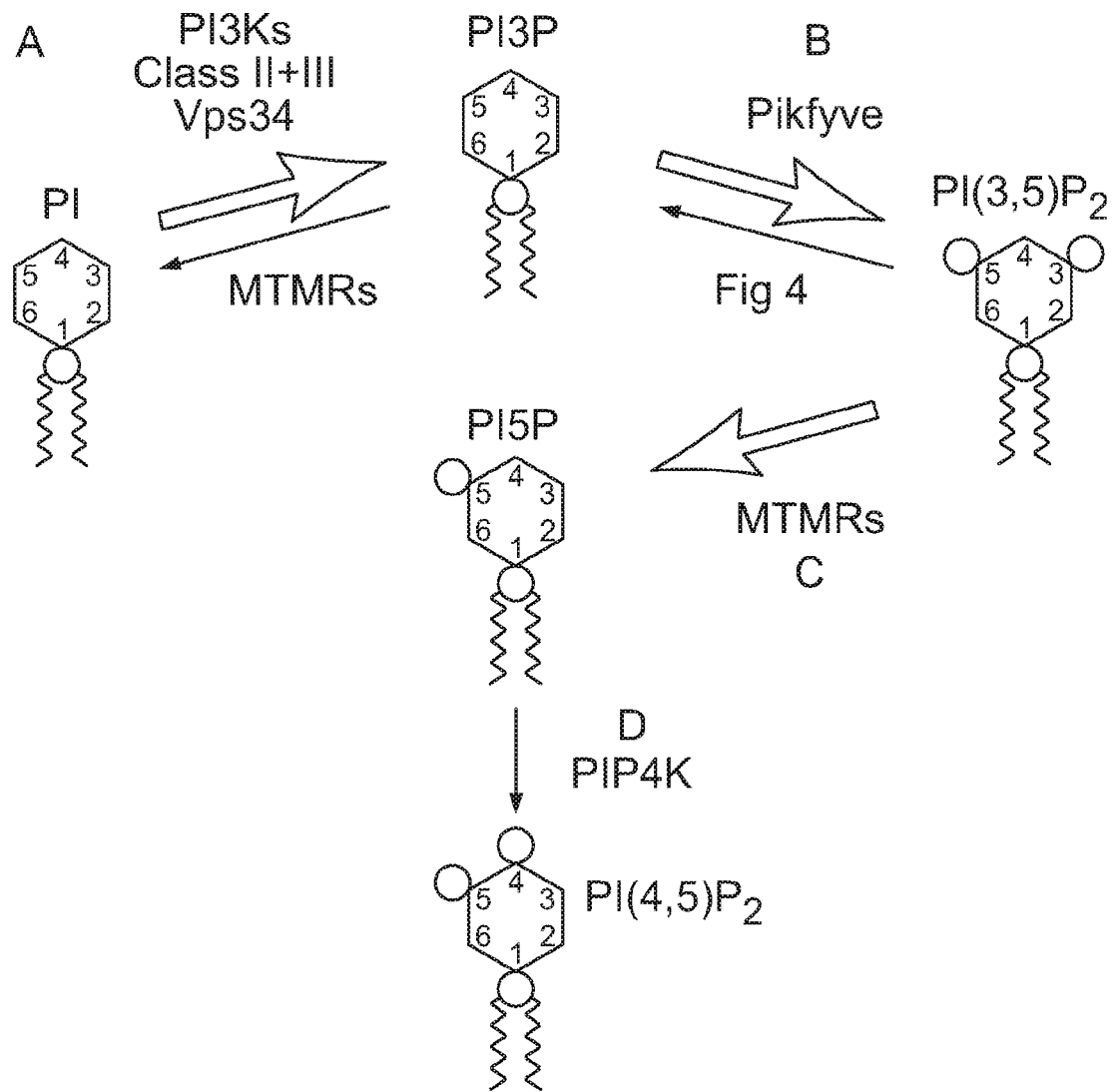
FIG. 1. is a scheme showing PIKfyve enzymatic processes.

PIKfyve is a lipid kinase, that catalyzes the addition of a phosphate to the 5 position of phosphatidyl inositol (PI) or to phosphatidyl-3-phosphate (PI3P), to produce PI5P and $PI(3,5)P_2$, respectively. These minor lipids are important for vesicle trafficking within the cell, during import of nutrients and other molecules by macropinocytosis, and also for proper functioning of lysosomes and autophagy. Knockdown or mutation of PIKfyve was previously shown to cause massive cytosolic vacuolization. The present application provides therapeutic compounds that are capable of inhibiting PIKfyve and inducing cellular vacuolization, and are useful in treating cancer. Pharmaceutical compositions and methods of making the compounds are also provided.

Therapeutic Compounds

In one general aspect, the present application provides a compound of Formula (I):

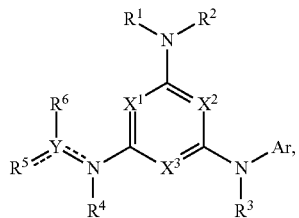

or a pharmaceutically acceptable salt thereof, wherein:

each bond denoted as ⌇ is either a single bond or a double bond, provided that the two bonds denoted as ⌇ are not both simultaneously double bonds;

$X^1$ is selected from N and $CR^A$;

$X^2$ is selected from N and $CR^A$;

$X^3$ is selected from N and $CR^A$;

each $R^A$ is independently selected from H, halo, $C_{1-6}$ alkyl, $C_{1-6}$ haloalkyl, $C_{1-6}$ alkoxy, and $C_{1-6}$ haloalkoxy;

Ar is selected from $C_{6-10}$ aryl and 5-10 membered heteroaryl, each of which is optionally substituted with 1, 2, 3, 4, or 5 substituents independently selected from $R^7$;

each $R^7$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$;

$R^1$ is selected from the group consisting of H and $C_{1-6}$ alkyl, wherein said $C_{1-6}$ alkyl is optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$ $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

$R^2$ is $C_{1-6}$ alkyl which is optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; or $R^1$ and $R^2$ together with the N to which they are attached form a 4-7 membered heterocycloalkyl, which is optionally substituted with 1, 2, 3, 4, or 5 substituents independently selected $R^8$;

each $R^8$ is independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$ $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

$R^3$ is selected from H, $C_{1-6}$ alkyl, and $C_{1-6}$ haloalkyl;

$R^4$ is selected from H, $C_{1-6}$ alkyl, and $C_{1-6}$ haloalkyl;

Y is selected from N, C, and $CR^A$;

when the bond between $R^5$ and Y is a single bond, $R^5$ is 5-10 membered heteroaryl, which is optionally substituted with 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$ $S(O)_2R^{b3}$, and $S(O)_2NR^{c3}R^{d3}$;

when the bond between $R^5$ and Y is a double bond, $R^5$ is $CR^BR^C$;

$R^B$ is selected from H, $C_{1-6}$ alkyl, and $C_{1-6}$ haloalkyl;

$R^C$ is selected from $C_{6-10}$ aryl and 5-10 membered heteroaryl, each of which is optionally substituted with 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$; or $R^4$ and $R^5$ together with Y and N to which $R^4$ is attached form a 5-14 membered heteroaryl, which is optionally substituted with 1, 2, 3, 4, or 5 substituents independently selected from $R^9$;

each $R^9$ is independently selected from halo, CN, $NO_2$, $C_{1-6}$ alkyl, $C_{2-6}$ alkenyl, $C_{2-6}$ alkynyl, $C_{1-6}$ haloalkyl, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$ $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$ $NR^{c3}C(O)R^{b3}$, $NR^{c3}C(O)OR^{a3}$, $NR^{c3}C(O)NR^{c3}R^{d3}$ $NR^{c3}S(O)_2R^{b3}$, $NR^{c3}S(O)_2NR^{c3}R^{d3}$, $S(O)_2R^{b3}$, and $S(O)_2NR^{c3}R^{d3}$;

$R^6$ is selected from H, $C_{1-6}$ alkyl, and $C_{1-6}$ haloalkyl; or $R^6$ is absent;

each $R^{a1}$, $R^{b1}$, $R^{a2}$, $R^{b2}$, $R^{a3}$, and $R^{b3}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are optionally substituted with 1, 2, 3, 4, or 5 substituents independently selected from $R^g$;

each $R^{c1}$, $R^{d1}$, $R^{c2}$, $R^{d2}$, $R^{c3}$, and $R^{d3}$ is independently selected from H, $C_{1-6}$ alkyl, $C_{1-4}$ haloalkyl, $C_{2-6}$ alkenyl, $C_{2-6}$ alkynyl, $C(O)R^{b7}$, $C(O)NR^{c7}R^{d7}$, $C(O)OR^{a7}$, $NR^{c7}R^{d7}$, $S(O)R^{b7}$, $S(O)NR^{c7}R^{d7}$, $S(O)_2R^{b7}$, and $S(O)_2 NR^{c7}R^{d7}$; wherein said $C_{1-6}$ alkyl, $C_{2-6}$ alkenyl, and $C_{2-6}$ alkynyl is optionally substituted with 1, 2, 3, 4, or 5 substituents independently selected from $R^g$;

each $R^{a7}$, $R^{b7}$, $R^{c7}$, and $R^{d7}$ is independently selected from H, $C_{1-6}$ alkyl, $C_{1-4}$ haloalkyl, $C_{2-6}$ alkenyl, $C_{2-6}$ alkynyl, and $R^g$, wherein said $C_{1-6}$ alkyl, $C_{2-6}$ alkenyl, and $C_{2-6}$ alkynyl is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

In some embodiments, both bonds denoted as ⁓ are single bonds.

In some embodiments, one bond denoted as ⁓ is a single bond, and the other bond denoted as ⁓ is a double bond.

In some embodiments, $X^1$ is N. In some embodiments, $X^1$ is $CR^A$. In some embodiments, $X^2$ is N. In some embodiments, $X^2$ is $CR^A$. In some embodiments, $X^3$ is N. In some embodiments, $X^3$ is $CR^A$.

In some embodiments, $R^A$ is independently selected from H, halo, $C_{1-6}$ alkyl, and $C_{1-6}$ haloalkyl. In some embodiments, $R^A$ is independently selected from H, $C_{1-6}$ alkyl, and $C_{1-6}$ haloalkyl. In some embodiments, $R^A$ is H.

In some embodiments, Ar is $C_{6-10}$ aryl, optionally substituted with 1, 2, or 3 substituents independently selected from $R^7$. In some embodiments, Ar is phenyl or naphthyl.

In some embodiments, Ar is 5-10 membered heteroaryl, optionally substituted with 1, 2, or 3 substituents independently selected from $R^7$. In some embodiments, Ar is pyridinyl (e.g., pyridin-2-yl).

In some embodiments, $R^7$ is selected from halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

In some embodiments, $R^7$ is selected from halo, CN, $NO_2$, $C_{1-6}$ alkyl, $C_{1-6}$ haloalkyl, $OR^{a1}$, $NR^{c1}R^{d1}$, $NR^{c1}C(O)R^{b1}$, and $NR^{c1}S(O)_2R^{b1}$.

In some embodiments, $R^7$ is selected from methyl, trifluoromethyl, methoxy, fluoro, chloro, bromo, CN, $NO_2$, amino, dimethylamino, $NHC(O)CH_3$, and $NHS(O)_2CH_3$.

In some embodiments, Y is N. In some aspects of these embodiments, one of the bonds denoted as ⁓ is a double bond, and $R^6$ is absent. In other aspects of these embodiments, both bonds denoted as ⁓ are single bonds and $R^6$ is present and is as described herein.

In some embodiments, one of the bonds denoted as ⁓ is a double bond, and Y is C. In other embodiments, both bonds denoted as ⁓ are single bonds and Y is $CR^A$.

In some embodiments, $R^1$ is H. In some embodiments, $R^1$ is $C_{1-6}$ alkyl optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, and $NR^{c2}R^{d2}$. In some embodiments, $R^1$ is $C_{1-6}$ alkyl optionally substituted with $OR^{a2}$.

In some embodiments, $R^2$ is H. In some embodiments, $R^2$ is $C_{1-6}$ alkyl optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, and $NR^{c2}R^{d2}$. In some embodiments, $R^2$ is $C_{1-6}$ alkyl optionally substituted with $OR^{a2}$.

In some embodiments, $R^1$ is H and $R^2$ is $C_{1-6}$ alkyl optionally substituted with $OR^{a2}$. In some embodiments, $R^1$ and $R^2$ are each independently an $C_{1-6}$ alkyl optionally substituted with $OR^{a2}$.

In some embodiments, $R^1$ and $R^2$ together form a 4-7 membered heterocycloalkyl, which is optionally substituted with 1, 2, or 3 substituents independently selected $R^8$.

In some embodiments, $R^1$ and $R^2$ together with N to which they are attached form a ring selected from morpholinyl, thiomorpholinyl, piperidinyl, pyrrolidinyl, piperazinyl, azetidinyl, and 3-oxa-8-azabicyclo[3.2.1]octanyl, each of which is optionally substituted with 1, 2, or 3 independently selected $R^8$.

In some embodiments, $R^1$ and $R^2$ together with N to which they are attached form a ring of formula:

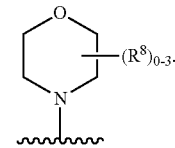

In some embodiments, $R^8$ is selected from halo, $C_{1-6}$ alkyl, $C_{1-6}$ haloalkyl, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}S(O)_2R^{b2}$, $S(O)_2R^{b2}$, and $S(O)_2NR^{c2}R^{d2}$.

In some embodiments, $R^8$ is selected from $C_{1-6}$ alkyl and $OR^{a2}$. In some embodiments, $R^8$ is selected from $C_{1-6}$ alkyl. In some embodiments, $R^8$ is OH. In some embodiments, $R^8$ is $C_{1-6}$ alkoxy.

In some embodiments, $R^3$ is selected from H and $C_{1-6}$ alkyl. In some embodiments, $R^4$ is selected from H and $C_{1-6}$ alkyl. In some embodiments, $R^3$ and $R^4$ are each H. In some embodiments, one of $R^3$ and $R^4$ is H and the other is $C_{1-6}$ alkyl.

In some embodiments, the bond between $R^5$ and Y is a single bond, $R^5$ is 5-10 membered heteroaryl, which is optionally substituted with 1, 2, or 3 substituents independently selected from halo, CN, $NO_2$, $C_{1-6}$ alkyl, $C_{1-6}$ haloalkyl, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$.

In some embodiments, the bond between $R^5$ and Y is a single bond, $R^5$ is 5-10 membered heteroaryl, which is optionally substituted with 1, 2, or 3 substituents independently selected from halo, CN, $NO_2$, $C_{1-6}$ alkyl, $C_{1-6}$ haloalkyl, $OR^{a3}$, $NR^{c3}R^{d3}$, $NR^{c3}C(O)R^{b3}$, and $NR^{c3}S(O)_2R^{b3}$.

In some embodiments, the bond between $R^5$ and Y is a double bond, $R^5$ is $CR^BR^C$.

In some embodiments, $R^B$ is selected from H and $C_{1-6}$ alkyl.

In some embodiments, $R^B$ is H.

In some embodiments, $R^C$ is a 5-10 membered heteroaryl, which is optionally substituted with 1, 2, or 3 substituents independently selected from halo, CN, $NO_2$, $C_{1-6}$ alkyl, $C_{1-6}$ haloalkyl, $OR^{a3}$, $NR^{c3}R^{d3}$, $NR^{c3}C(O)R^{b3}$, and $NR^{c3}S(O)_2R^{b3}$.

In some embodiments, $R^C$ is selected from indolyl, pyridinyl, pyrrolyl, and thiophenyl, each of which is optionally substituted with 1, 2, or 3 substituents independently selected from halo, CN, $NO_2$, $C_{1-6}$ alkyl, $C_{1-6}$ haloalkyl, $OR^{a3}$, $NR^{c3}R^{d3}$, $NR^{c3}C(O)R^{b3}$, and $NR^{c3}S(O)_2R^{b3}$. In some embodiments, $R^C$ is selected from indolyl, pyridinyl, pyrrolyl, and thiophenyl, each of which is optionally substituted with 1, 2, or 3 substituents independently selected from methyl, trifluoromethyl, methoxy, fluoro, chloro, bromo, CN, $NO_2$, amino, dimethylamino, $NHC(O)CH_3$, and $NHS(O)_2CH_3$.

In some embodiments, $R^C$ is indolyl, which is optionally substituted with 1, 2, or 3 substituents independently selected from halo, CN, $NO_2$, $C_{1-6}$ alkyl, $C_{1-6}$ haloalkyl, $OR^{a3}$, $NR^{c3}R^{d3}$, $NR^{c3}C(O)R^{b3}$, and $NR^{c3}S(O)_2R^{b3}$.

In some embodiments, $R^C$ is indolyl, which is optionally substituted with 1, 2, or 3 substituents independently selected from methyl, trifluoromethyl, methoxy, fluoro, chloro, bromo, CN, $NO_2$, amino, dimethylamino, $NHC(O)CH_3$, and $NHS(O)_2CH_3$.

In some embodiments, $R^C$ is a $C_{6-10}$ aryl, which is optionally substituted with 1, 2, or 3 substituents independently selected from halo, CN, $NO_2$, $C_{1-6}$ alkyl, $C_{1-6}$ haloalkyl, $OR^{a3}$, $NR^{c3}R^{d3}$ $NR^{c3}C(O)R^{b3}$, and $NR^{c3}S(O)_2R^{b3}$. In some embodiments, $R^C$ is a phenyl, which is optionally substituted with 1, 2, or 3 substituents independently selected from halo, CN, $NO_2$, $C_{1-6}$ alkyl, $C_{1-6}$ haloalkyl, $OR^{a3}$, $NR^{c3}R^{d3}$, $NR^{c3}C(O)R^{b3}$, and $NR^{c3}S(O)_2R^{b3}$.

In some embodiments, $R^C$ is a phenyl, which is optionally substituted with 1, 2, or 3 substituents independently selected from methyl, trifluoromethyl, methoxy, fluoro, chloro, bromo, CN, $NO_2$, amino, dimethylamino, $NHC(O)CH_3$, and $NHS(O)_2CH_3$.

In some embodiments, $R^4$ and $R^5$ together with Y and N to which $R^4$ is attached form a 5-14 membered heteroaryl, which is optionally substituted with 1, 2, or 3 substituents independently selected from $R^9$. In some embodiments, and $R^5$ together with Y and N to which $R^4$ is attached form a pyridazinyl or a pyrazolyl ring, each of which may be optionally fused with other rings, and optionally substituted with 1, 2, or 3 substituents independently selected from $R^9$.

In some embodiments, $R^9$ is selected from halo, CN, $NO_2$, $C_{1-6}$ alkyl, $C_{2-6}$ alkenyl, $C_{2-6}$ alkynyl, $C_{1-6}$ haloalkyl, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$.

In some embodiments, $R^9$ is selected from halo, CN, $NO_2$, $C_{1-6}$ alkyl, $C_{1-6}$ haloalkyl, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $S(O)_2R^{b3}$, and $S(O)_2NR^{c3}R^{d3}$.

In some embodiments, $R^9$ is selected from halo, CN, $NO_2$, $C_{1-6}$ alkyl, $C_{1-6}$ haloalkyl, $OR^{a3}$, $NR^{c3}R^{d3}$, $NR^{c3}C(O)R^{b3}$, and $NR^{c3}S(O)_2R^{b3}$.

In some embodiments, $R^{a1}$, $R^{c1}$, and $R^{d1}$ are each independently selected from H, $C_{1-6}$ alkyl, and $C_{1-4}$ haloalkyl. In some embodiments, each $R^{b1}$ is independently selected from $C_{1-6}$ alkyl and $C_{1-4}$ haloalkyl.

In some embodiments, $R^{a2}$, $R^{c2}$, and $R^{d2}$ are each independently selected from H, $C_{1-6}$ alkyl, and $C_{1-4}$ haloalkyl. In some embodiments, each $R^{b2}$ is independently selected from $C_{1-6}$ alkyl and $C_{1-4}$ haloalkyl. In some embodiments, each $R^{a2}$ is selected from H and $C_{1-6}$ alkyl.

In some embodiments, $R^{a3}$, $R^{c3}$, and $R^{d3}$ are each independently selected from H, $C_{1-6}$ alkyl, and $C_{1-4}$ haloalkyl. In some embodiments, each $R^{b3}$ is independently selected from $C_{1-6}$ alkyl and $C_{1-4}$ haloalkyl.

In some embodiments:
$R^1$, $R^3$, and $R^4$ are each H;
$R^2$ is $C_{1-6}$ alkyl optionally substituted with $OR^{a2}$;
$R^{a2}$ is selected from H and $C_{1-6}$ alkyl
the bond between $R^5$ and Y is a double bond;
Y is N;
$R^6$ is absent;
$R^5$ is $CR^BR^C$;
$R^7$ is $C_{1-6}$ alkyl;
$R^B$ is H; and
$R^C$ is indolyl.

In some embodiments:
$R^1$ and $R^2$ are each independently selected from $C_{1-6}$ alkyl optionally substituted with $OR^{a2}$;
$R^3$ and $R^4$ are each H;
$R^{a2}$ is selected from H and $C_{1-6}$ alkyl;
the bond between $R^5$ and Y is a double bond;
Y is N;
$R^6$ is absent;
$R^5$ is $CR^BR^C$;
$R^7$ is $C_{1-6}$ alkyl;
$R^B$ is H; and
$R^C$ is indolyl.

In some embodiments:
$R^1$ and $R^2$ together form a 4-7 membered heterocycloalkyl, which is optionally substituted with 1, 2, or 3 substituents independently selected R;
each $R^8$ is selected from $C_{1-6}$ alkyl and $OR^{a2}$;
$R^{a2}$ is selected from H and $C_{1-6}$ alkyl;
$R^3$ and $R^4$ are each H;
the bond between $R^5$ and Y is a double bond;
Y is N;
$R^6$ is absent;
$R^5$ is $CR^BR^C$;
each $R^7$ is selected from halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;
$R^{a1}$, $R^{c1}$, and $R^{d1}$ are each independently selected from H, $C_{1-6}$ alkyl, and $C_{1-4}$ haloalkyl;
each $R^{b1}$ is independently selected from $C_{1-6}$ alkyl and $C_{1-4}$ haloalkyl;
$R^A$ is selected from H, $C_{1-6}$ alkyl, and $C_{1-6}$ haloalkyl;
$R^B$ is H.
$R^C$ is a 5-10 membered heteroaryl, which is optionally substituted with 1, 2, or 3 substituents independently selected from halo, CN, $NO_2$, $C_{1-6}$ alkyl, $C_{1-6}$ haloalkyl, $OR^{a3}$, $NR^{c3}R^{d3}$, $NR^{c3}C(O)R^{b3}$, and $NR^{c3}S(O)_2R^{b3}$;
$R^{a3}$, $R^{c3}$, and $R^{d3}$ are each independently selected from H, $C_{1-6}$ alkyl, and $C_{1-4}$ haloalkyl; and
each $R^{b3}$ is independently selected from $C_{1-6}$ alkyl and $C_{1-4}$ haloalkyl.

In some embodiments:
$R^1$ and $R^2$ together with N to which they are attached form a ring selected from morpholinyl, thiomorpholinyl, piperidinyl, pyrrolidinyl, piperazinyl, azetidinyl, and 3-oxa-8-azabicyclo[3.2.1]octanyl, each of which is optionally substituted with 1, 2, or 3 independently selected $R^1$;
$R^8$ is selected from $C_{1-6}$ alkyl and $OR^{a2}$;
$R^{a2}$ is selected from H and $C_{1-6}$ alkyl;

$R^3$ and $R^4$ are each H;

$R^7$ is selected from halo, CN, $NO_2$, $C_{1-6}$ alkyl, $C_{1-6}$ haloalkyl, $OR^{a1}$, $NR^{c1}R^d$, $NR^{c1}C(O)R^{b1}$, and $NR^{c1}S(O)_2R^{b1}$;

$R^{a1}$, $R^{c1}$, and $R^{d1}$ are each independently selected from H, $C_{1-6}$ alkyl, and $C_{1-4}$ haloalkyl;

each $R^{b1}$ is independently selected from $C_{1-6}$ alkyl and $C_{1-4}$ haloalkyl;

the bond between $R^5$ and Y is a double bond;

Y is N;

$R^6$ is absent;

$R^5$ is $CR^BR^C$;

$R^4$ is H;

$R^B$ is H; and $R^C$ is selected from indolyl, pyridinyl, pyrrolyl, and thiophenyl, each of which is optionally substituted with 1 or 2 substituents independently selected from methyl, trifluoromethyl, methoxy, fluoro, chloro, bromo, CN, $NO_2$, amino, dimethylamino, $NHC(O)CH_3$, and $NHS(O)_2CH_3$.

In some embodiments, the compound of Formula (I) is:

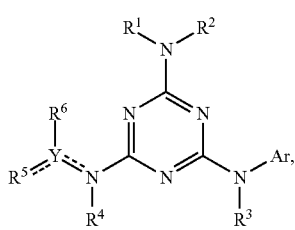

or a pharmaceutically acceptable salt thereof.

In some embodiments, the compound of Formula (I) is:

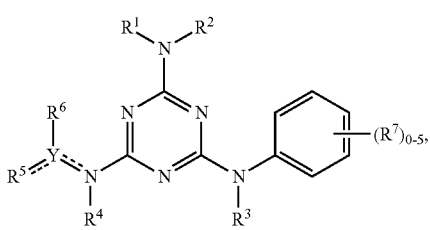

or a pharmaceutically acceptable salt thereof.

In some embodiments, the compound of Formula (I) is:

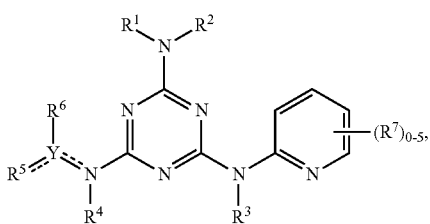

or a pharmaceutically acceptable salt thereof.

In some embodiments, the compound of Formula (I) is:

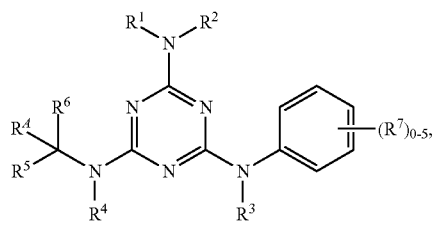

or a pharmaceutically acceptable salt thereof.

In some embodiments, the compound of Formula (I) is:

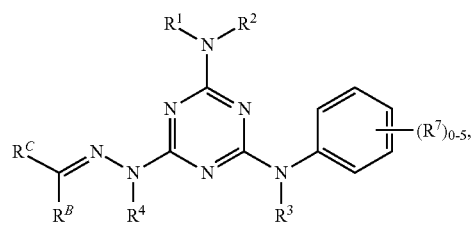

or a pharmaceutically acceptable salt thereof.

In some embodiments, the compound of Formula (I) is:

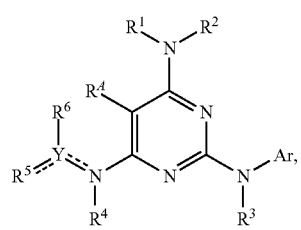

or a pharmaceutically acceptable salt thereof.

In some embodiments, the compound of Formula (I) is:

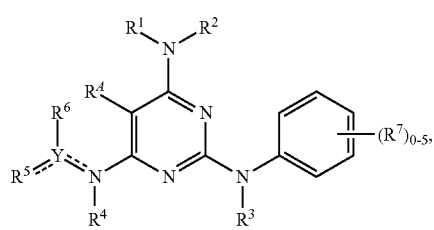

or a pharmaceutically acceptable salt thereof.

In some embodiments, the compound of Formula (I) is:

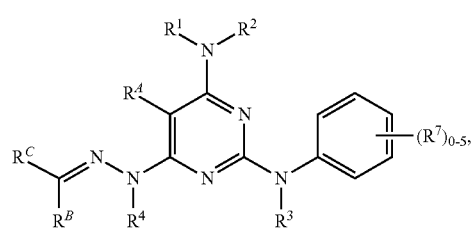

or a pharmaceutically acceptable salt thereof.

In some embodiments, the compound of Formula (I) is:

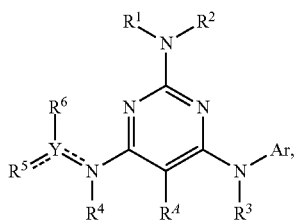

or a pharmaceutically acceptable salt thereof.
In some embodiments, the compound of Formula (I) is:

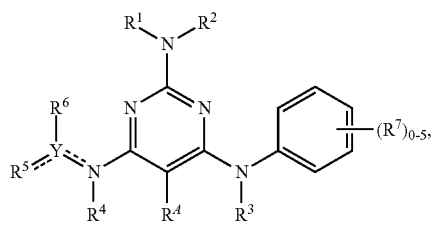

or a pharmaceutically acceptable salt thereof.
In some embodiments, the compound of Formula (I) is:

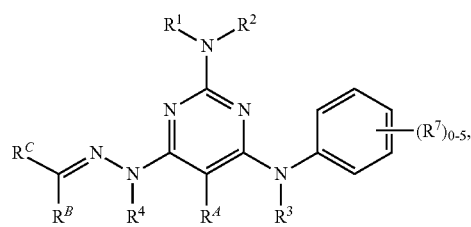

or a pharmaceutically acceptable salt thereof.
In some embodiments, the compound of Formula (I) is:

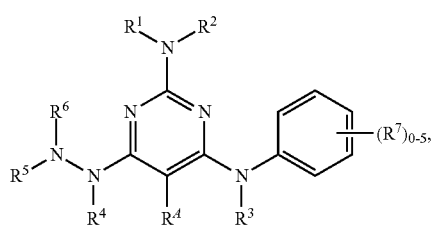

or a pharmaceutically acceptable salt thereof.
In some embodiments, the compound of Formula (I) is:

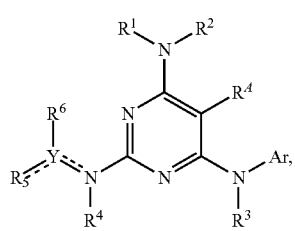

or a pharmaceutically acceptable salt thereof.

In some embodiments, the compound of Formula (I) is not:

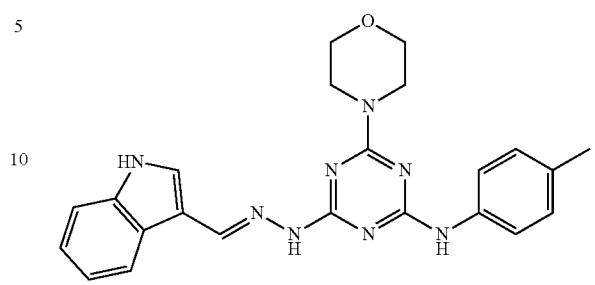

In some embodiments, the compound of Formula (I) is:

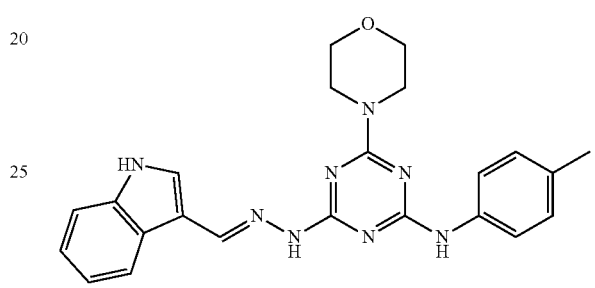

or a pharmaceutically acceptable salt thereof.
In some embodiments, the compound of Formula (I) is:

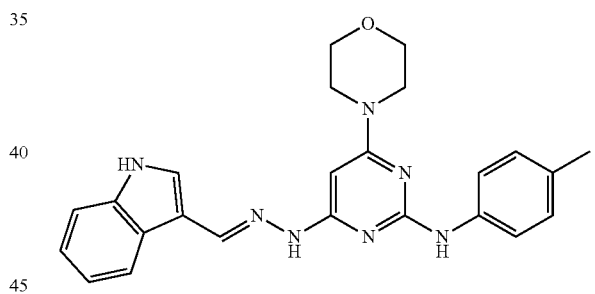

or a pharmaceutically acceptable salt thereof.
In some embodiments, the compound of Formula (I) is any one of the compounds provided in Table 8, or a pharmaceutically acceptable salt thereof.

In some embodiments, a salt of a compound of Formula I is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of Formula I include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formula I include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of Formula I, or pharmaceutically acceptable salts thereof, are substantially isolated.

Methods of Making

Compounds of Formula (I), including salts thereof, can be prepared using known organic synthesis techniques and can be synthesized according to any of numerous possible synthetic routes. A person skilled in the art knows how to select and implement appropriate synthetic protocols, and appreciates that a broad repertoire of synthetic organic reactions is available to be potentially employed in synthesizing compounds provided herein.

Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, $4^{th}$ Ed., Wiley & Sons, Inc., New York (2006).

Methods of Use

Cancer

In some embodiments, the compounds of the present disclosure inhibit enzyme phosphatidylinositol-3-phosphate 5-kinase type III (PIKfyve) in vitro, in vivo, or ex vivo. Inhibition of PIKfyve in a cell induces cytoplasmic vacuolization and subsequently cell death. The role of cytoplasmic vacuolization in cell death and survival is described, for example, in Oncotarget, 2016, 7(34), 55863-55889. That is, the compound may be used to induce death of a cancer cell. As such, in some embodiments, the present application provides a method of treating cancer in a subject, comprising administering to the subject a therapeutically effective amount of a compound of Formula (I), or a pharmaceutically acceptable salt thereof, or a pharmaceutically acceptable salt thereof. In some embodiments, the methods include a step of identifying the subject in need of cancer treatment. This step may include diagnosing the subject as having cancer by a treating physician.

In some embodiments, cancer is selected from the group selected from sarcoma, angiosarcoma, fibrosarcoma, rhabdomyosarcoma, liposarcoma, myxoma, rhabdomyoma, fibroma, lipoma, teratoma, lung cancer, breast cancer, bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney, adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, lymphoblastic leukemia, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, lymphoma, Hodgkin's lymphoma, non-Hodgkin's lymphoma (malignant lymphoma), Waldenstrom's macroglobulinemia, skin cancer, malignant melanoma, basal cell carcinoma, colorectal cancer, squamous cell carcinoma, Kaposi's sarcoma, moles dysplastic nevi, lipoma, colorectal carcinoma, osteosarcoma, pancreatic cancer, angioma, dermatofibroma, keloids, adrenal gland cancer, and neuroblastoma. In some embodiments, the cancer is lymphoblastic leukemia, lymphoma, colorectal cancer, glioblastoma multiforme (GBM), medulloblastoma, colorectal carcinoma, osteosarcoma, or pancreatic cancer.

Inflammation

In some embodiments, the compounds of the present suppresses IL12 and/or IL23 production in vitro, in vivo, or ex vivo. Inhibition of IL12/23 in a cell reduces pathology of an inflammatory disease or condition. Hence, the compounds of the present application are useful in treating or preventing inflammatory disorders or ameliorating symptoms associated with these disorders. Such disorders include sepsis (e.g., acute sepsis), alopecia, hearing loss syndrome, gout, arthritis, rheumatoid arthritis, sclerosis, inflammatory bowel disease, ankylosing spondylitis (AS), antiphospholipid antibody syndrome (APS), myositis, scleroderma, Sjogren's syndrome, systemic lupus erythematosus, vasculitis, familial mediterranean fever, neonatal onset multisystem inflammatory disease, Behçet's disease, dermatosis, type 1 diabetes, autoimmune disease, psoriasis, psoriatic arthritis, multiple sclerosis, Addison's disease, Graves' disease, Hashimoto's thyroiditis, myasthenia gravis, pernicious anemia, celiac disease, chronic inflammation, rheumatism, encephalomyelitis, postinfectious cerebellitis, neuromyelitis optica (e.g., Devic disease), encephalitis, metabolic encephalopathy, asthma, periodontitis, ulcerative colitis, Crohn's disease, sinusitis, and peptic ulcer. Symptoms associated with inflammatory disorders typically include chronic pain, redness, swelling of joints and other tissues, stiffness, fever, buildup of blood protein in organs, hair loss, fatigue, and damage to normal tissues. The compounds of the present application are useful in ameliorating these symptoms.

In one example, IL12/23-T helper 17 pathway as a mediator of psoriatic inflammation. Apilimod is a small molecule inhibitor of the lipid kinase PIKfyve that was originally discovered in a high throughput screen for inhibitors of IL-12:

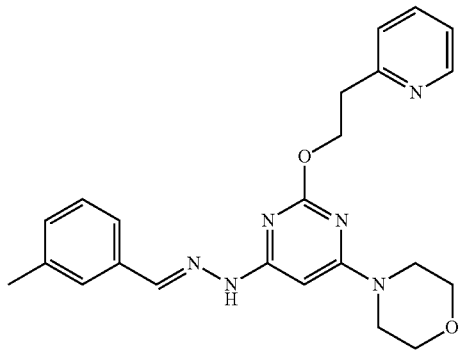 [SMILES: Cc1cccc(/C=N/Nc2cc(N3CCOCC3)nc(OCCc3ccccn3)n2)c1]

Apilimod suppresses IL12 and IL23 production by myeloid cells, and oral administration suppressed TH1 but not TH2 responses in mice. Oral administration to mice markedly reduced inflammatory histopathologic skin changes and decreased IFN-gamma production by ex vivo cells. A clinical trial in humans with stable psoriasis vulgaris skin plaques (See, Wada, Y, et al., Apilimod inhibits the production of IL-12 and IL-23 and reduces dendritic cell infiltration in psoriasis. PLoS One, 2012. 7(4): p. e35069) found that oral administration of apilimod caused substantial improvements in histology and clinical measurements of disease activity. IL12 and IL23 expression in skin lesions was significantly reduced. At the highest dose level (70 mg qd), 47% of patients had histologic improvement, and there was a 46% mean improvement in PASI (Psoriasis Area and Severity Index) score. However, the cutoff to move to a new phase II trial was not met, and the authors attributed the insufficient response (which was inferior to the intravenous medication ustekinumab) to inability to reach adequate drug levels. Apilimod has dose limiting toxicity at 105 mg bid (due to headache, flushing, hypoesthesia, dizziness, paresthesia). As shown in the present application, Example 3 targets PIKfyve even more specifically than apilimod, and has more efficacy and less toxicity in blocking secretion of IL12/23 than apilimod. Hence, the compounds of the present disclosure could be an effective oral treatment for humans with psoriasis and other inflammatory conditions (e.g., in which IL12/23 is implicated).

Combination Treatment

In some embodiments, the method of treating cancer or an inflammatory disease or condition in a subject further comprises administering to the subject an additional therapeutic agent, or pharmaceutically acceptable salt thereof. In this method, the compound of Formula (I) and the additional therapeutic agent may be administered to the subject simultaneously (e.g., in the same dosage form or in separate dosage forms), or consecutively (e.g., additional therapeutic agent may be administered before or after the compound of Formula (I), or a pharmaceutically acceptable salt thereof.

Suitable examples of additional therapeutic agents include an anti-HER2 agent (e.g., trastuzumab, pertuzumab, lapatinib), a pain relief agent (e.g., a nonsteroidal anti-inflammatory drug such as celecoxib or rofecoxib), an antinausea agent, or an additional anticancer agent (e.g., paclitaxel, docetaxel, daunorubicin, epirubicin, fluorouracil, melphalan, cis-platin, carboplatin, cyclophosphamide, mitomycin, methotrexate, mitoxantrone, vinblastine, vincristine, ifosfamide, teniposide, etoposide, bleomycin, leucovorin, taxol, herceptin, avastin, cytarabine, dactinomycin, interferon alpha, streptozocin, prednisolone, irinotecan, sulindac, 5-fluorouracil, capecitabine, oxaliplatin/5 FU, abiraterone, letrozole, 5-aza/romidepsin, or procarbazine). Other examples of additional therapeutic agents include nexavar, sutent, torisel, afinitor (everolimus), axitinib, pazopanib, levatinib, interleukin-2, and combinations thereof. In some embodiments, the method of treating cancer in a subject further comprises administering to the subject a proteasome inhibitor. Exemplary proteasome inhibitors include lactacystin, bortezomib, dislfiram, salinosporamide A, carfilzomib, ONX0912, CEP-18770, MLN9708, epoxomicin, and MG132). Non-limiting examples of proteasome inhibitors include marizomib (NPI-0052), bortezomib (Velcade®), and carfilzomib (Kyprolis®). In some embodiments, the additional therapeutic agent is BRAF-V600E inhibitor (e.g., vemurafenib).

In some embodiments, an additional therapeutic agent includes an anti-inflammatory agent. Suitable examples include nonsteroidal anti-inflammatory drugs (NSAID) such as celecoxib, rofecoxib, ibuprofen, naproxen, aspirin, diclofenac, sulindac, oxaprozin, piroxicam, indomethacin, meloxicam, fenoprofen, diflunisal, methotrexate, BAY 11-7082, or a pharmaceutically acceptable salt thereof. Suitable examples of steroid anti-inflammatory agents include cortisol, corticosterone, hydrocortisone, aldosterone, deoxycorticosterone, triamcinolone, bardoxolone, bardoxolone methyl, triamcinolone, cortisone, prednisone, and methylprednisolone, or a pharmaceutically acceptable salt thereof. In some embodiments, the anti-inflammatory agent is selected from: ixekizumab, secukinumab (anti-IL17A), guselkumab (anti-IL23), TNF inhibitors (adalimumab, etanercypt, infliximab), and ustekinumab (anti-IL12/23). The compounds of the present application may also be used in combination with non-specific immunosupressants, including phototherapy, laser exposure, cyclosporine, and methotrexate.

Pharmaceutical Compositions

The present application also provides pharmaceutical compositions comprising an effective amount of a compound of Formula (I) disclosed herein, or a pharmaceutically acceptable salt thereof; and a pharmaceutically acceptable carrier. The pharmaceutical composition may also comprise any one of the additional therapeutic agents described herein (e.g., vemurafenib). In certain embodiments, the application also provides pharmaceutical compositions and dosage forms comprising any one the additional therapeutic agents described herein. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms may contain any one of the compounds and therapeutic agents described herein in the range of 0.005% to 100% with the balance made up from the suitable pharmaceutically acceptable excipients. The contemplated compositions may contain 0.001%-100% of any one of the compounds and therapeutic agents provided herein, in one embodiment 0.1-95%, in another embodiment 75-85%, in a further embodiment 20-80%, wherein the balance may be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein may conveniently be presented in a unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, MD (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, any one of the compounds and therapeutic agents disclosed herein are administered orally. Compositions of the present application suitable for oral administration may be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In the case of tablets for oral use, carriers that are commonly used include lactose, sucrose, glucose, mannitol, and silicic acid and starches. Other acceptable excipients may include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, saline (e.g., 0.9% saline solution) or 5% dextrose solution, immediately prior to use. Extemporaneous injection solutions and suspensions may be prepared from sterile powders, granules and tablets. The injection solutions may be in the form, for example, of a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol,* 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of any one of the compounds and therapeutic agents disclosed herein, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

The compounds and therapeutic agents of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides an implantable drug release device impregnated with or containing a compound or a therapeutic agent, or a composition comprising a compound of the present application or a therapeutic agent, such that said compound or therapeutic agent is released from said device and is therapeutically active.

Dosages and Regimens

In the pharmaceutical compositions of the present application, a compound of Formula (I) is present in an effective amount (e.g., a therapeutically effective amount).

Effective doses may vary, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, an effective amount of a compound of Formula (I) can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg).

In some embodiments, an effective amount of a compound of Formula (I) is about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month).

Kits

The present invention also includes pharmaceutical kits useful, for example, in the treatment of disorders, diseases and conditions referred to herein, which include one or more containers containing a pharmaceutical composition comprising a therapeutically effective amount of a compound of the present disclosure. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit. The kit may optionally include any one of the additional therapeutic agents described herein (e.g., vemurafenib), or a pharmaceutically acceptable salt thereof, in any one of amounts and dosage forms described herein.

Definitions

As used herein the term "$EC_{50}$ (µM)" refers to the µM concentration of a compound that is required for 50% activity in a vacuolization assay.

As used herein, the term "about" means "approximately" (e.g., plus or minus approximately 10% of the indicated value).

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "aromatic" refers to a carbocycle or heterocycle having one or more polyunsaturated rings having aromatic character (i.e., having (4n+2) delocalized π (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methylpropan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di($C_{n-m}$-alkyl)amino" refers to a group of formula —$N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —$NHS(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —$S(O)_2NH_2$.

As used herein, the term "$C_{n-m}$ alkylaminosulfonyl" refers to a group of formula —$S(O)_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —$S(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —$NHS(O)_2NH_2$.

As used herein, the term "$C_{n-m}$ alkylaminosulfonylamino" refers to a group of formula —$NHS(O)_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —$NHS(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —$NHC(O)NH_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —$NHC(O)N(alkyl)_2$, wherein each alkyl group independently has n to m carbon atoms. In some embodiments, each alkyl group has, independently, 1 to 6, 1 to 4, or 1 to 3 carbon atoms.

As used herein, the term "carbamyl" to a group of formula —$C(O)NH_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —$C(O)N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —$S(O)_2$-alkyl, wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(=O)— group, which may also be written as C(O).

As used herein, the term "carboxy" refers to a —C(O)OH group.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphtyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C=O), or attached to a heteroatom forming a sulfoxide or sulfone group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, N=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the PIKfyve with a compound of the invention includes the administration of a compound of the present invention to an individual or patient, such as a human, having PIKfyve, as well as, for example, introducing a compound of the invention into a sample containing a cellular or purified preparation containing the PIKfyve.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

EXAMPLES

Example 1—(E)-4-(2-((1H-indol-3-yl)methylene)hydrazinyl)-6-morpholino-N-(p-tolyl)-1,3,5-triazin-2-amine Physical Properties The compound has a molecular weight of 428.5. It is soluble in DMSO. In addition, solutions of at least 10 mg/ml can be prepared using a mixture of DMSO (10%), cremaphor (20%), and water (70%).

Chemical Synthesis

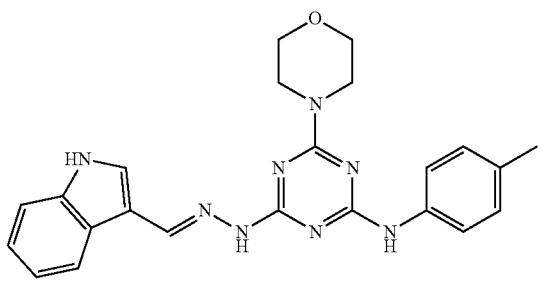 [SMILES: Cc1ccc(Nc2nc(N/N=C/c3c[nH]c4ccccc34)nc(N3CCOCC3)n2)cc1]

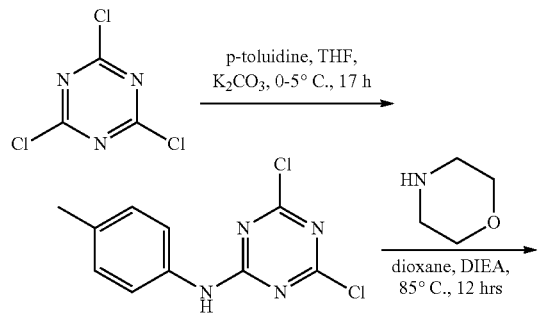

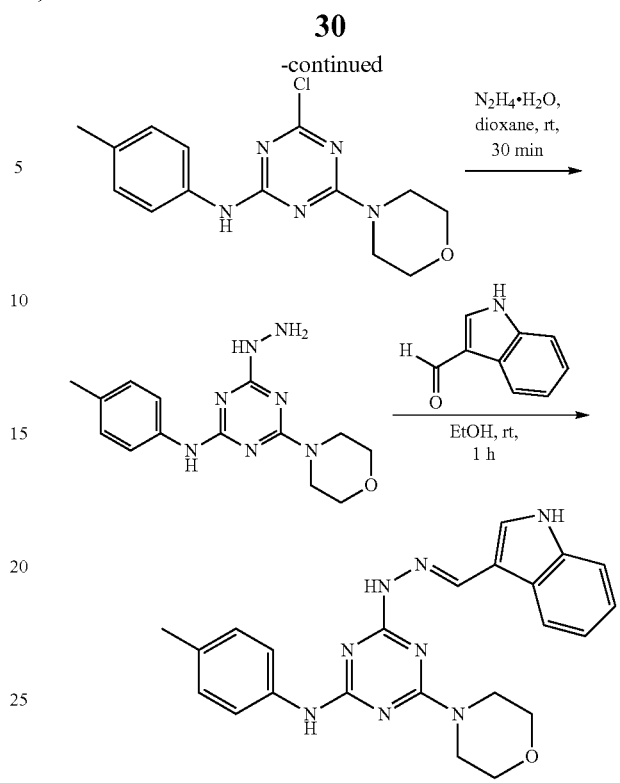

Step 1

To a cold (0-5° C.) stirred suspension of 2,4,6-trichloro-[1,3,5]triazine (1.84 g, 10 mmol) and K$_2$CO$_3$ (1.38 g, 10 mmol) in dry THF (30 mL) was added dropwise a solution of p-toluidine (1.07 g, 10 mmol) in dry THF (20 mL). Then the mixture was stirred for 3 hrs while slowly warming to ambient temperature. After stirring for 14 hrs at ambient temperature, the reaction was monitored by LCMS. The mixture was diluted with EA (200 mL) and then acidified with 1 N aqueous hydrochloric acid to pH=6-7. The organic phase was separated, rinsed successively with water, saturated aqueous sodium bicarbonate and brine (each around 20 mL) and dried over anhydrous Mg$_2$SO$_4$. The solution was filtered and concentrated in vacuum on a rotary evaporator to afford (4,6-dichloro-[1,3,5]triazin-2-yl)-p-tolyl-amine (2.33 g, yield: 91%) as a yellow solid.

$^1$H NMR (400 MHz, DMSO-d6): δ=11.05 (s, 1H), 7.47 (d, J=8.4 Hz, 2H), 7.20 (d, J=8.0 Hz, 2H), 2.29 (s, 3H).

Step 2

To a stirred solution of (4,6-dichloro-[1,3,5]triazin-2-yl)-p-tolyl-amine (2.33 g, 9.13 mmol) in dioxane (50 mL), was added DIEA (1.17 g, 9.13 mmol) and morpholine (795 mg, 9.13 mmol) and the resulting mixture was heated at 85° C. for 12 hrs. The reaction mixture was monitored by LCMS. The reaction mixture was cooled to ambient temperature, diluted with water (100 mL) and stirred for 1 hr. The white precipitate was filtered and dried in vacuum to give (4chloro-6-morpholin-4-yl-[1,3,5]triazin-2-yl)-p-tolyl-amine (1.94 g, yield: 69%) as a white solid.

$^1$H NMR (400 MHz, DMSO-d6): δ=10.03 (s, 1H), 7.50 (d, J=6.4 Hz, 2H), 7.12 (d, J=8.0 Hz, 2H), 2.85-3.60 (m, 8H). 2.26 (s, 3H).

Step 3

To a solution of (4-chloro-6-morpholin-4-yl-[1,3,5]triazin-2-yl)-p-tolyl-amine (300 mg, 0.98 mmol) in dioxane (20 mL) was added hydrazine hydrate (2 mL) and the mixture was stirred at rt for 30 min. The reaction was monitored by LCMS. The mixture was concentrated in vacuum to give (4-hydrazino-6-morpholin-4-yl-[1,3,5]triazin-2-yl)-p-tolyl-amine (252 mg, yield: 85%) as a white solid.

$^1$H NMR (400 MHz, DMSO-d6): δ=8.97 (s, 1H), 7.96 (s, 1H), 7.59 (d, J=8.4 Hz, 2H), 7.03 (d, J=8.0 Hz, 2H), 4.18 (s, 2H), 3.77-3.58 (m, 8H), 2.22 (s, 3H).

Step 4

To a solution of (4-hydrazino-6-morpholin-4-yl-[1,3,5]triazin-2-yl)-p-tolyl-amine (100 mg, 0.33 mmol) in EtOH (20 mL) was added 1H-indole-3-carbaldehyde (95.8 mg, 0.66 mmol), and the mixture was stirred at rt for 1 hr. The mixture was concentrated in vacuum to give a residue, which was pre-purified by column chromatography followed by prep-HPLC purification to give {4-[N'-(1H-indol-3-ylmethylene)-hydrazino]-6-morpholin-4-yl-[1,3,5]triazin-2-yl}-p-tolyl-amine (40 mg, yield: 28%) as a white solid.

$^1$H NMR (400 MHz, CD$_3$OD): δ=8.45-8.34 (m, 1H), 8.27 (s, 1H), 7.71-7.52 (m, 3H), 7.40 (d, J=8.0 Hz, 1H), 7.26-7.08 (m, 4H). 3.92-3.70 (m, 8H), 2.32 (s, 3H). MS: m/z 429.0 (M+H$^+$).

Biological Activity 50 nM of Example 1 caused a greater than 99% inhibition of PIKfyve. No other kinase was blocked to that extent by 50 nM of Example 1, indicating its high degree of selectivity.

Glioblastoma and Medulloblastoma

Figure 3:
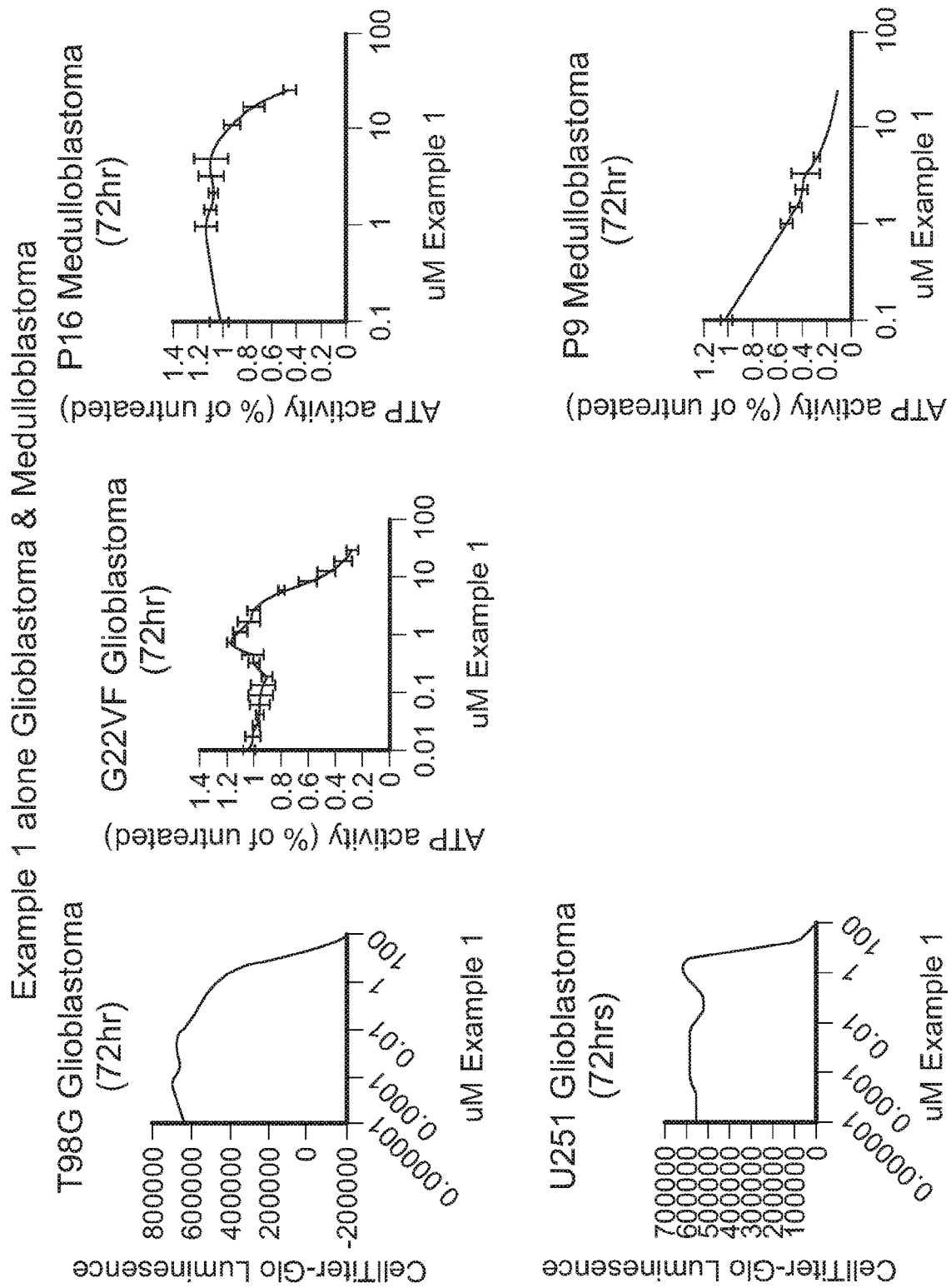
FIG. 3 contains line plots showing glioblastoma multiforme and medulloblastoma cell viability assessed by cell titer-Glo luminescence (ATP level) assay using compound of Example 1.

Human Glioblastoma multiforme cells (T98G, G22VF, U251) and human medulloblastoma cells (p16, p9) were incubated with various concentrations of Example 1 for 72 hours, and then cell viability assessed by cell titer-Glo luminescence (ATP level) assay. Cells were killed effectively by a range of concentrations, depending on the cell line, as demonstrated in FIG. 3.

Methods: Example 1 was dissolved into DMSO (ATCC) at a concentration of 40 mM, this stock was further diluted to 2× the highest final working concentration into complete medium consisting of DMEM (Life Technologies), penicillin/streptomycin antibiotic solution (Life Technologies), and 10% FBS (Seradigm). This stock was dispensed into the final column of a white-walled, flat-bottomed 96-well plate (Corning). Serial dilutions (1.5× or 2× depending on the assay) were then made using complete medium down to the lowest assayed concentration of Example 1. The final column of the 96-well plate was saved as a vehicle-only control and included DMSO diluted 1:250 in complete medium.

Cells, which had been grown in a 5% CO$_2$, 37° C. incubator using standard tissue culture methods, were harvested in log phase when their confluence was 50-85%. To do so, they were washed with 1×PBS pH 7.4 (Life Technologies) then incubated with a 0.05% Trypsin-EDTA solution (Life Technologies) at room temperature until cells visibly detached from the plate. The cell suspension was then pipetted up and down several times to disperse cell clusters, then immediately diluted 1:5 into complete medium. A small aliquot of this cell suspension was used for counting on an Accuri C6 Cytometer (BD Biosciences) using forward and side scatter to gate for a live cell population. The remainder of the suspension was centrifuged at 180×g, supernatant was removed, and pellet was resuspended in complete medium at a final concentration of 100 cells/μL. 50 μL of this suspension was then plated into each well of the 96-well plate containing Example (prepared as described above), resulting in each well containing 100 μL of complete medium, 5000 cells, <2 μL DMSO, and the indicated concentration of Example 1.

These plates were placed in a 5% CO$_2$, 37° C. incubator. After 72 hrs of incubation, relative ATP content was measured as an indirect indication of the number of viable cells per well. 100 μL of CellTiterGlo reagent (Promega) which had been prepared per the manufacturer's instructions was added to each well. This reaction was protected from light and incubated for 10 min at room temperature, then total luminescence was read using a Synergy H1 microplate reader (Biotek).

Raw luminescence numbers or relative ATP concentration (reported as a percentage of the vehicle-treated control) are show. All data points represent the mean of 2-3 independent experimental replicates, and error bars represent standard deviation.

Colorectal Carcinoma

Figure 4:
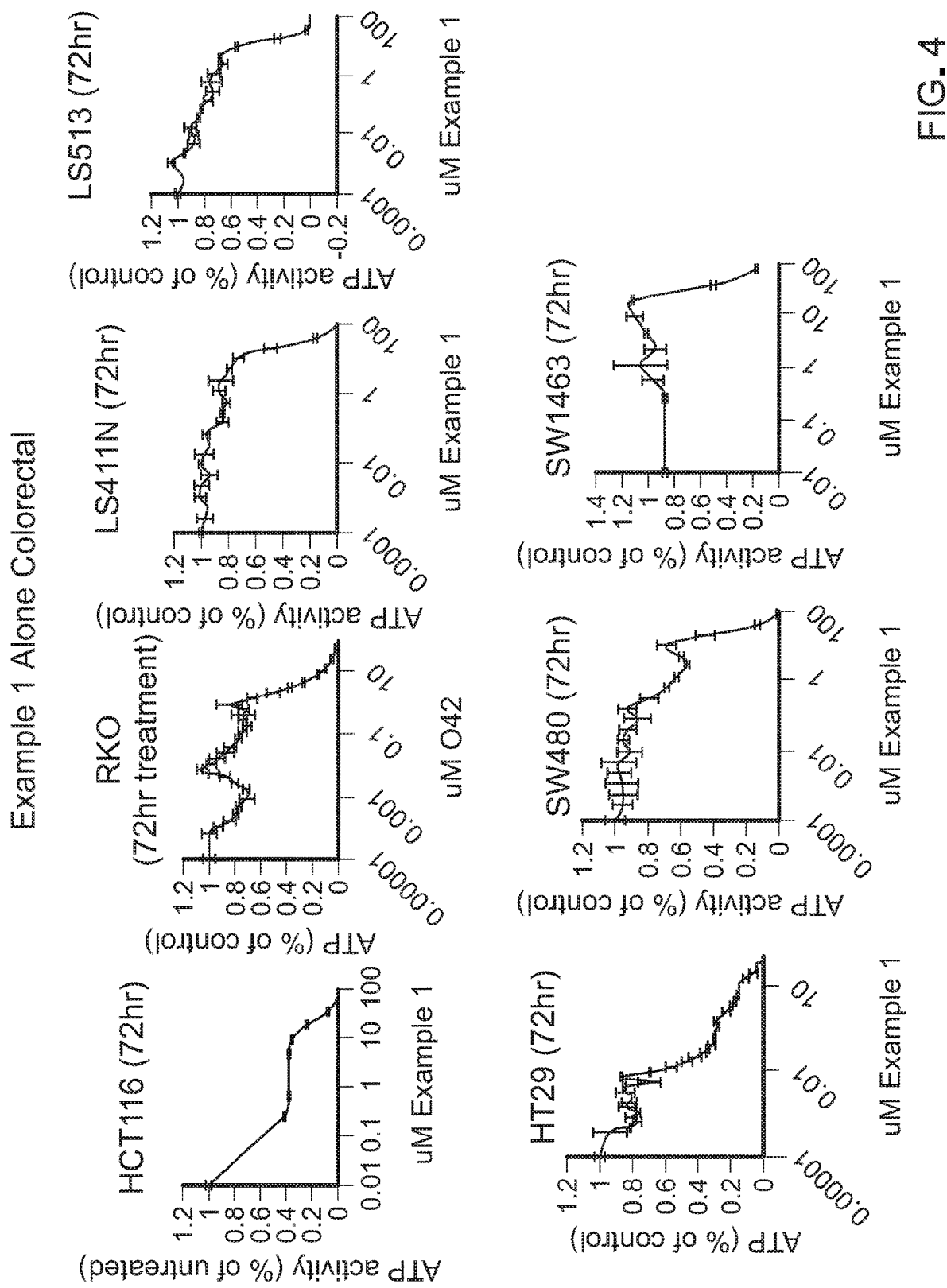
FIG. 4 contains line plots showing killing by Example 1 of colorectal carcinoma cell lines. (ATP activity is defined by use of the Cell-titer glow luminescence assay).

Human colorectal carcinoma cell lines were similarly tested for killing by the compound. (ATP activity is defined by use of the Cell-titer glow luminescence assay). As shown in FIG. 4, some of the colorectal cancer cells (HCT116, HT29) were more sensitive to the compound-induced death than were the brain tumor cell lines. All experiments were performed using RPMI media (Life Technologies) as the base formulation for "complete" media. HT29 cells require physical scraping in addition to trypsin to dissociate from tissue culture plastic.

Osteosarcoma

Figure 5:
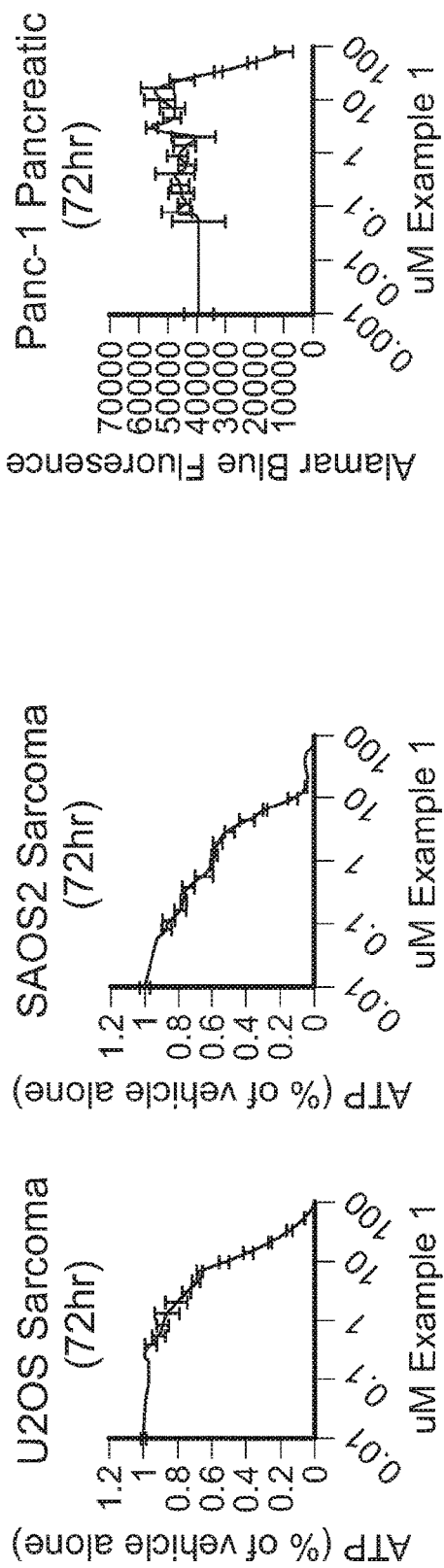
FIG. 5 contains line plots showing killing by Example 1 of osteosarcoma and pancreatic cell lines.
Figure 5:
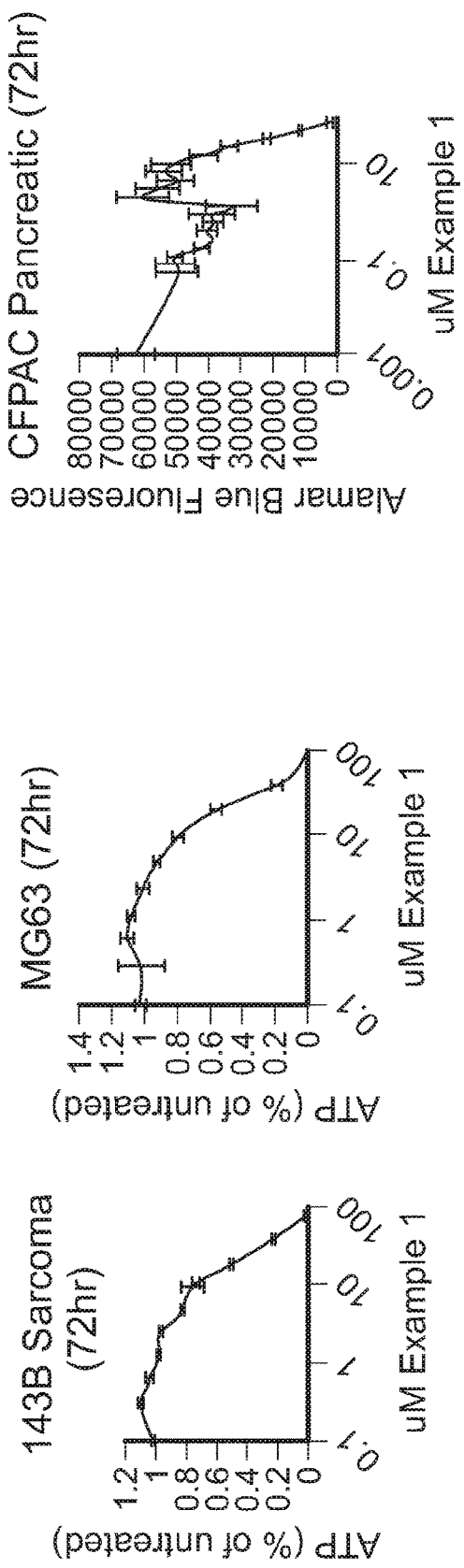

Human osteosarcoma cells (U2OS, 143B, MG63, and SAOS2) and human pancreatic cancer cells (Panc-1, CFPAC) were similarly tested for killing by the compound, as shown in FIG. 5. All experiments in FIG. 5 were performed using DMEM:F12 media (Life Technologies) as the base formulation for "complete" media for experiments with 143B and MG63 cells. Also, Alamar Blue was used to assay the relative number of viable cells per well after 72 hrs of growth. For these assays, growth media was removed from the cells, and replaced with fresh ("complete) media containing Alamar Blue reagent (Life Technologies) diluted 1:10. Plates were incubated at 5% CO$_2$, 37° C. for 40 min then removed from the incubator and fluorescence was measured using a Synergy H1 microplate reader (Excitation: 560 nm Emission: 590 nm). Values represent raw photo counts minus the value of a well with Alamar Blue reagent (1:10 in medium) but no cells.

Lymphoma

Figure 6:
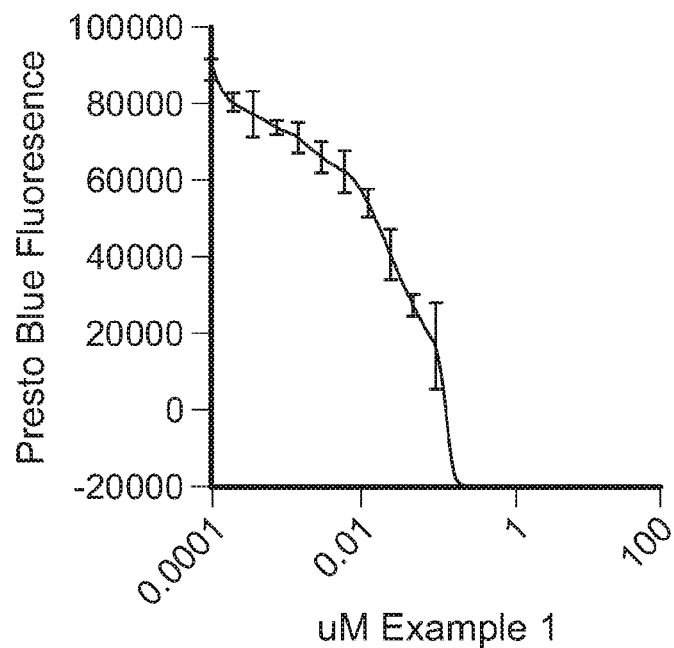
FIG. 6 contains line plots showing killing of murine lymphoma cells (E2409, EC+F) by Example 1.
Figure 6:
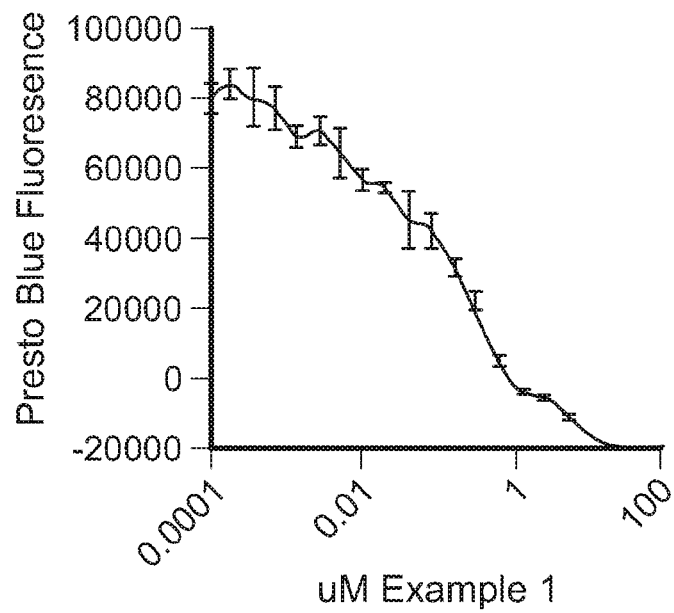

Murine lymphoma cells (E2409, EC+F) were killed by relatively low concentrations of the compound in a 48 hour assay, with survival determined by cell counting, as shown in FIG. 6. Murine lymphoma cells (E2409, EC+F) were killed by relatively low concentrations of Example 1 in a 48 hour assay. All experiments in FIG. 6 were performed using RPMI media (Life Technologies) was used as the base formulation and culture medium also contained 1 mM Sodium Pyruvate, 100 mM HEPES, 2 mM additional L-Glutamine, 55 uM 2-mercaptoethanol, and 1×MEM NEAA Solution (all from Life Technologies). Trypsin was not necessary for these non-adherent cells. Presto Blue reagent (Life Technologies) was used as an endpoint assay using the same procedure described in previously for Alamar Blue, with a 30 minute incubation time.

Figure 7:
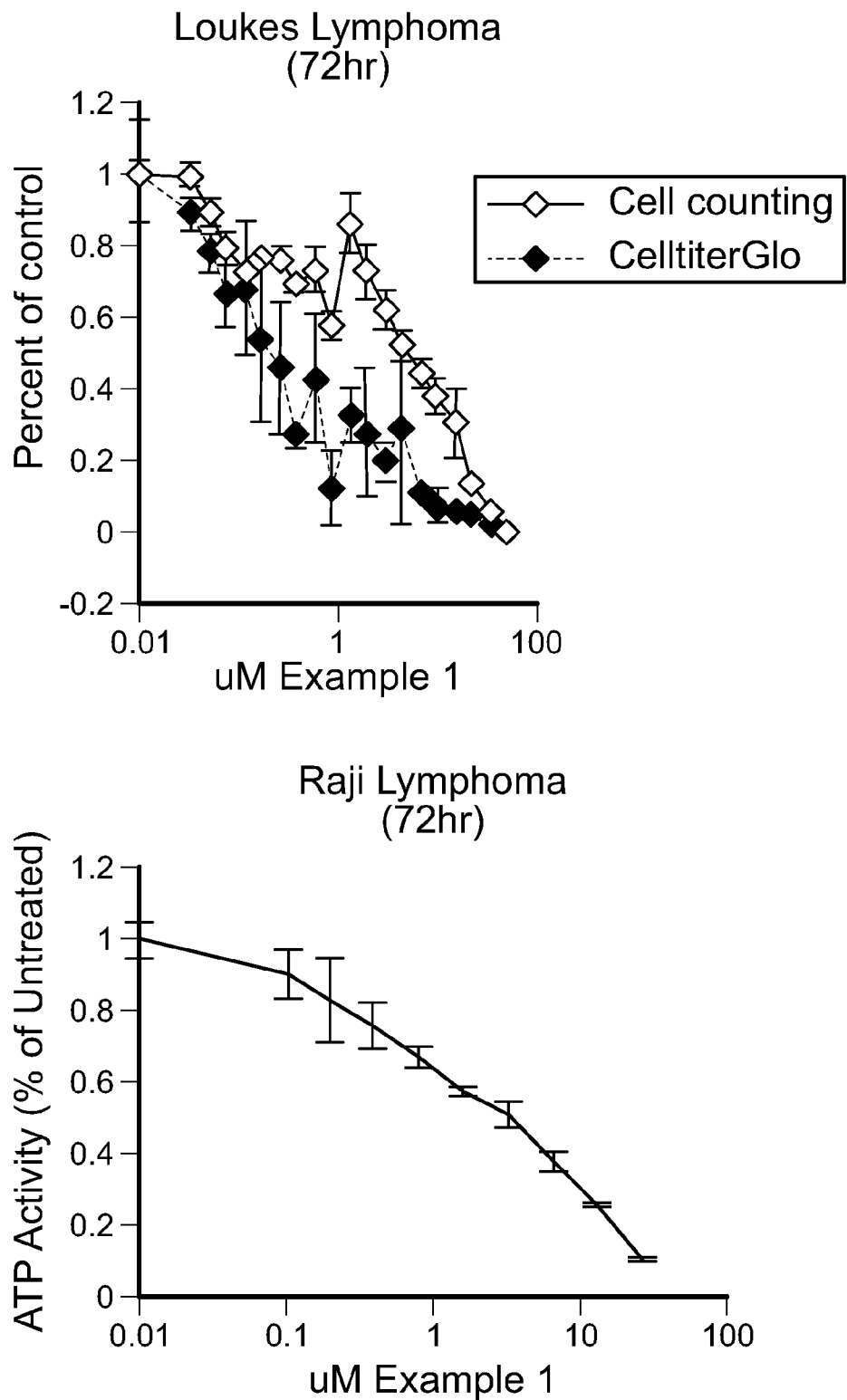
FIG. 7 contains line plots showing killing of human lymphoma cell lines by Example 1.

Human lymphoma cell lines were incubated for 72 hours with various concentrations of the compound, and survival determined by cell counting or by ATP assay, as shown in FIG. 7. In the lymphoma experiments, RPMI media (Life Technologies) was used as the base formulation for "complete" media. Trypsin was not needed for these non-adherent cell lines. For the "cell-counting" data, cells were pipetted up and down to evenly disburse, then 10 μL of the suspension was counted using an Accuri C6 cytometer, using on forward and side scatter to gate on a viable population.

Figure 2:
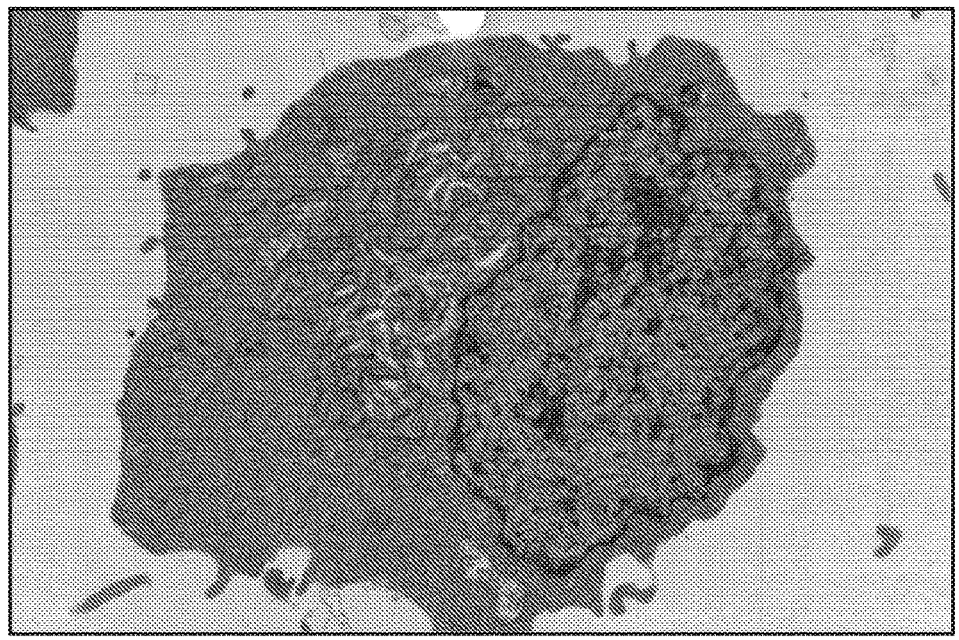
FIG. 2 shows electron micrographs of murine lymphoma cells treated with vehicle only (left) or Example 1 (right).
Figure 2:
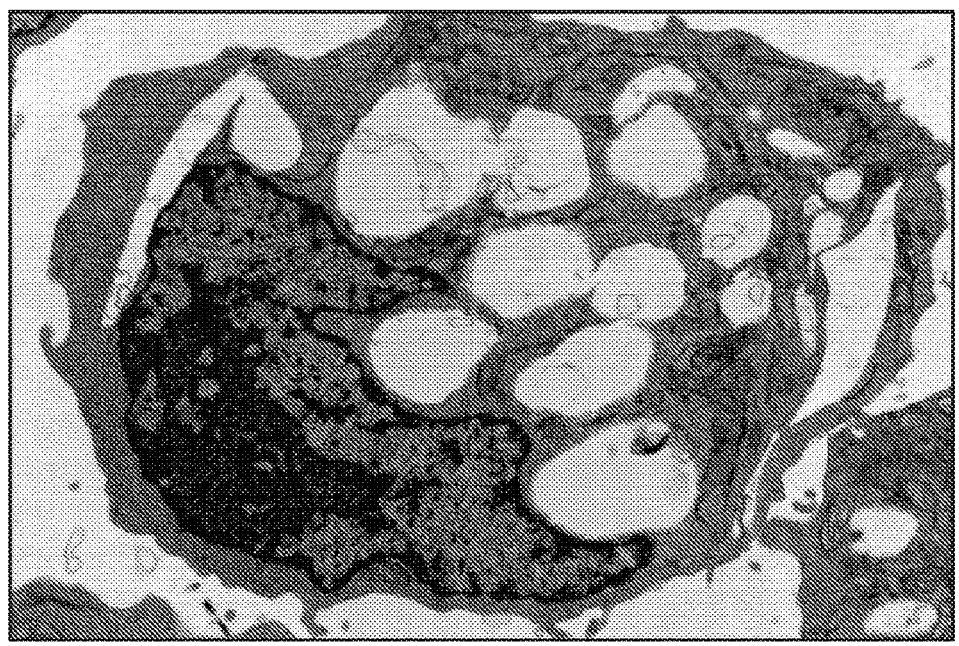

Vacuolization due to treatment with Example 1 compound was extremely rapid, becoming visible by light microscopy within 30 minutes or less. Electron micrographs of murine lymphoma cells treated with vehicle only (left) or Example 1 (right) are shown in FIG. 2.

Autophagy Inhibition

Macroautophagy (hereafter "autophagy") is a process that requires precise fusion of endosomes, autophagosomes, and lysosomes. Lysates from cells treated with Example 1 were prepared and probed by western blotting for LC3-I and LC3-II. Increased levels of LC3-II and increased p62 (sequestesome) were found showing the increased drive to undergo autophagy, in the face of inability to complete the process (i.e. ineffective autophagy). Lysosomes are the final destination of proteins destined for degradation by autophagy, and proteolysis in this organelle depends upon cathepsins among other enzymes. Cathepsin levels were measured by western blotting, and it was found that the mature forms became less abundant in Example 1 treated glioblastoma cells, while the precursor forms (procathepsin) accumulated, indicating failure to deliver these degradative enzymes to the appropriate low pH compartment.

Figure 23:
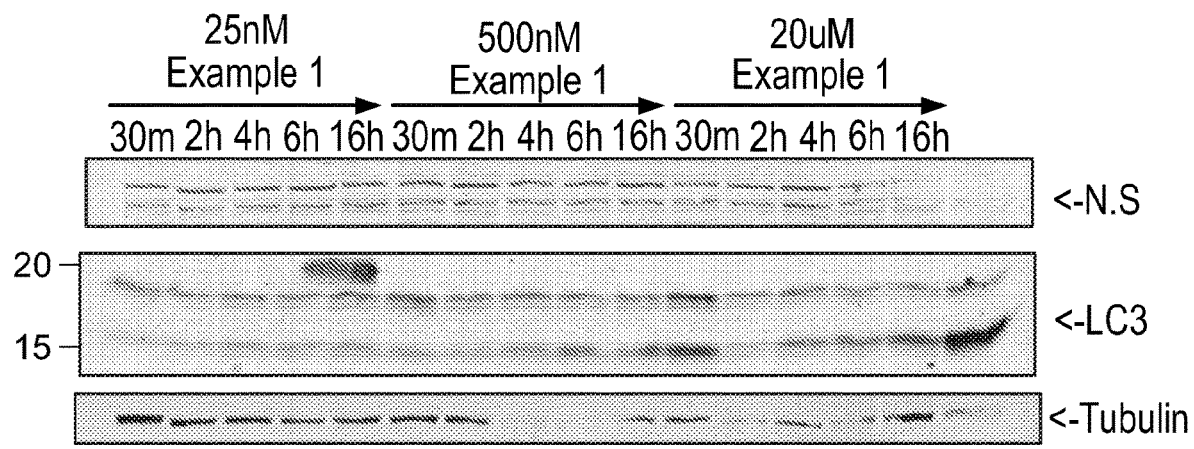
FIG. 23 contains images showing induction of autophagy the Example 1 as evidenced by accumulation of LC3 over time.

FIG. 23 contains images showing induction of autophagy the Example 1 as evidenced by accumulation of LC3 over time. U251 glioblastoma cells were treated with 25, 500, or 20,000 nM MC042 for the indicated time periods, and then lysates prepared and blotted for LC3 and tubulin (loading control). Starting a t 6 hours, and becoming more evident by 24 hours, LC3-II (the lower band marked LC3) accumulated, indicating activation of autophagy. However, p62 was not degraded, thus indicating that autophagy was not effective at removing proteins from the cell.

Figure 24:
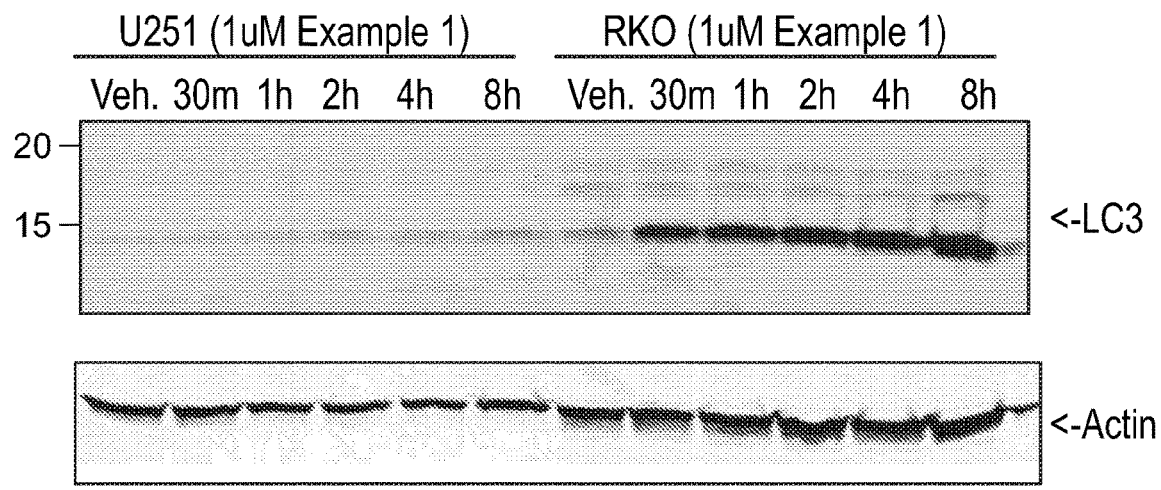
FIG. 24 contains western blot images showing LC3 accumulation in U251 (glioblastoma) and RKO (colon cancer) cells treated with 1 µM of Example 1.

FIG. 24 shows that, in similar fashion, U251 (glioblastoma) and RKO (colon cancer) cells were treated with 1 µM of Example 1 for the indicated time periods, and then analyzed for LC3 accumulation by western blotting. RKO cells had a dramatic and rapid induction of LC3, while that of U251 was less robust.

Figure 25:
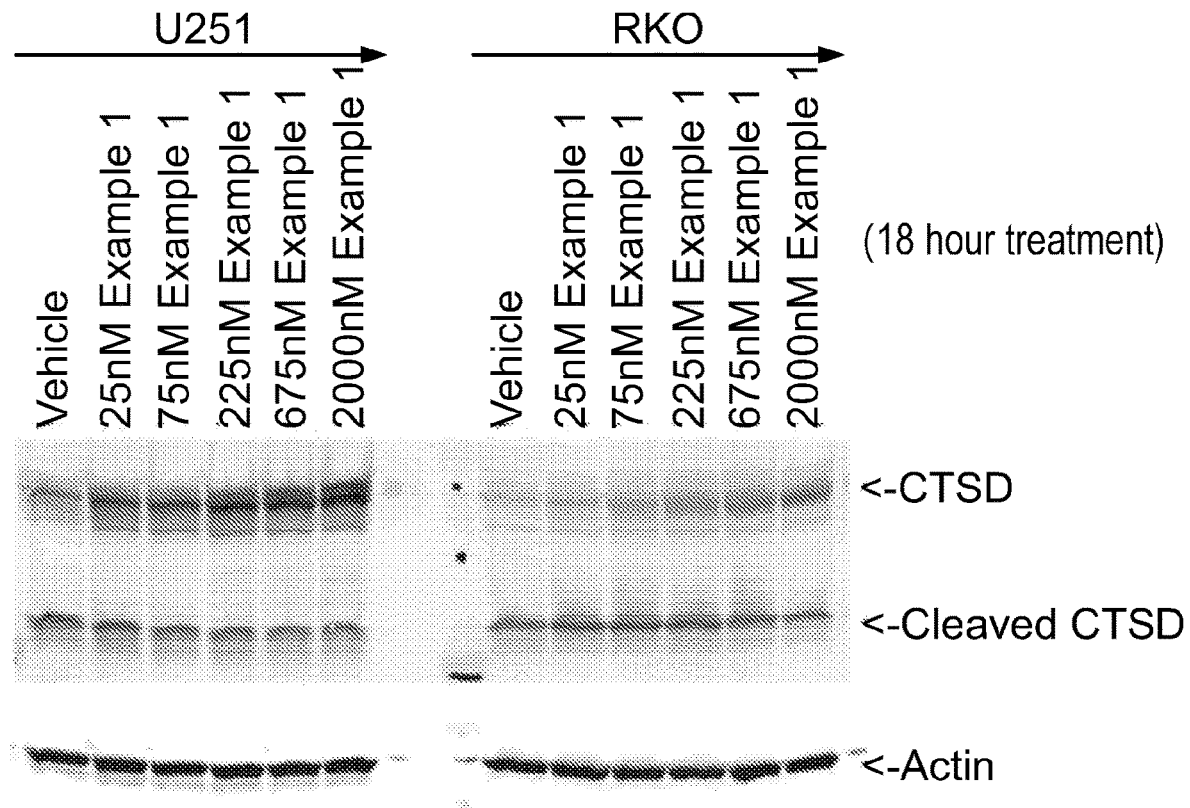
FIG. 25 contains images showing that Example 1 causes accumulation of uncleaved precursor cathepsin D ("CTSD") and relative loss of mature cleaved cathepsin.

FIG. 25 shows that Example 1 causes accumulation of uncleaved precursor cathepsin D ("CTSD") and relative loss of mature cleaved cathepsin. U251 or RKO cells were treated with Example 1 at the indicated concentrations for 18 hours, and then analyzed by western blotting for cathepsin D and actin (loading control).

U251 or RKO cells were plated onto 10 cm tissue culture dishes and grown in the conditions described previously. When cells were growing in log phase and reached approximately 60% confluency, Example 1 was diluted into the growth media at the indicated concentrations. Cells were incubated at 5% $CO_2$, 37° C. for 18 hr, then washed and harvested as described previously. Cells were pelleted by centrifugation at 180×g, resuspended in 20 mL of 1×PBS pH 7.4, and centrifuged again. The supernatant was removed and the pellet was resuspended in 100 µL RIPA buffer containing 1× protease and phosphatase inhibitor cocktails (EMD Millipore) and incubated on ice for 1 hr. After this incubation, the remaining cell debris was pelleted by centrifuging at 17,000×g, and the lysate was transferred to a clean tube on ice and 100 µL of Laemlli buffer (BioRad) prepared per the manufacturer's instructions was added. Tubes were incubated at 100° C. for 5 minutes then vortexed and transferred back to ice. Proteins from 50 µL of each sample were separated by electrophoresis on a 15% Tris-HCl acrylamide gel (Bio Rad), then transferred onto PVDF-FL membrane (EMD-Millipore). The Membrane was incubated in SeaBlock reagent (EMD-Millipore) at room temperature for 30 minutes, then overnight at 4° C. in a solution containing goat-anti-hCathepsinD (1:1000, R&D systems) and mouse-anti-actin (1:5000, Chemicon) antibodies diluted into SeaBlock. The membrane was washed 4 times using an excess of 1×TBS+1% Tween-20. Then incubated for 2 hr at room temperature in SeaBlock containing IR-Dye-conjugated secondary antibodies (Li-Cor) recognizing goat and mouse (1:35,000 dilution). After washing 4 more times with TBS+Tween, the membrane was imaged using an Odyssey scanner (Li-Cor).

Example 2—(E)-N-(4-((4-(2-((1H-indol-3-yl)methylene)hydrazinyl)-6-morpholino-1,3,5-triazin-2-yl)amino)phenyl)-5-(2-oxohexahydro-1H-thieno[3,4-d]imidazol-4-yl)pentanamide

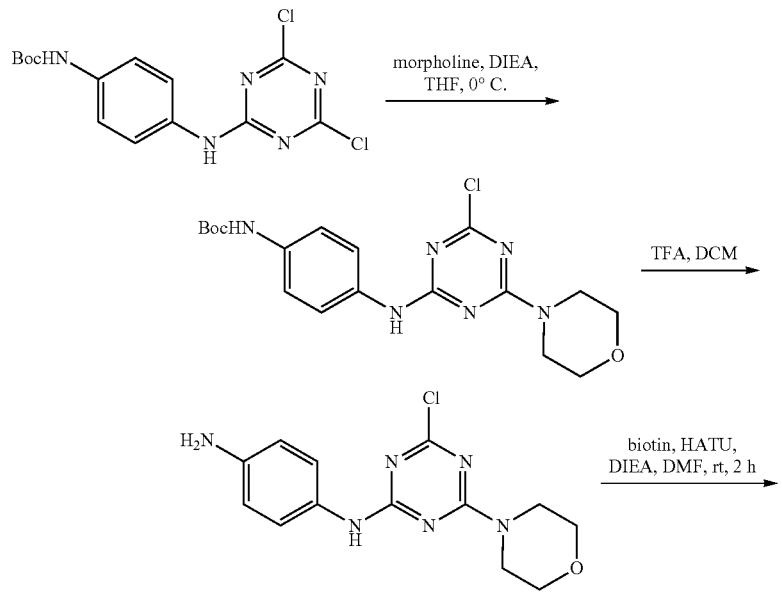

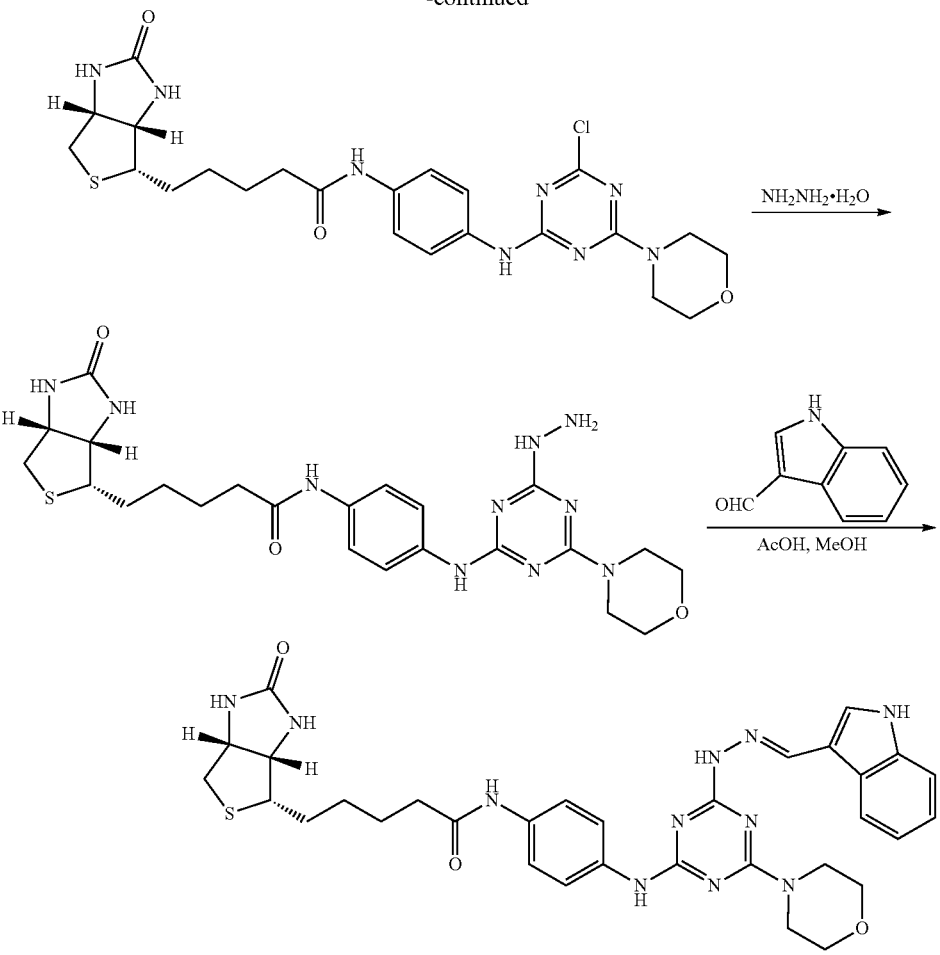

The title compound was prepared using the methods and procedures similar to those described for Example 34.

$^1$H NMR (400 MHz, DMSO-$d_6$): δ=11.44 (brs, 1H), 10.64 (brs, 1H), 9.80 (brs, 1H), 9.19-9.16 (m, 1H), 8.45-8.44 (m, 1H), 8.32 (s, 1H), 8.07-8.00 (m, 1H), 7.70-7.37 (m, 5H), 7.23-7.15 (m, 1H), 6.48 (s, 1H), 6.38 (s, 1H), 4.32-4.29 (m, 1H), 4.15-4.14 (m, 1H), 3.84-3.83 (m, 8H), 3.16-3.10 (m, 1H), 2.85-2.80 (m, 1H), 2.59-2.57 (m, 2H), 2.39-2.32 (m, 2H), 1.64-1.45 (m, 4H), 1.40-1.33 (m, 2H). MS: m/z 656.1 (M+H$^+$)

Bioactivity

Figure 9:
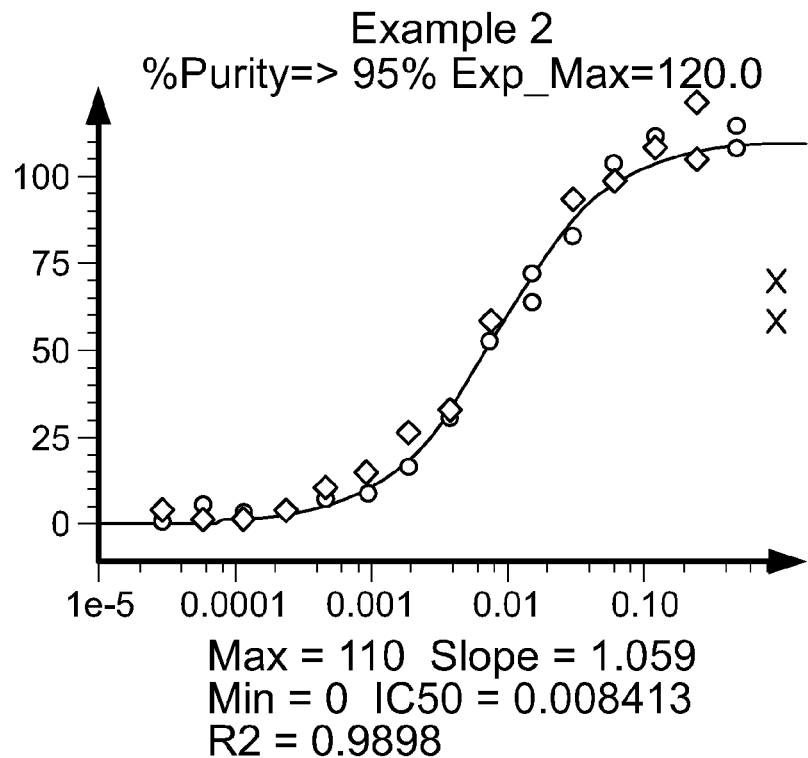
FIG. 9 is a line plot showing activity of Example 2 (a biotinylated derivative of the compound of Example).

Example 2 is a biotinylated derivative of the compound of Example 1. This compound demonstrated vacuolization activity in cells in culture, with EC$_{50}$ of 0.008 μM. See FIG. 9.

Example 3—(E)-4-(2-((1H-indol-3-yl)methylene)hydrazinyl)-6-morpholino-N-(p-tolyl)pyrimidin-2-amine

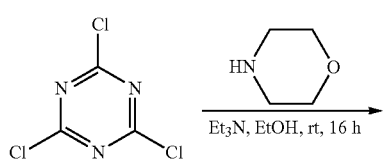

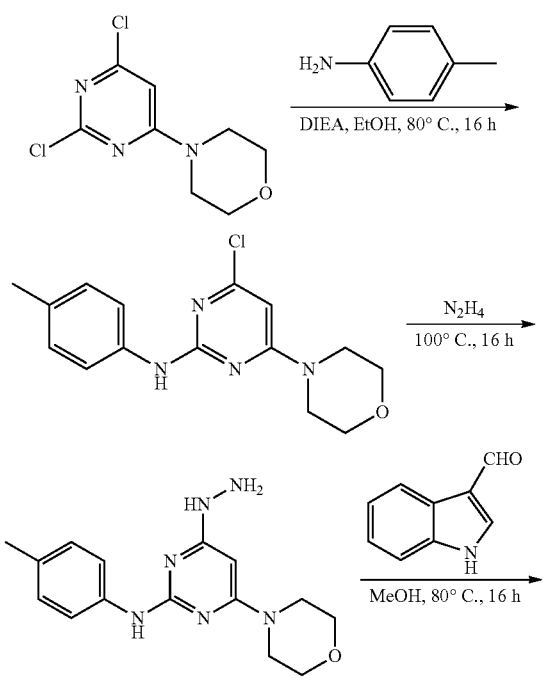

-continued

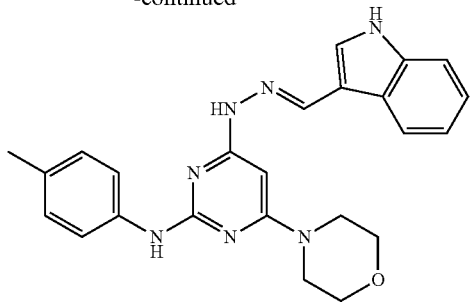

Chemical Synthesis

Step 1

To a solution of 2,4,6-trichloropyrimidine (1.0 g, 5.5 mmol) and morpholine (479 mg, 5.5 mmol) in EtOH (20 mL) was added DIPEA (710 mg, 5.5 mmol) and the reaction was stirred at room temperature for 16 hrs. The reaction solution was concentrated to dryness in vacuum. The residue was purified by silica gel column (PE/EA=50/1) to give 4-(2,6-dichloropyrimidin-4-yl)morpholine (923 mg, yield: 72%) as a white solid. MS: m/z 233.9 (M+H$^+$).

Step 2

To a solution of 4-(2,6-dichloropyrimidin-4-yl)morpholine (500 mg, 2.2 mmol) and p-toluidine (275 mg, 2.6 mmol) in 1,4-dioxane (10 mL) was added conc.HCl (6 drops) and the reaction was heated at 110° C. for 1 hr in a microwave. The reaction mixture was diluted with DCM (20 mL) and the mixture was washed with sat.Na$_2$CO$_3$ (20 mL). The organic phase was concentrated to dryness in vacuum to give the crude 4-chloro-6-morpholino-N-(p-tolyl)pyrimidin-2-amine (760 mg, crude) as a white solid. MS: m/z 305.0 (M+H$^+$).

Step 3

The mixture solution of 4-chloro-6-morpholino-N-(p-tolyl)pyrimidin-2-amine (260 mg, 0.85 mmol) in hydrazine hydrate (10 mL) was stirred for 16 hrs at 100° C. The reaction mixture was poured into H$_2$O (10 mL). The mixture was extracted by EA (10 mL×2). The combined organic layer was washed with brine (10 mL), dried over Na$_2$SO$_4$ and concentrated to give the crude 4-hydrazinyl-6-morpholino-N-(p-tolyl)pyrimidin-2-amine (230 mg, crude) as a white solid.

Step 4

To a solution of 4-hydrazinyl-6-morpholino-N-(p-tolyl)pyrimidin-2-amine (230 mg, 0.85 mmol) in MeOH (20 mL) was added 1H-indole-3-carbaldehyde (123 mg, 0.85 mmol) and the mixture was stirred at 80° C. for 16 hrs. The mixture was concentrated to dryness in vacuum. the residue was purified by prep-HPLC to give (E)-4-(2-((1H-indol-3-yl)methylene)hydrazinyl)-6-morpholino-N-(p-tolyl)pyrimidin-2-amine (17 mg, yield: 5%) as white solid.

$^1$H NMR (400 MHz, CDCl$_3$): δ=8.35-8.24 (m, 3H), 7.94 (s, 1H), 7.44 (d, J=8.4 Hz, 2H), 7.39 (d, J=7.1 Hz, 1H), 7.32-7.23 (m, 3H), 7.10 (d, J=8.4 Hz, 2H), 6.82 (s, 1H), 6.05 (s, 1H), 3.81 (t, J=4.4 Hz, 4H), 3.65 (t, J=4.8 Hz, 4H), 2.30 (s, 3H). MS: m/z 428.0 (M+H$^+$).

Biological Activity

Figure 10:
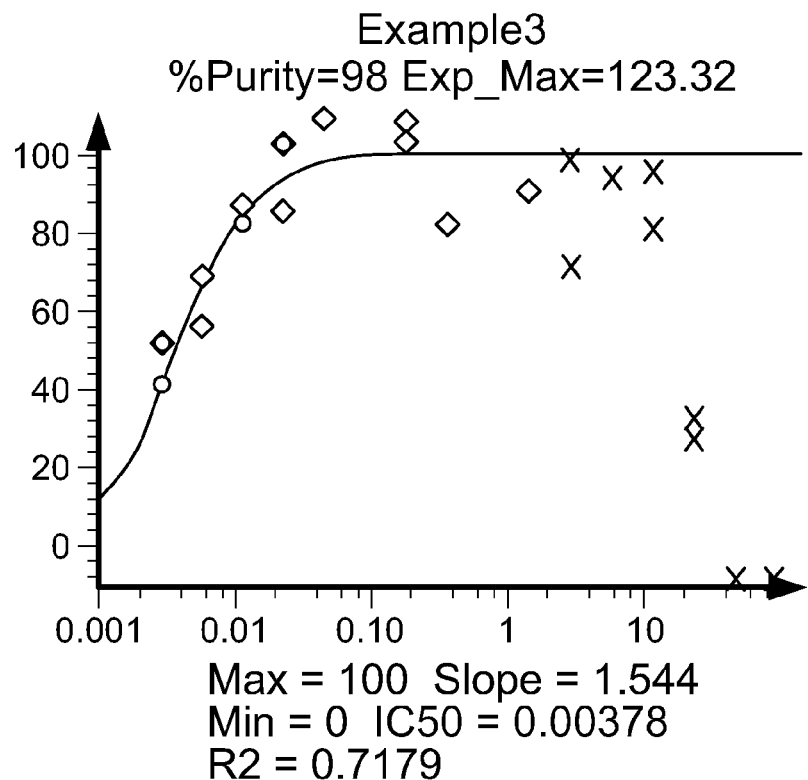
FIG. 10 is a line plot showing activity of Example 3.

See FIG. 10. EC$_{50}$ is 0.004 μM.

Glioblastoma and Colorectal Carcinoma

Figure 11:
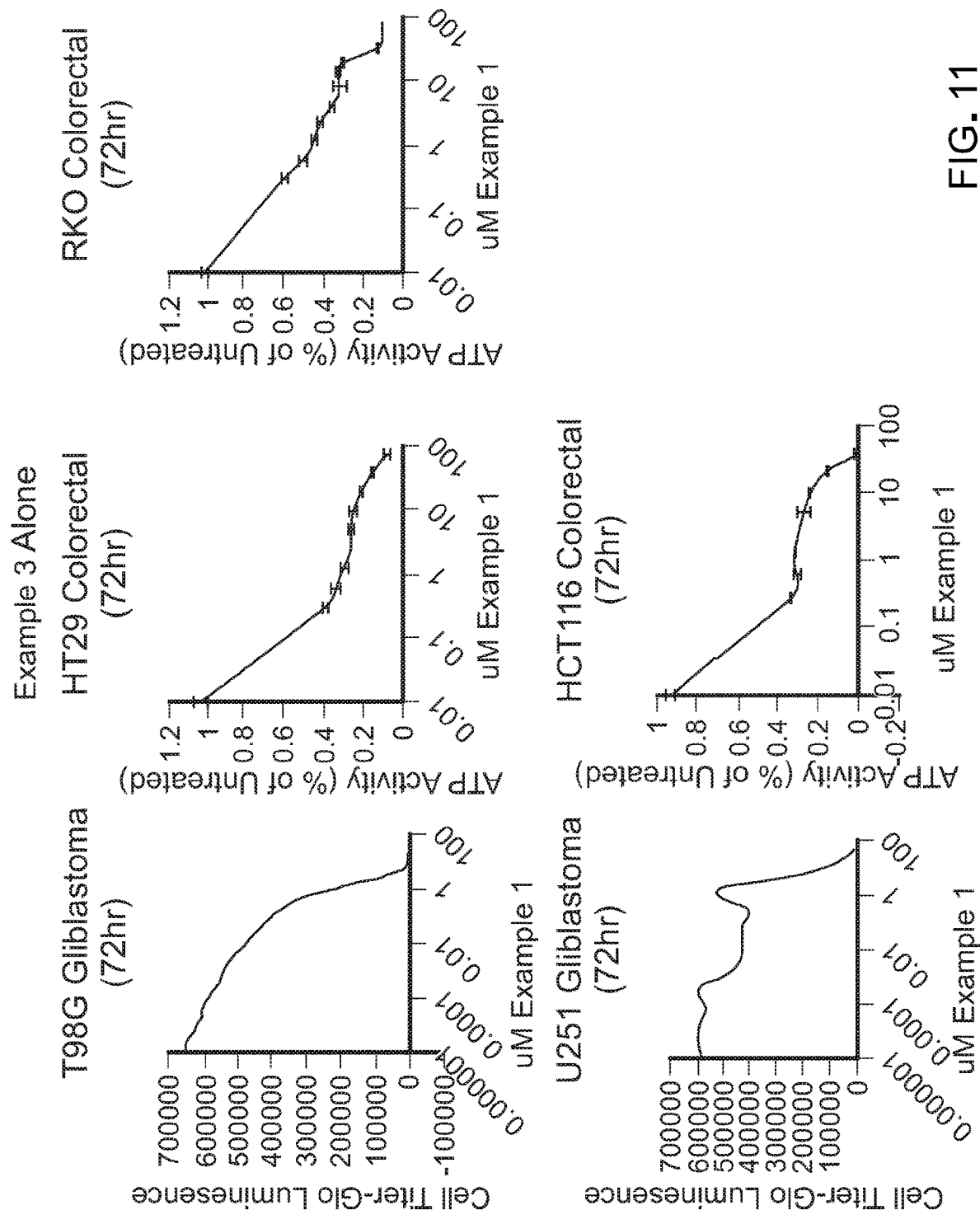
FIG. 11 contains line plots showing that glioblastoma (T98G, U251) or colorectal cancer cell lines (HT29, RKO, HCT116) are sensitive to killing by the compound of Example 3.

Glioblastoma (T98G, U251) or colorectal cancer cell lines (HT29, RKO, HCT116) were also sensitive to killing by the compound. See FIG. 11. Experiments were performed using DMEM-based media for the glioblastoma lines and RMPI-based media for the colorectal lines.

Malignant Peripheral Nerve Sheath Tumor

Figure 26:
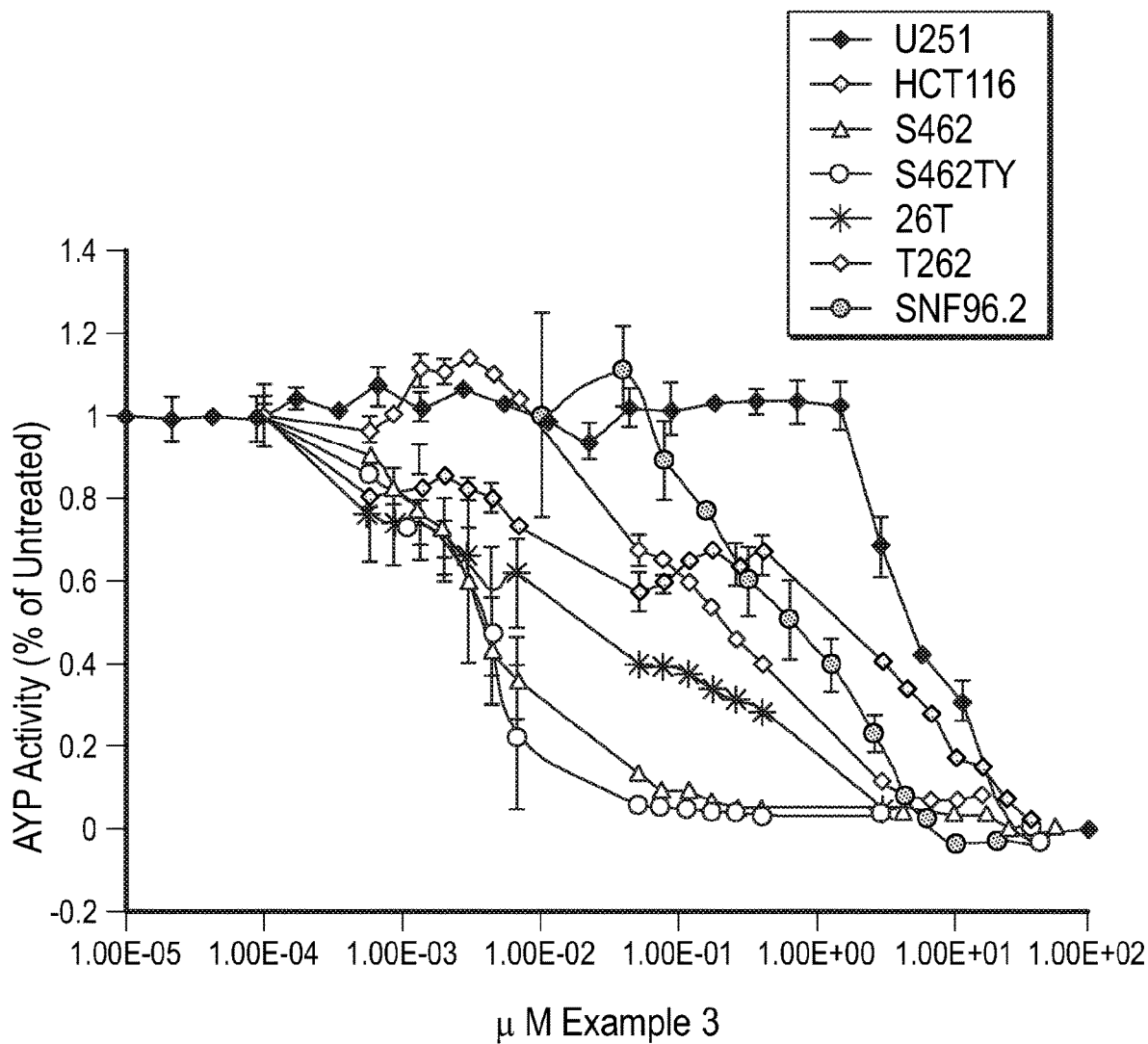
FIG. 26 contains line plots showing cytotoxicity of Example 3 against MPNST cell lines (S462, S462TY, 26T, T265, SNF96.2), a colorectal carcinoma cell line (HCT116), and a GBM line (U251).

Example 3 showed increased efficacy against a tumor type called Malignant Peripheral Nerve Sheath tumor. The form of cell death caused by the compound is consistent with the mechanism known as "methuosis", a non-apoptotic programmed cell death process that has been shown to be caused by hyper-activation of oncogenic RAS. For this reason, it was hypothesized that tumor cells that have activated RAS would have increased sensitivity to this compound. Malignant peripheral nerve sheath tumors (MPNSTs) arise in the population sporadically, and with very high frequency in patients with NF1 mutation. NF1 is a RAS suppressor, and therefore, tumors arising in the NF1-mutant background, have apriori activation of the RAS signaling pathway. MPNST cells lines (S462, S462TY, 26T, T265, SNF96.2) were tested in DMEM-based medium, and were highly sensitive to compound-induced death. See FIG. 26.

PK/PD Characteristics

The compound was further characterized for PK/PD characteristics. The half life after IP injection was approximately 5.5 hours, and the peak concentration was 3268 ng/ml after a single 30 mg/kg dose.

Example 4—Comparative Study to Apilimod

Example 1 and Example 3 are more selective for PIKfyve than is a previously characterized PIKfyve inhibitor apilimod (3-Methylbenzaldehyde 2-[6-(4-Morpholinyl)-2-[2-(2-pyridinyl)ethoxy]-4-pyrimidinyl]hydrazine, CAS Registry No. 541550-19-0):

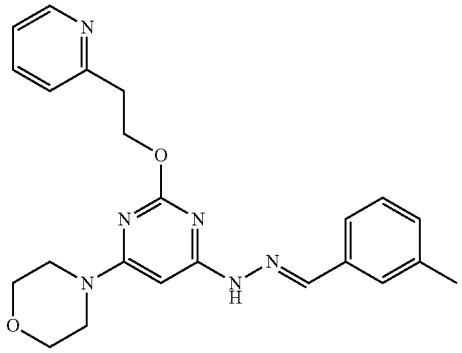 [SMILES: Cc1cccc(/C=N/Nc2cc(N3CCOCC3)nc(OCCc3ccccn3)n2)c1]

Figure 12:
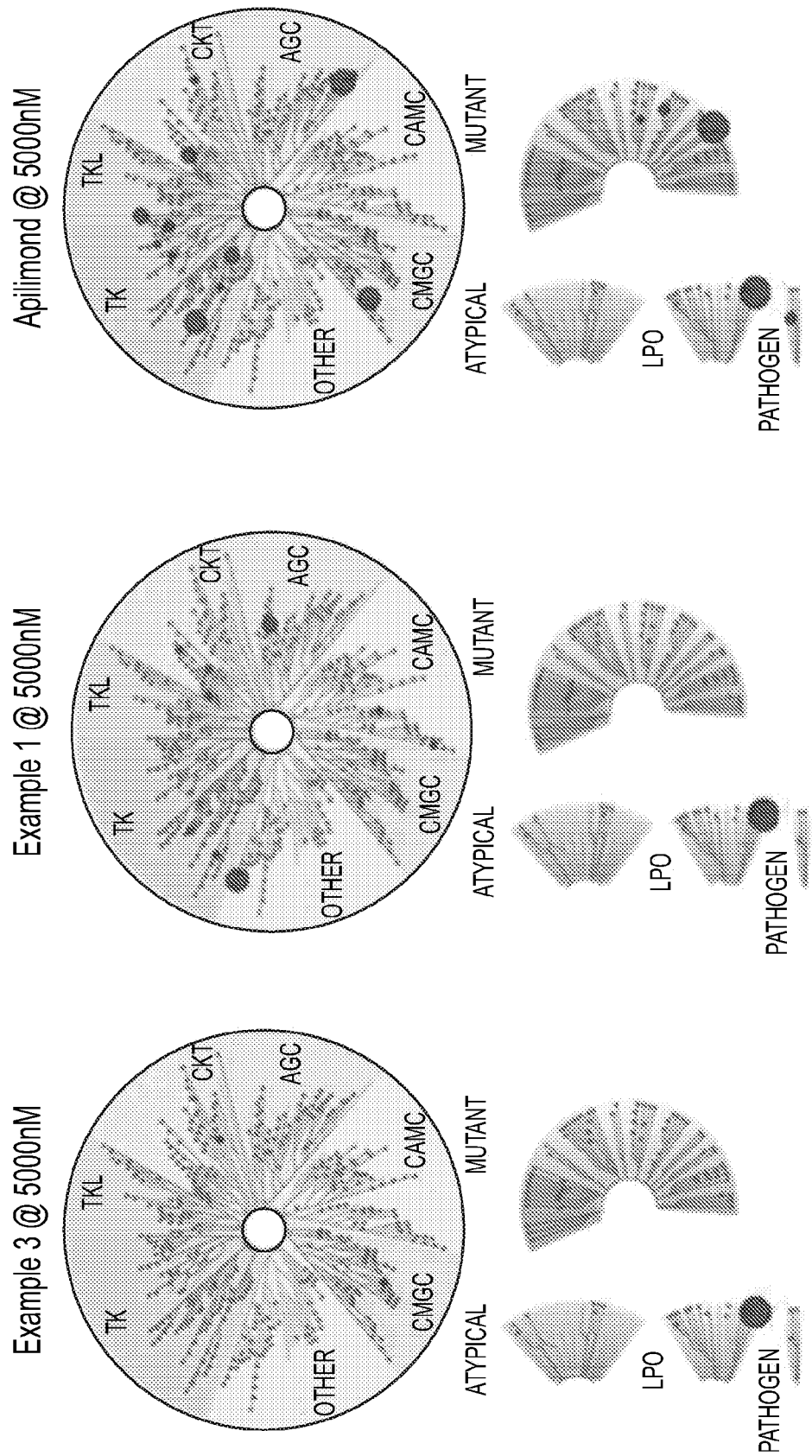
FIG. 12 is a dendrogram showing selective inhibition of PIKfyve by Example 1, Example 3, and inhibition of PIKfyve by apilimod.

At the 50 nM concentration, Example 1 only blocked 1 out of 468 kinases, to less than 1% of controls. It also did not block other kinases to 10% or to 35% of control activity. In contrast, 50 nM Apilimod inhibited two kinases to 1% or 10%, and 3 kinases to 35% of control. To examine non-specific binding at higher concentrations, Example 1, Example 3, and Apilimod were tested at 5000 nM. In these conditions, Example 1 blocked 2, 4, or 11 kinases to the 1%, 10%, or 35% activity levels, while Apilimod was again less specific, blocking 4, 9, and 15 kinases to those three levels. Impressively, Example 3 at 5000 nM only blocked 1, 1, and 4 kinases to the 1%, 10%, and 35% cutoff levels, demonstrating that it has the highest selectivity for PIKfyve of all three compounds. The high selectivity of Example 3 at 5000 nM concentration is demonstrated graphically by the Trees-pot kinase dendrogram, with larger spots indicating higher degrees of inhibition. PIKfyve is represented at the bottom left of each dendrogram. See FIG. 12.

Example 5—Synergism with Vemurafenib

General Methods

A 25 mM stock of vemurafenib (obtained from Selleckchem) in DMSO was diluted to 2× the indicated concentration into the cell suspension immediately prior to plating the cell suspension onto the pre-diluted Example 1 or Example 3, to result in a final 1× concentration of both compounds.

B-RAF inhibitor vemurafenib (N-(3-(5-(4-chlorophenyl)-1H-pyrrolo[2,3-b]pyridine-3-carbonyl)-2,4-difluorophenyl)propane-1-sulfonamide; CAS Registry No. 918504-65-1):

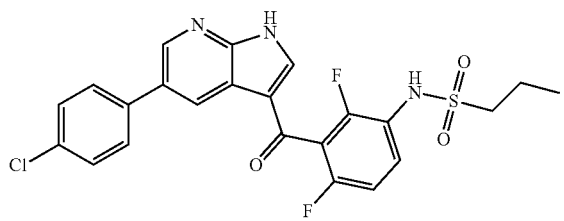 [SMILES: CCCS(=O)(=O)Nc1ccc(F)c(C(=O)c2c[nH]c3ncc(-c4ccc(Cl)cc4)cc23)c1F]

reflexively activates the ras proto-oncogene. Vemurafenib was combined with Example 1 or Example 3 treatment. A dramatic increase in cell death was observed due to the combination of compounds, far in excess of either alone.

Results

Figure 13:
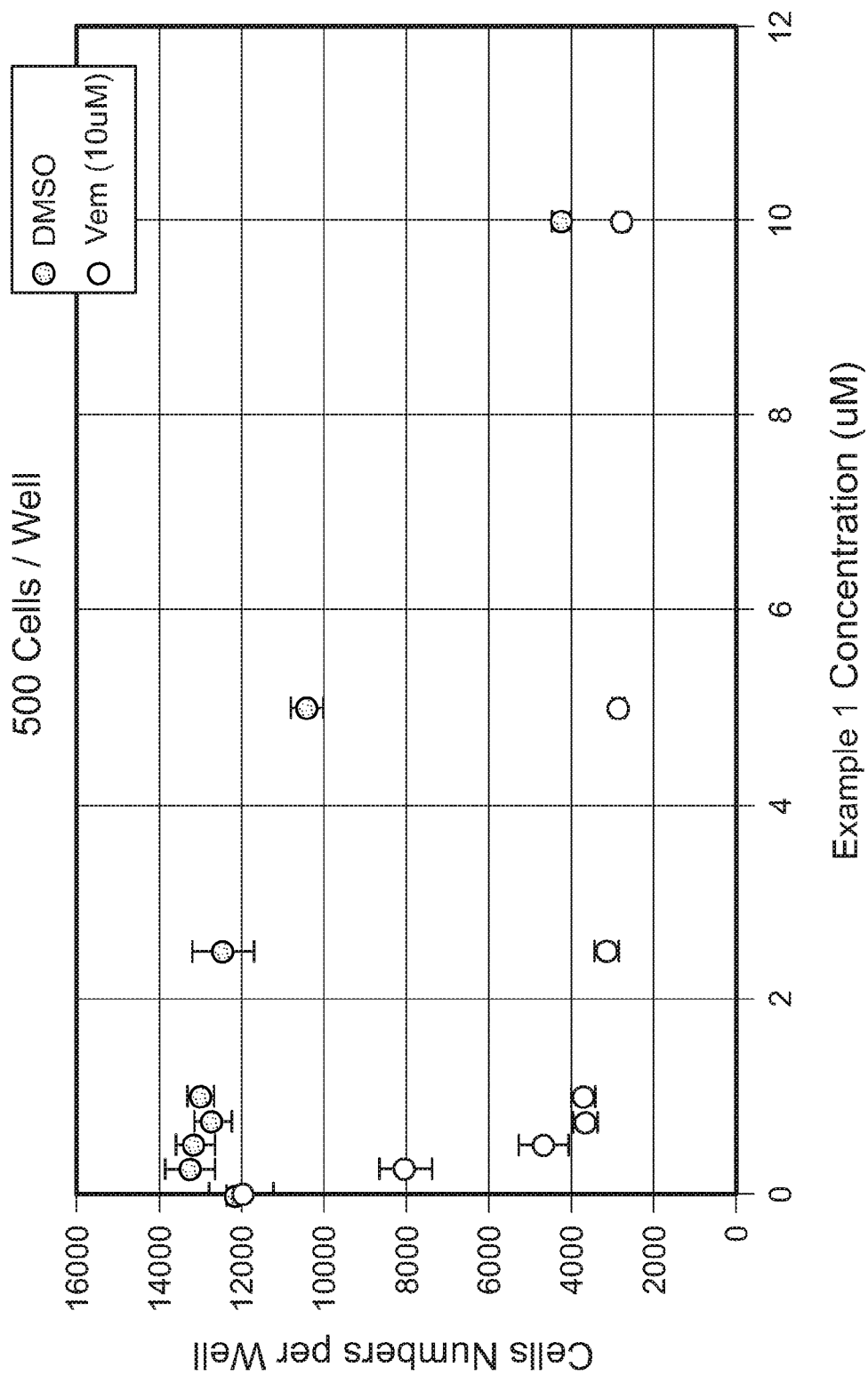
FIG. 13 is a line plot showing U251 glioblastoma cell killing by Example 1 alone or in the presence of 10 µM vemurafenib.

See FIG. 13 for showing of U251 glioblastoma cell killing by Example 1 alone or in the presence of 10 µM vemurafenib over a 72 hour time course. Note that at 0 µM Example 1 (left-most points) there is little effect of vemurafenib, but at low concentrations of Example 1 (e.g., 0.5 µM), the addition of vemurafenib significantly improves cell killing.

Figure 14:
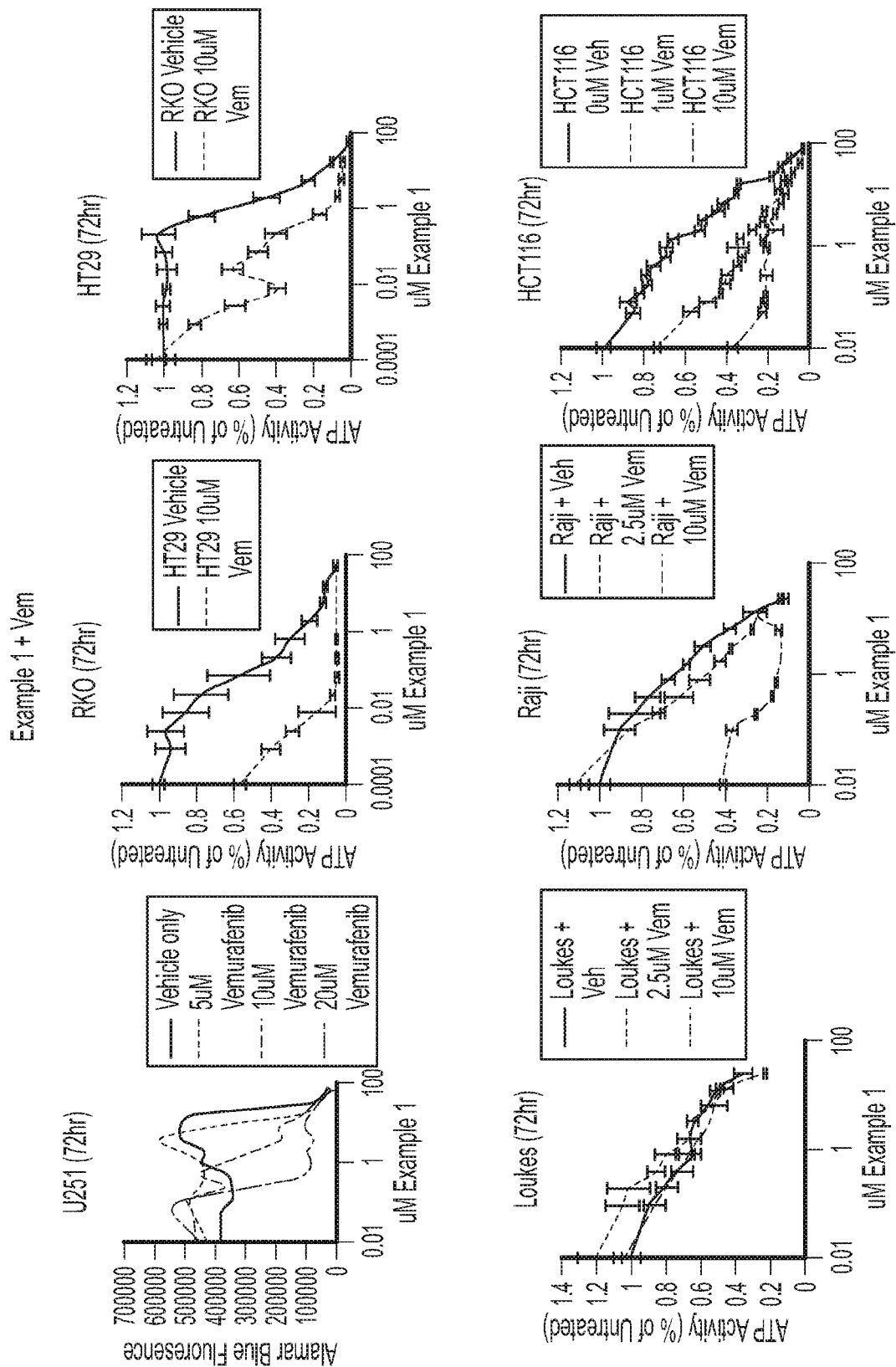
FIG. 14 contains line plots showing synergistic cell killing by the combination of vemurafenib with various concentrations of Example 1.
Figure 15:
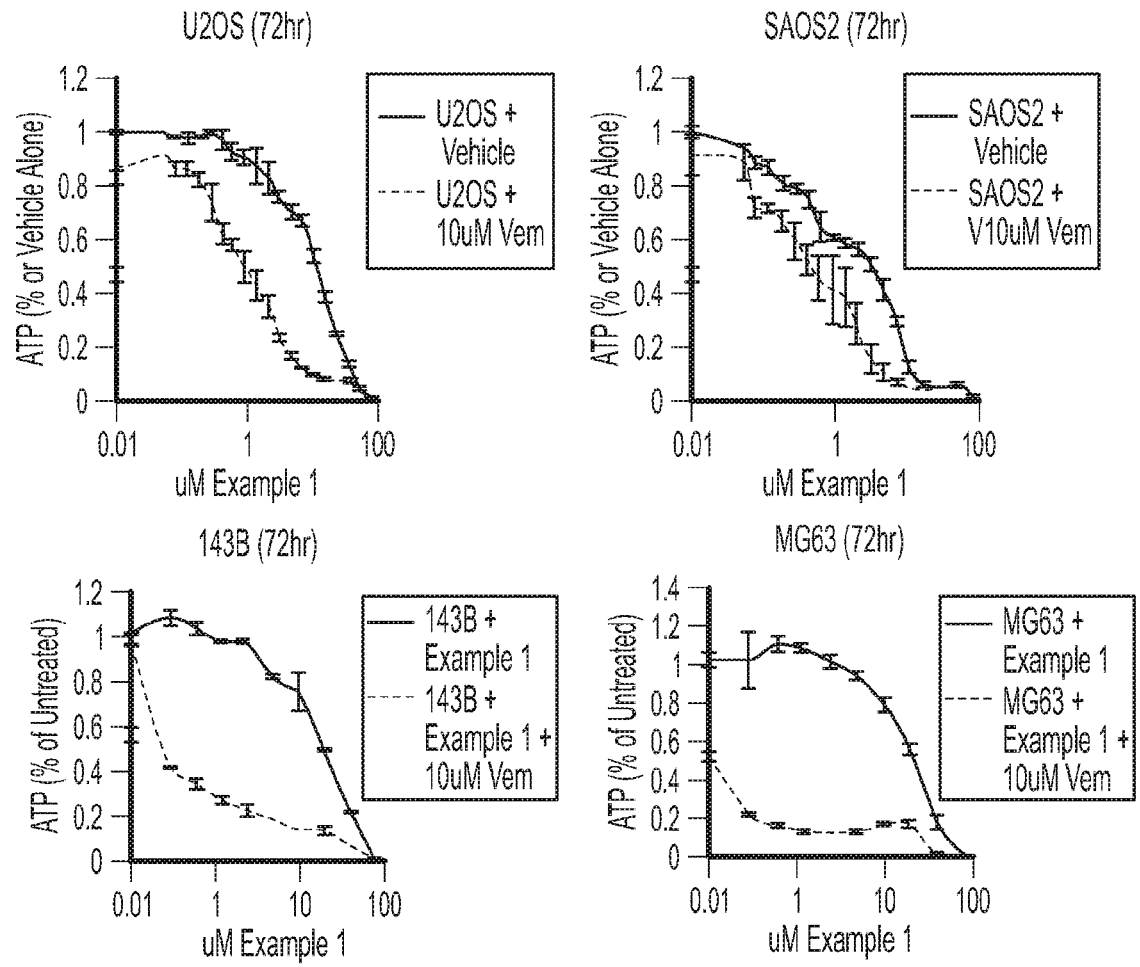
FIG. 15 contains line plots showing synergistic cell killing by the combination of vemurafenib with various concentrations of Example 1.

More examples of synergistic cell killing by the combination of vemurafenib with various concentrations of Example 1 are shown in FIG. 14 and FIG. 15, for the indicated cell types.

Figure 16:
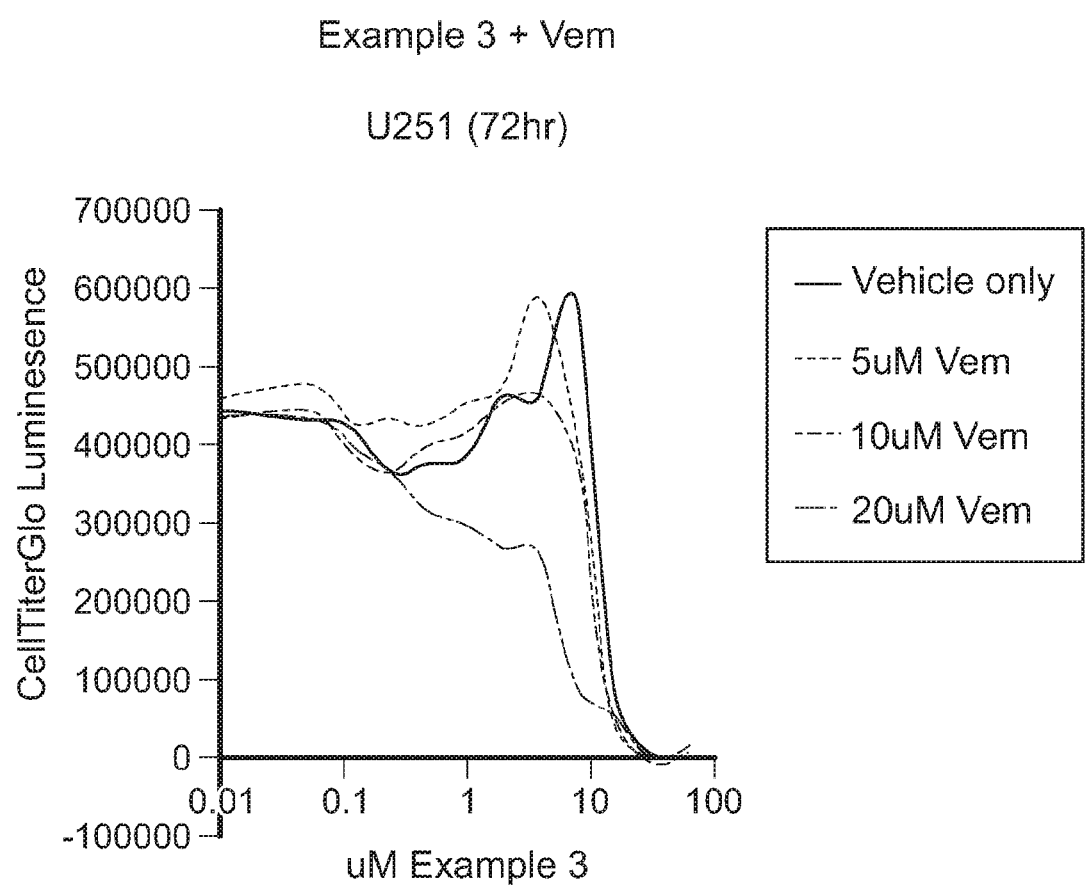
FIG. 16 is a line plot showing that Example 3 is synergistic with vemurafenib in killing U25.

As shown in FIG. 16, Example 3 is also synergistic with vemurafenib in killing U251.

Example 6—Pharmacokinetic and Pharmacodynamics Study of Compound of Example 1

Species: Male C57BL/6 Mouse, fasted.

Figure 8:
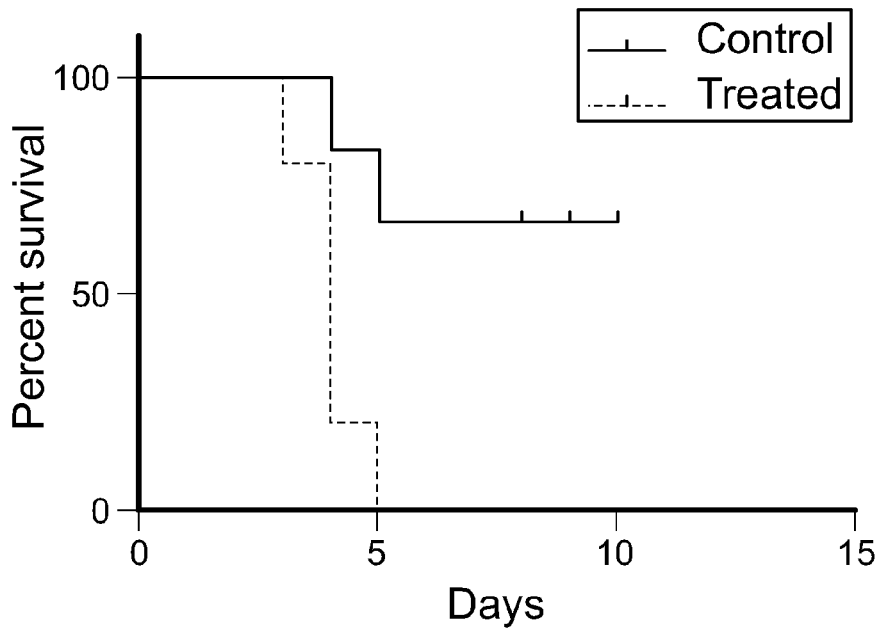
FIG. 8 contains a line plot showing PK/PD testing of the compound of Example 1 in mice, after IP, IV, or oral administration.

PK/PD testing of the compound was performed in mice, after IP, IV, or oral administration. See FIG. 8. IP dosing gave the following kinetics, with a half life of 10.1 hours, and a peak concentration of 534 ng/ml after a single 30 mg/kg dose.

Nude mice were injected in the flank with 1 million E2409 murine lymphoma cells, and allowed to grow for 4 days, at which point a small detectable lump was observed on each mouse. Mice were injected daily by IP injection with 100 µl of vehicle (10% dmso, 20% cremaphor, 70% water) with or without 1 mg of the test compound. Mice were euthanized when tumor size exceeded 1500 mm$^3$. Treated mice had prolonged survival compared to vehicle only treated mice ($p<0.02$).

TABLE 1

| | Administered doses | | |
|---|---|---|---|
| | IV | IP | PO |
| Nominal dose (mg/kg) | 5.00 | 30.0 | 30.0 |
| Administered dose (mg/kg) | 4.75 | 28.5 | 28.5 |

TABLE 2

| | Composition of dosages |
|---|---|
| IV | 5 mg/mL in 75% PEG400/25% water, clear solution |
| IP | 6 mg/mL in 0.5% MC/0.2% Tween80 in water, opaque homogenous suspension |
| PO | 6 mg/mL in 0.5% MC/0.2% Tween80 in water, opaque homogenous suspension |

Figure 17:
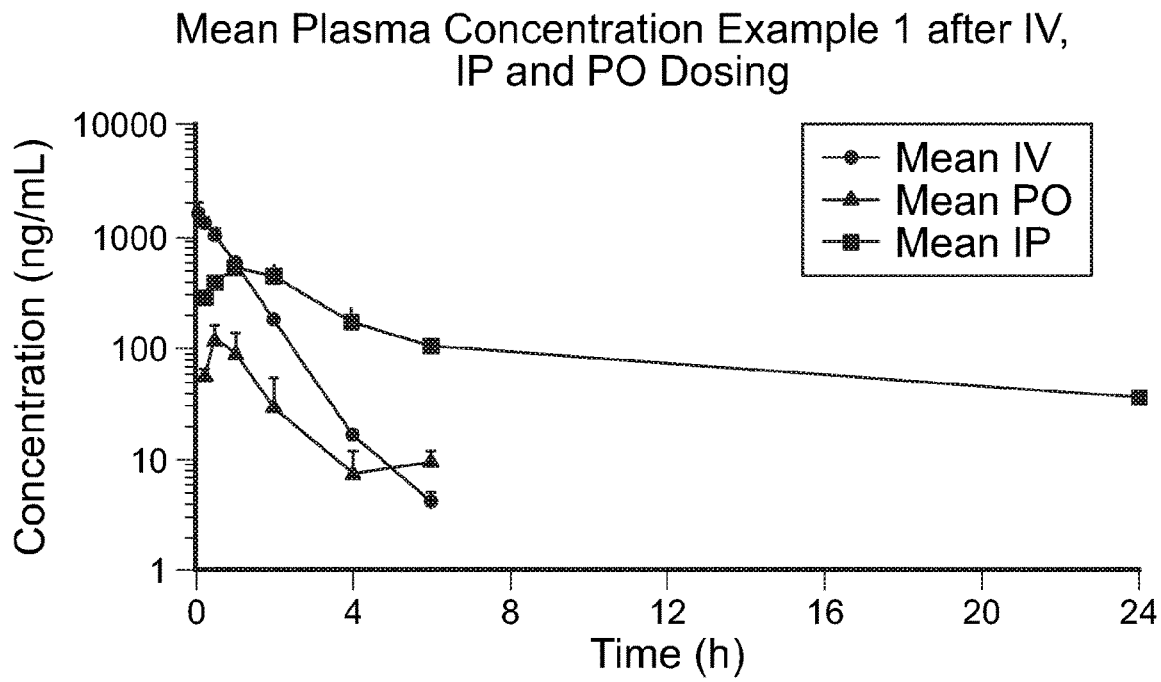
FIG. 17 is a line plot showing mean plasma concentration of Example 1 after IV, IP and PO dosing in mice.
Figure 18:
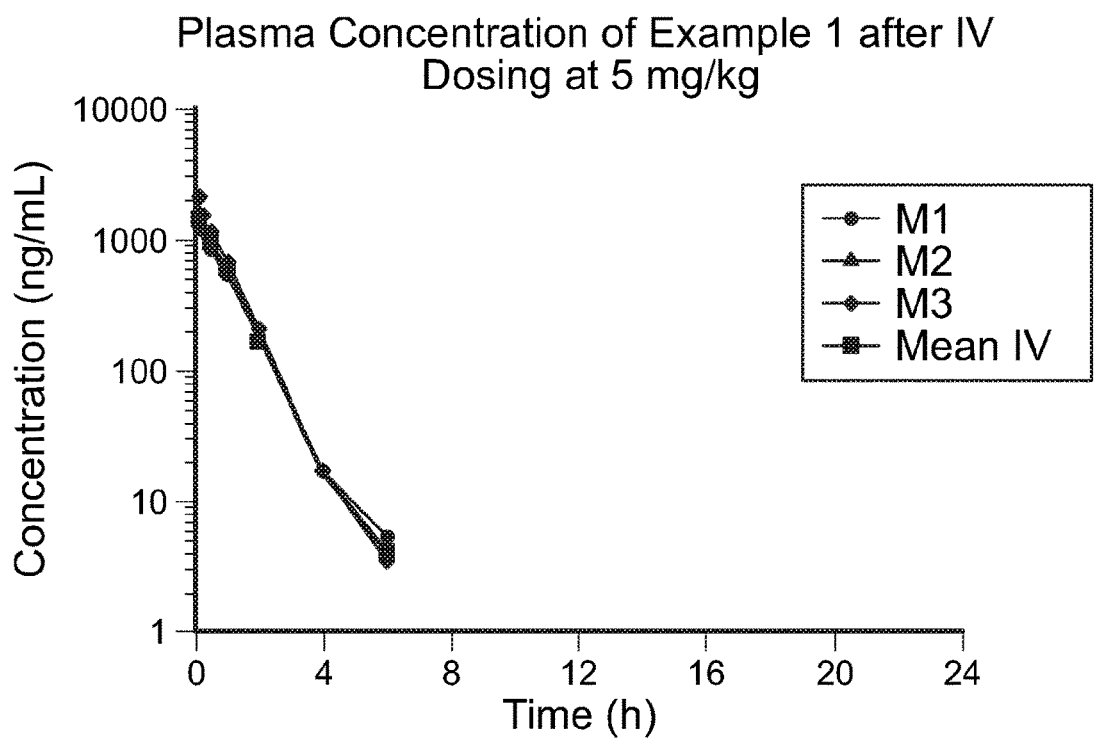
FIG. 18 is a line plot showing plasma concentration of Example 1 after IV dosing at 5 mg/kg.
Figure 19:
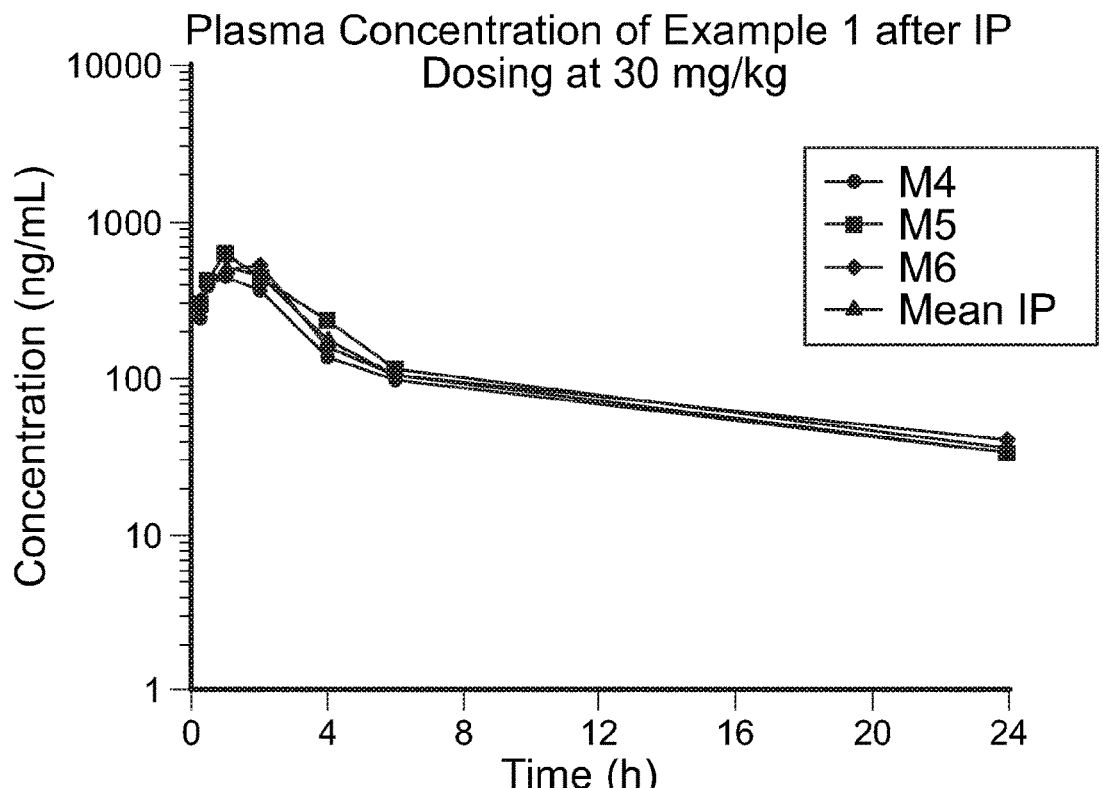
FIG. 19 is a line plot showing plasma concentration of Example 1 after IP dosing at 30 mg/kg in mice.
Figure 20:
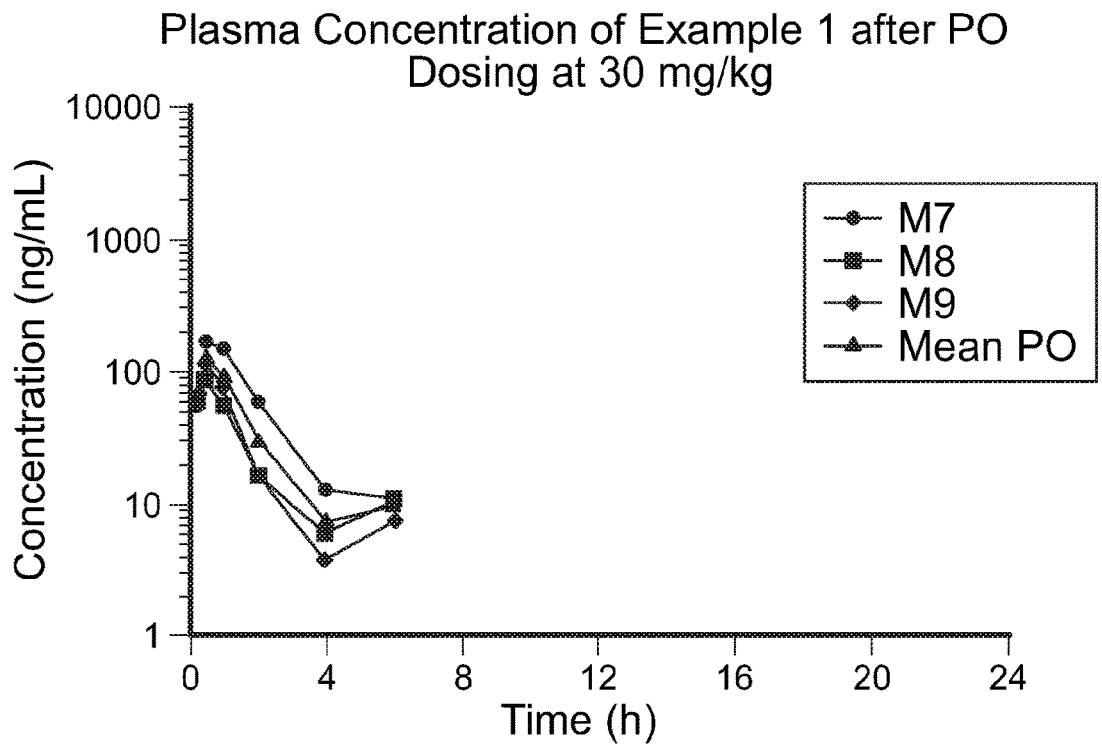
FIG. 20 is a line plot showing plasma concentration of Example 1 after PO dosing at 30 mg/kg in mice.

FIG. 17 shows mean plasma concentration of Example 1 after IV, IP and PO dosing. FIGS. 18, 19 and 20 show plasma concentration of Example 1 after IV dosing at 5 mg/kg, IP dosing at 30 mg/kg, and PO dosing at 30 mg/kg, respectively.

TABLE 3

Bioavailability of Example 1 in mouse, IV at 5 mg/kg, plasma (ng/mL).

| | M1 | M2 | M3 | Mean IV | ± | SD | CV (%) |
|---|---|---|---|---|---|---|---|
| IV Time (h) | | | | | | | |
| 0.0833 | 1300 | 1500 | 2090 | 1630 | ± | 411 | 25.2 |
| 0.250 | 1140 | 1270 | 1530 | 1313 | ± | 199 | 15.1 |
| 0.500 | 832 | 1060 | 1130 | 1007 | ± | 156 | 15.5 |
| 1.00 | 529 | 591 | 678 | 599 | ± | 74.8 | 12.5 |
| 2.00 | 176 | 169 | 204 | 183 | ± | 18.5 | 10.1 |
| 4.00 | 17.4 | 16.7 | 16.4 | 16.8 | ± | 0.513 | 3.05 |
| 6.00 | 5.13 | 4.04 | 3.44 | 4.20 | ± | 0.857 | 20.4 |
| 24.0 | BQL | BQL | BQL | ND | ± | ND | ND |
| PK Parameters | | | | | | | |
| Rsq_adj | 0.988 | 0.990 | 0.992 | — | ± | — | — |
| No. points used for $T_{1/2}$ | 7.00 | 7.00 | 7.00 | 7.00 | ± | — | — |
| $C_0$ (ng/mL) | 1388 | 1630 | 2442 | 1820 | ± | 552 | 30.3 |
| $T_{1/2}$ (h) | 0.710 | 0.665 | 0.628 | 0.667 | ± | 0.0410 | 6.15 |
| $Vd_{ss}$ (L/kg) | 3.48 | 2.89 | 2.32 | 2.90 | ± | 0.580 | 20.0 |
| Cl (mL/min/kg) | 60.5 | 54.0 | 45.7 | 53.4 | ± | 7.42 | 13.9 |
| $T_{last}$ (h) | 6.00 | 6.00 | 6.00 | 6.00 | ± | — | — |
| $AUC_{0-last}$ (ng · h/mL) | 1372 | 1539 | 1820 | 1577 | ± | 227 | 14.4 |
| $AUC_{0-inf}$ (ng · h/mL) | 1377 | 1543 | 1823 | 1581 | ± | 225 | 14.3 |
| $MRT_{0-last}$ (h) | 0.936 | 0.875 | 0.836 | 0.882 | ± | 0.0502 | 5.69 |
| $MRT_{0-inf}$ (h) | 0.959 | 0.890 | 0.847 | 0.899 | ± | 0.0567 | 6.31 |

TABLE 3-continued

Bioavailability of Example 1 in mouse, IV at 5 mg/kg, plasma (ng/mL).

| | M1 | M2 | M3 | Mean IV | | SD | CV (%) |
|---|---|---|---|---|---|---|---|
| AUC$_{Extra}$ (%) | 0.381 | 0.251 | 0.171 | 0.268 | ± | 0.106 | 39.7 |
| AUMC$_{Extra}$ (%) | 2.79 | 1.96 | 1.39 | 2.05 | ± | 0.704 | 34.3 |

TABLE 4

Bioavailability of Example 1 in mouse, IP at 30 mg/kg, plasma (ng/mL).

| | M4 | M5 | M6 | Mean IP | | SD | CV (%) |
|---|---|---|---|---|---|---|---|
| IP Time (h) | | | | | | | |
| 0.250 | 242 | 299 | 314 | 285 | ± | 38.0 | 13.3 |
| 0.500 | 381 | 430 | 376 | 396 | ± | 29.8 | 7.54 |
| 1.00 | 443 | 636 | 492 | 524 | ± | 100 | 19.2 |
| 2.00 | 367 | 441 | 523 | 444 | ± | 78.0 | 17.6 |
| 4.00 | 136 | 232 | 158 | 175 | ± | 50.3 | 28.7 |
| 6.00 | 97.8 | 115 | 103 | 105 | ± | 8.82 | 8.38 |
| 24.0 | 35.0 | 34.1 | 40.7 | 36.6 | ± | 3.58 | 9.78 |
| PK Parameters | | | | | | | |
| Rsq_adj | 0.959 | 0.848 | 0.902 | — | ± | — | — |
| No. points used for T$_{1/2}$ | 3.00 | 3.00 | 3.00 | 3.00 | ± | — | — |
| C$_{max}$ (ng/mL) | 443 | 636 | 523 | 534 | ± | 97.0 | 18.2 |
| T$_{max}$ (h) | 1.00 | 1.00 | 2.00 | 1.33 | ± | 0.577 | 43.3 |
| T$_{1/2}$ (h) | 10.9 | 8.19 | 11.3 | 10.1 | ± | 1.69 | 16.7 |
| T$_{last}$ (h) | 24.0 | 24.0 | 24.0 | 24.0 | ± | — | — |
| AUC$_{0-last}$ (ng · h/mL) | 2515 | 3110 | 2925 | 2850 | ± | 304 | 10.7 |
| AUC$_{0-inf}$ (ng · h/mL) | 3065 | 3512 | 3588 | 3388 | ± | 282 | 8.33 |
| MRT$_{0-last}$ (h) | 7.20 | 6.56 | 6.98 | 6.91 | ± | 0.325 | 4.71 |
| MRT$_{0-inf}$ (h) | 13.0 | 9.91 | 13.1 | 12.0 | ± | 1.83 | 15.2 |
| AUC$_{Extra}$ (%) | 18.0 | 11.5 | 18.5 | 16.0 | ± | 3.90 | 24.5 |
| AUMC$_{Extra}$ (%) | 54.7 | 41.4 | 56.7 | 50.9 | ± | 8.29 | 16.3 |
| Bioavailability (%)[a] | — | — | — | 35.7 | ± | — | — |

TABLE 5

Bioavailability of Example 1 in mouse, PO at 30 mg/kg, plasma (ng/mL).

| | M7 | M8 | M9 | Mean PO | | SD | CV (%) |
|---|---|---|---|---|---|---|---|
| PO Time (h) | | | | | | | |
| 0.250 | 52.7 | 59.6 | 65.0 | 59.1 | ± | 6.17 | 10.4 |
| 0.500 | 167 | 84.2 | 115 | 122 | ± | 41.8 | 34.3 |
| 1.00 | 145 | 55.8 | 75.3 | 92.0 | ± | 46.9 | 51.0 |
| 2.00 | 58.6 | 16.2 | 16.7 | 30.5 | ± | 24.3 | 79.8 |
| 4.00 | 12.7 | 5.98 | 3.78 | 7.49 | ± | 4.65 | 62.1 |
| 6.00 | 11.0 | 11.3 | 7.80 | 10.0 | ± | 1.94 | 19.3 |
| 24.0 | BQL | BQL | BQL | ND | ± | ND | ND |
| PK Parameters | | | | | | | |
| Rsq_adj | 0.829 | 0.549 | 0.400 | — | ± | — | — |
| No. points used for T$_{1/2}$ | 4.00 | 5.00 | 4.00 | ND | ± | — | — |
| C$_{max}$ (ng/mL) | 167 | 84.2 | 115 | 122 | ± | 41.8 | 34.3 |
| T$_{max}$ (h) | 0.500 | 0.500 | 0.500 | 0.500 | ± | 0 | 0.0 |
| T$_{1/2}$ (h) | 1.31 | 1.76 | 1.55 | 1.54 | ± | 0.221 | 14.4 |
| T$_{last}$ (h) | 6.00 | 6.00 | 6.00 | 6.00 | ± | — | — |
| AUC$_{0-last}$ (ng · h/mL) | 291 | 129 | 145 | 188 | ± | 89.2 | 47.4 |
| AUC$_{0-inf}$ (ng · h/mL) | 312 | 158 | 162 | 211 | ± | 87.6 | 41.6 |
| MRT$_{0-last}$ (h) | 1.69 | 1.72 | 1.41 | 1.61 | ± | 0.172 | 10.7 |
| MRT$_{0-inf}$ (h) | 2.10 | 2.96 | 2.14 | 2.40 | ± | 0.483 | 20.1 |
| AUC$_{Extra}$ (%) | 6.68 | 18.1 | 10.7 | 11.9 | ± | 5.81 | 49.0 |

TABLE 5-continued

Bioavailability of Example 1 in mouse, PO at 30 mg/kg, plasma (ng/mL).

| | M7 | M8 | M9 | Mean PO | | SD | CV (%) |
|---|---|---|---|---|---|---|---|
| AUMC$_{Extra}$ (%) | 25.1 | 52.3 | 41.3 | 39.6 | ± | 13.7 | 34.6 |
| Bioavailability (%)[a] | — | — | — | 2.22 | ± | — | — |

ND = Not determined (Parameters not determined due to inadequately defined terminal elimination phase).
BQL = Below the lower limit of quantitation (LLOQ). If the adjusted rsq (linear regression coefficient of the concentration value on the terminal phase) is less than 0.9, T½ might not be accurately estimated. If the % AUC$_{Extra}$ > 20%, AUC$_{0-inf}$ Cl, MRT$_{0-inf}$ and Vd$_{ss}$ might not be accurately estimated. If the % AUMC$_{Extra}$ >20%, MRT$_{0-inf}$ and Vd$_{ss}$ might not be accurately estimated. The adjusted linear regression coefficient of the concentration value on the terminal phase is less than 0.9, T$_{1/2}$ might not be accurately estimated,
[a]Bioavailability (%) was calculated using AUC$_{0-inf}$ (% AUC$_{Extra}$ <20%) or AUC$_{0-last}$ (% AUC$_{Extra}$ >20%) with nominal dose.

Example 7—Pharmacokinetic and Pharmacodynamics Study of Compound of Example 3

Species: C57 Mouse. Dose Route: IV&IP. Formulation Vehicle: IV&IP: 10% DMSO/30% PEG400/60% Saline. Dose Level: IV (5 mg/kg) and IP (30 mg/kg). Dose Volume: IV (5 mL/kg) and IP (10 mL/kg). Formulation concentrations: IV (1 mg/mL) and IP (3 mg/mL). LLOQ: IV (2 ng/mL) and IP (10 ng/mL).

Figure 21:
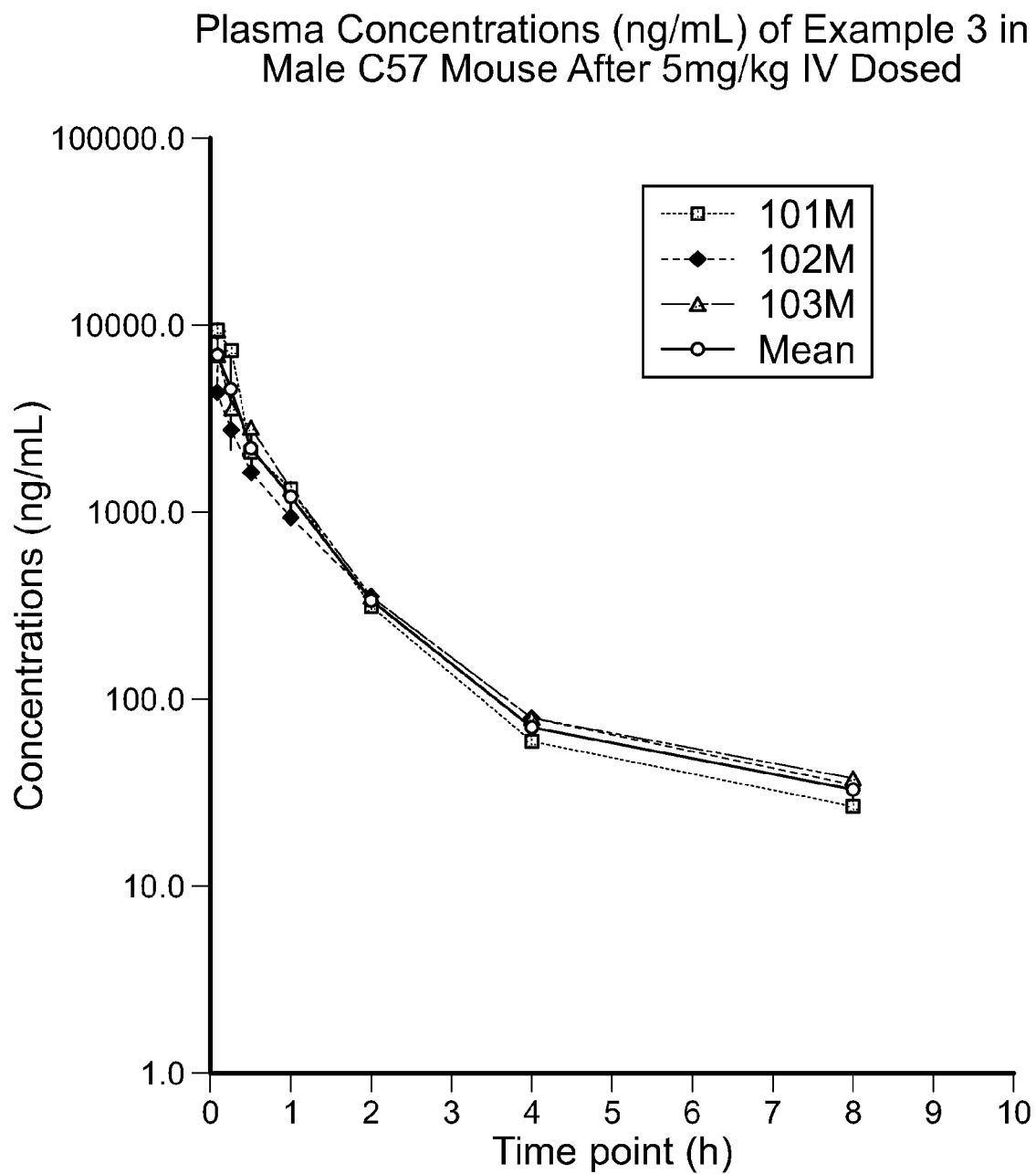
FIG. 21 is a line plot showing plasma concentrations (ng/mL) of Example 3 in male C57 mouse after 5 mg/kg IV dosed.
Figure 22:
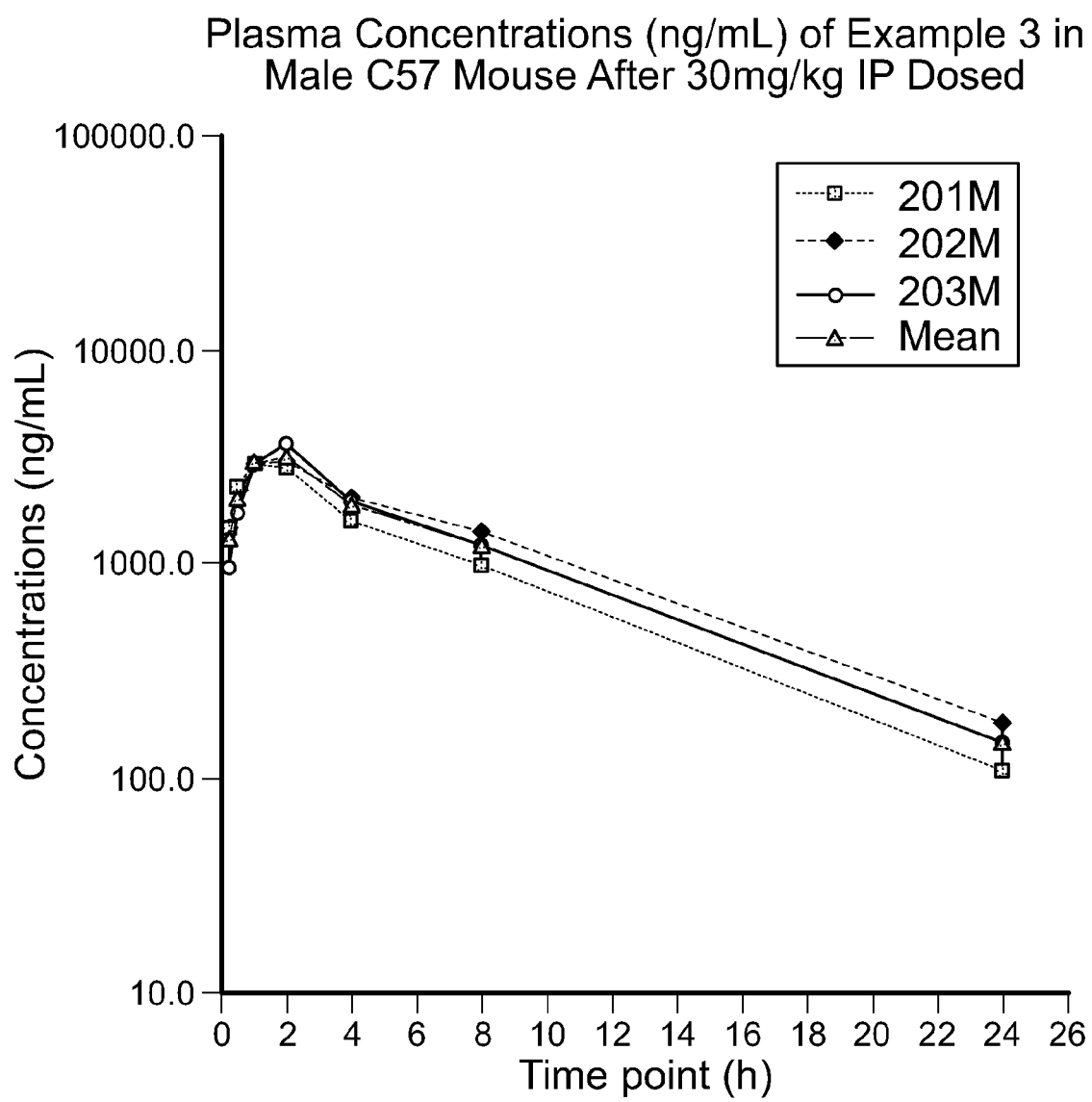
FIG. 22 is a line plot showing plasma concentrations (ng/mL) of Example 3 in male C57 mouse after 30 mg/kg IP dosed.

FIGS. 21 and 22 show plasma concentrations (ng/mL) of Example 3 in male C57 mouse after 5 mg/kg IV dosed, and after 30 mg/kg IP dosed, respectively.

TABLE 6

Plasma concentrations (ng/mL) and PK parameters of Example 3 in male C57 mouse after 5 mg/kg IV dosed.

| Time point | Animal Study No. | | | | |
|---|---|---|---|---|---|
| (Hours) | 101M | 102M | 103M | Mean | SD |
| 0.08 | 9197.2 | 4387.4 | 7116.5 | 6900.4 | 2412.2 |
| 0.25 | 7195.4 | 2758.6 | 3627.2 | 4527.1 | 2351.3 |
| 0.50 | 2078.6 | 1641.4 | 2830.9 | 2183.6 | 601.7 |
| 1.00 | 1346.4 | 944.6 | 1358.7 | 1216.6 | 235.6 |
| 2.00 | 308.7 | 355.3 | 348.7 | 337.6 | 25.2 |
| 4.00 | 59.0 | 71.0 | 80.3 | 70.1 | 10.7 |
| 8.00 | 26.5 | 35.2 | 37.8 | 33.2 | 5.9 |
| 24.00 | BLQ | BLQ | BLQ | NA | NA |
| HL_Lambda_z (T$_{1/2}$, h) | 0.85 | 0.98 | 0.85 | 0.89 | 0.07 |
| C$_{max}$ (ng/ml) | 9197.2 | 4387.4 | 7116.5 | 6900.4 | 2412.2 |
| AUC$_{last}$ (h * ng/ml) | 5478.7 | 3387.7 | 4862.4 | 4576.3 | 1074.5 |
| AUC$_{INF\_pred}$ (h * ng/ml) | 5500.9 | 3424.1 | 4892.0 | 4605.7 | 1067.6 |
| MRT$_{last}$ (h) | 0.63 | 0.90 | 0.77 | 0.76 | 0.14 |
| Vz$_{pred}$ (L/kg) | 1.12 | 2.06 | 1.25 | 1.48 | 0.51 |
| Cl$_{pred}$ (L/h/kg) | 0.91 | 1.46 | 1.02 | 1.13 | 0.29 |
| λz Calculation Time Range (h) | 0.5-8 | 0.5-8 | 0.25-8 | NA | NA |

TABLE 7

Plasma concentrations (ng/mL) and PK parameters of Example 3 in male C57 mouse after 30 mg/kg IP dosed.

| Time point | Animal Study No. | | | | |
|---|---|---|---|---|---|
| (Hours) | 201M | 202M | 203M | Mean | SD |
| 0.25 | 1488.4 | 1507.7 | 971.3 | 1322.5 | 304.3 |
| 0.50 | 2268.9 | 2007.7 | 1751.8 | 2009.5 | 258.6 |
| 1.00 | 2987.1 | 3178.8 | 2919.1 | 3028.3 | 134.7 |
| 2.00 | 2833.0 | 3158.8 | 3638.0 | 3209.9 | 404.9 |
| 4.00 | 1604.9 | 2115.5 | 1962.2 | 1894.2 | 262.0 |
| 8.00 | 998.1 | 1428.1 | 1227.0 | 1217.7 | 215.1 |
| 24.00 | 107.0 | 185.0 | 145.1 | 145.7 | 39.0 |
| HL_Lambda_z (T$_{1/2}$, h) | 5.29 | 5.85 | 5.52 | 5.55 | 0.28 |
| T$_{max}$ (h) | 1.00 | 1.00 | 2.00 | 1.33 | 0.58 |
| C$_{max}$ (ng/ml) | 2987.1 | 3178.8 | 3638.0 | 3268.0 | 334.5 |
| AUC$_{last}$ (h * ng/ml) | 21866.6 | 28429.1 | 26046.4 | 25447.4 | 3322.0 |
| AUC$_{INF\_pred}$ (h * ng/ml) | 22674.8 | 29976.8 | 27188.2 | 26613.3 | 3684.8 |
| MRT$_{last}$ (h) | 4.90 | 5.45 | 5.15 | 5.17 | 0.28 |
| Vz$_{F\_pred}$ (L/kg) | 10.11 | 8.44 | 8.78 | 9.11 | 0.88 |
| Cl$_{F\_pred}$ (L/h/kg) | 1.32 | 1.00 | 1.10 | 1.14 | 0.16 |
| λz Calculation Time Range (h) | 4-24 | 4-24 | 4-24 | NA | NA |
| F % | 79.64 | 103.54 | 94.86 | 92.68 | 12.10 |

Example 8—N-(1H-Indol-3-ylmethyl)-6-morpholin-4-yl-N'-p-tolyl-[1,3,5]triazine-2,4-diamine

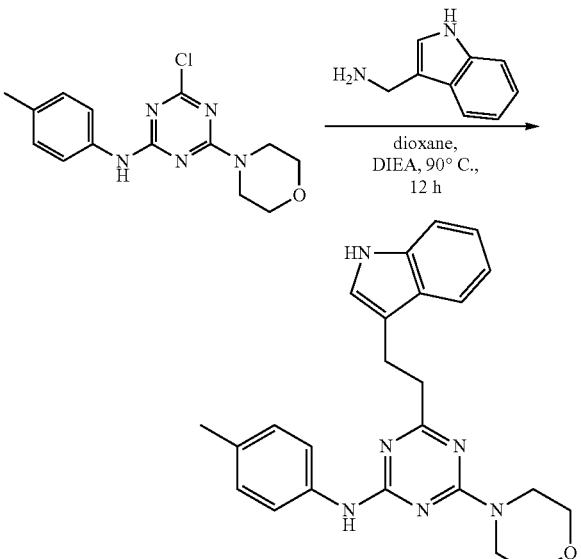

To a solution of (4-chloro-6-morpholin-4-yl-[1,3,5]triazin-2-yl)-p-tolyl-amine (100 mg, 0.32 mmol) in dioxane (20 mL) was added (1H-indol-3-yl)methanamine (187 mg, 1.28 mmol) and DIEA (82.56 mg, 0.64 mmol) and the mixture was stirred at 90° C. for 12 hrs. The reaction was monitored by LCMS. The mixture was concentrated in vacuum to give residue, which was purified by column chromatography followed by prep-HPLC purification to afford N-(1H-Indol-3-ylmethyl)-6-morpholin-4-yl-N'-p-tolyl-[1,3,5]triazine-2,4-diamine (37 mg, yield: 27%) as a white solid.

$^1$H NMR (400 MHz, DMSO-d6): δ=10.83 (s, 1H), 8.99-8.74 (m, 1H), 7.68-7.55 (m, 3H), 7.33 (d, J=8.0 Hz, 1H), 7.27-7.14 (m, 2H), 7.09-6.93 (m, 4H), 4.62 (s, 2H), 3.81-3.55 (m, 8H), 2.21 (s, 3H). MS: m/z 416.0 (M+H$^+$).

Example 9—{4-[N'-(1H-Indol-3-ylmethylene)-hydrazino]-6-morpholin-4-yl-[1,3,5]triazin-2-yl}-m-tolyl-amine

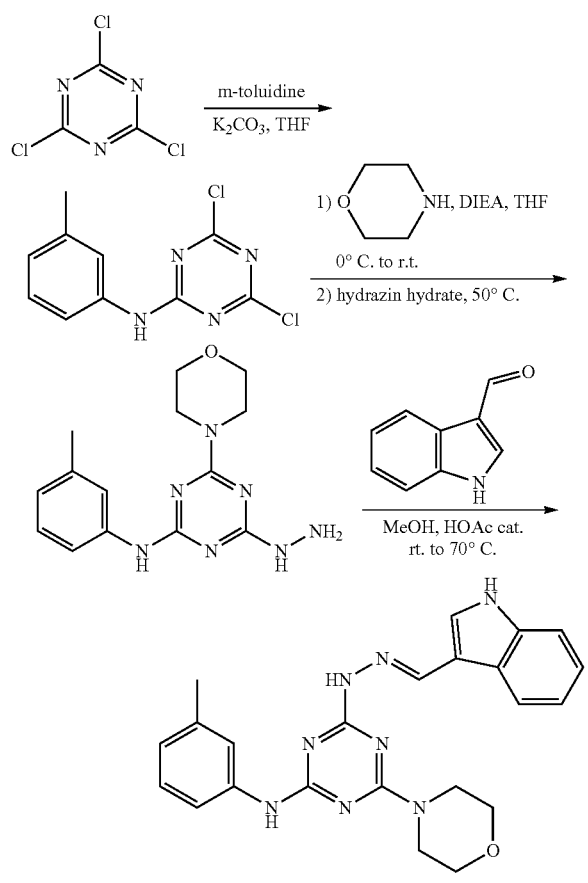

Step 1
To a mixture of 2,4,6-trichloro-[1,3,5]triazine (700 mg, 3.8 mmol) and K$_2$CO$_3$ (528 mg, 3.8 mmol) in THF (15 mL) at 0° C. was added dropwise a solution of m-tolylamine (407 mg, 3.8 mmol) in THF (5 mL) slowly. After addition, the resulting mixture was stirred for 12 hrs, left the temperature slowly warm to rt. Solvent was removed and the residue was purified by silica gel column chromatography (PE/EA=20/1 to 10/1) to give (4,6-dichloro-[1,3,5]triazin-2-yl)-m-tolyl-amine (200 mg, yield: 21%) as a yellow solid. The reaction was monitored by TLC and the molecular ionic strength of the product was weak on LCMS spectroscopy. Note: If the reaction done at −20° C. could significantly reduce the dimer\trimer byproducts and increase the yield.

Step 2
To s mixture of (4,6-dichloro-[1,3,5]triazin-2-yl)-m-tolyl-amine (200 mg, 0.787 mmol) ad DIEA (103 mg, 0.787 mmol) in THF (10 mL) at 0° C. was added morpholine (69 mg, 0.787 mmol). The resulting mixture was stirred for additional 2 hrs at rt. Then hydrazine monohydrate (0.5 mL, 10 mmol) was added into the above mixture. After addition, the reaction mixture was heated at 50° C. for 3 hrs. Volatiles were removed in vacuum to give crude (4-hydrazino-6-morpholin-4-yl-[1,3,5]triazin-2-yl)-m-tolyl-amine (250 mg, crude) as a white solid. MS: m/z 301.9 (M+H$^+$).

Step 3
A mixture of (4-hydrazino-6-morpholin-4-yl-[1,3,5]triazin-2-yl)-m-tolyl-amine (95 mg, crude, 0.31 mmol) and 1H-indole-3-carbaldehyde (46 mg, 0.31 mmol) in MeOH (5 mL, one drop of HOAc was added as catalyst) was heated at 70° C. for 2 hrs. The reaction mixture was filtered and the filtrate was purified by prep-HPLC (NH$_4$CO$_3$ system) to give {4-[N'-(1H-indol-3-ylmethylene)-hydrazino]-6-morpholin-4-yl-[1,3,5]triazin-2-yl}-m-tolyl-amine (60 mg, yield: 45% over 2 steps) as a white solid.

$^1$H NMR (400 MHz, DMSO-d6): δ=11.42 (brs, 1H), 10.57 (brs, 1H), 9.08 (brs, 1H), 8.42 (d, J=8.0 Hz, 1H), 8.33 (s, 1H), 7.69 (s, 1H), 7.54-7.39 (m, 2H), 7.25-7.07 (m, 3H), 6.82-6.77 (m, 1H), 3.89-3.59 (m, 8H), 2.27 (s, 3H). MS: m/z 429.0 (M+H$^+$).

Example 10—(4-Fluoro-phenyl)-{4-[N'-(1H-indol-3-ylmethylene)-hydrazino]-6-morpholin-4-yl-[1,3,5]triazin-2-yl}-amine

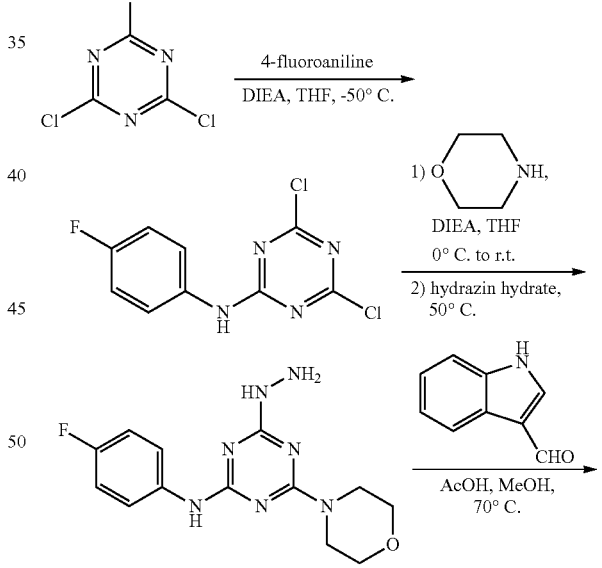

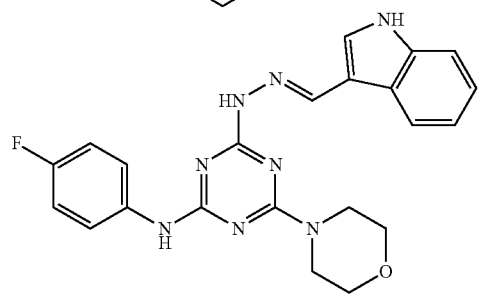

Step 1

To a solution of 2,4,6-trichloro-[1,3,5]triazine (500 mg, 2.71 mmol) and DIEA (350 mg, 2.71 mmol) in THF (25 mL) was slowly added a solution of 4-fluoro-phenylamine (301 mg, 2.711 mmol) in THF (5 mL) at −50° C. under $N_2$ atmosphere. The resulting mixture was stirred at −50° C. for 2 hrs. THF was removed and $H_2O$ (50 mL) was added. The mixture was extracted with EA (50 mL×3). The combined organic layer was washed with brine (150 mL×3). Then the separated organic layer was concentrated to give the residue. The residue was purified by silica gel column (PE/EA=50/1) to yield (4,6-dichloro-[1,3,5]triazin-2-yl)-(4-fluoro-phenyl)-amine (524 mg, yield: 75%) as a white solid.

Step 2

To a solution of (4,6-dichloro-[1,3,5]triazin-2-yl)-(4-fluoro-phenyl)-amine (300 mg, 1.16 mmol) and DIEA (150 mg, 1.16 mmol) in THF (20 mL) was added a solution of morpholine (101 mg, 1.16 mmol) in THF (5 mL) at 0° C. under $N_2$ atmosphere. The resulting mixture was stirred at 0° C. for 1 hr. Then hydrazine monohydrate (0.6 mL) was added. The reaction was continued stirring at 50° C. for additional 30 min. THF was removed and $H_2O$ (30 mL) was added. The mixture was extracted with EA (30 mL×3). The combined organic layer was washed with brine (90 mL×3). Then the separated organic layer was concentrated to give crude (4-fluoro-phenyl)-(4-hydrazino-6-morpholin-4-yl-[1,3,5]triazin-2-yl)-amine (353 mg), which was used directly in the next step.

Step 3

A mixture of (4-fluoro-phenyl)-(4-hydrazino-6-morpholin-4-yl-[1,3,5]triazin-2-yl)-amine (353 mg, 1.16 mmol), 1H-indole-3-carbaldehyde (169 mg, 1.16 mmol) and AcOH (4 drops) in MeOH (20 mL) was stirred at 70° C. for 1 hr under $N_2$ atmosphere. MeOH was removed and $H_2O$ (10 mL) was added. The mixture was extracted with EA (10 mL×3). The combined organic layer was washed with brine (30 mL×3). The separated organic layer was concentrated to give the residue. The residue was purified by prep-HPLC to give (4-fluoro-phenyl)-{4-[N-(1H-indol-3-ylmethylene)-hydrazino]-6-morpholin-4-yl-[1,3,5]triazin-2-yl}-amine (354 mg, yield: 71% for three steps).

$^1$H NMR (400 MHz, DMSO-$d_6$): δ=11.44 (brs, 1H), 10.62 (brs, 1H), 9.29 (brs, 1H), 8.42 (d, J=7.6 Hz, 1H), 8.33 (s, 1H), 8.07 (brs, 1H), 7.87-7.69 (m, 2H), 7.43 (d, J=7.6 Hz, 1H), 7.26-7.16 (m, 1H), 7.25-7.06 (m, 3H), 3.76-3.67 (m, 8H). MS: m/z 433.0 (M+H$^+$).

Example 11—(E)-4-(2-((1h-indol-3-yl)methylene)hydrazinyl)-n-(4-chlorophenyl)-6-morpholino-1,3,5-triazin-2-amine

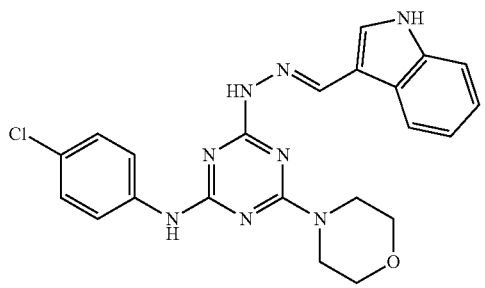 [SMILES: Clc1ccc(Nc2nc(N/N=C/c3c[nH]c4ccccc34)nc(N3CCOCC3)n2)cc1]

The title compound was prepared using methods and procedures similar to those described in Example 10 using p-chloroaniline as a starting material.

$^1$H NMR (400 MHz, DMSO-$d_6$): δ=11.45 (s, 1H), 10.70-10.63 (m, 1H), 9.39-9.37 (m, 1H), 8.42 (d, J=7.6 Hz, 1H), 8.33 (s, 1H), 8.15-8.05 (m, 1H), 7.87-7.82 (m, 1H), 7.71 (d, J=2 Hz, 1H), 7.45-7.43 (m, 1H), 7.37-7.26 (m, 2H), 7.23-7.17 (m, 1H), 7.13-7.09 (m, 1H), 3.87-3.61 (m, 8H).

MS: m/z 448.9 (M+H$^+$)

Example 12—{4-[N'-(1H-Indol-3-ylmethylene)-hydrazino]-6-morpholin-4-yl-[1,3,5]triazin-2-yl}-(4-methoxy-phenyl)-amine

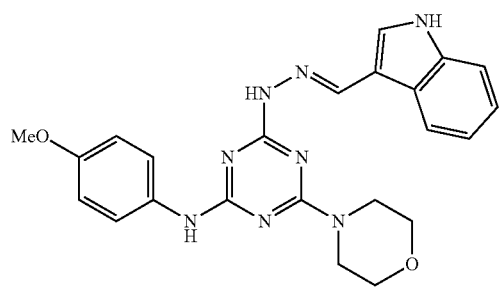

The title compound was prepared using methods and procedures similar to those described for Example 10.

$^1$H NMR (400 MHz, DMSO-$d_6$): δ=11.42 (brs, 1H), 10.56 (brs, 1H), 9.06 (brs, 1H), 8.44 (d, J=8.4 Hz, 1H), 8.32 (s, 1H), 8.01 (s, 1H), 7.80-7.54 (m, 2H), 7.42 (d, J=8.4 Hz, 1H), 7.26-7.17 (m, 1H), 7.12 (t, J=7.2 Hz, 1H), 6.89 (d, J=8.8 Hz, 2H), 4.07-3.49 (m, 11H). MS: m/z 445.0 (M+H$^+$)

Example 13—2-{4-[N'-(1H-Indol-3-ylmethylene)-hydrazino]-6-p-tolylamino-[1,3,5]triazin-2-ylamino}-ethanol

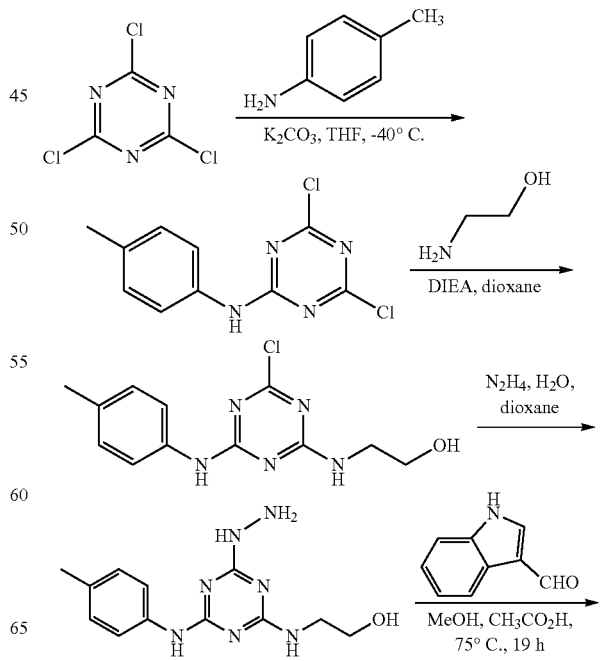

-continued

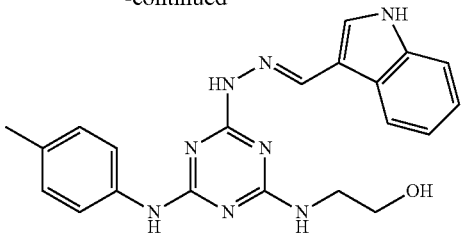

Step 1

To a solution of 2,4,6-trichloro-[1,3,5]triazine (3 g, 16.3 mmoL) and K$_2$CO$_3$ (1.12 g, 8.15 mmoL) in THF (30 mL) was added a solution of p-tolylamine (0.87 g, 8.15 mmoL) in THF (20 mL) dropwise at −40° C. The mixture was stirred at −40° C. for 0.5 h. The reaction mixture was filtered and the filtrate was concentrated. The residue was purified by silica flash column (10% EA in PE) to give (4,6-dichloro-[1,3,5]triazin-2-yl)-p-tolyl-amine (1.1 g, yield: 55%) as a white solid.

$^1$H NMR (400 MHz, DMSO-d6): δ=11.05 (s, 1H), 7.46 (d, J=8.4 Hz, 2H), 7.20 (d, J=8.8 Hz, 2H), 2.29 (s, 3H).

Step 2

A solution of (4,6-dichloro-[1,3,5]triazin-2-yl)-p-tolyl-amine (800 mg, 3.1 mmoL), DIEA (0.7 mL, 3.9 mmoL) and 2-amino-ethanol (230 mg, 3.8 mmoL) in dioxane (7 mL) was stirred at 35° C. for 1.5 hrs. The reaction mixture was diluted with H$_2$O (10 mL) and the mixture was stirred at room temperature for 1 hr. Then the suspension was filtered and the collected filter cake was air dried to give 2-(4-chloro-6-p-tolylamino-[1,3,5]triazin-2-ylamino)-ethanol (860 mg, yield: 98%) as a white solid. MS: m/z 280.0 (M+H$^+$).

Step 3

A solution of 2-(4-chloro-6-p-tolylamino-[1,3,5]triazin-2-ylamino)-ethanol (400 mg, 1.43 mmoL) and N$_2$H$_4$·H$_2$O (1 mL) in dioxane (6 mL) was stirred at room temperature for 1 hr. The mixture was co-evaporated with MeOH (5 mL×4) to give 2-(4-hydrazino-6-p-tolylamino-[1,3,5]triazin-2-ylamino)-ethanol (crude) as a white solid. MS: m/z 276.0 (M+H$^+$).

Step 4

A solution of 2-(4-hydrazino-6-p-tolylamino-[1,3,5]triazin-2-ylamino)-ethanol (380 mg, 1.38 mmoL), 1H-indole-3-carbaldehyde (391 mg, 2.69 mmoL) and two drops HOAc in MeOH (16 mL) was stirred at 75° C. for 19 hrs. The reaction mixture was concentrated and the residue was purified by prep-HPLC (NH$_3$·H$_2$O) to give 2-{4-[N'-(1H-indol-3-ylmethylene)-hydrazino]-6-p-tolylamino-[1,3,5]triazin-2-ylamino}-ethanol (18 mg, yield: 7%) as a white solid.

$^1$H NMR (400 MHz, DMSO-d6): δ=11.42 (brs, 1H), 10.52-10.37 (m, 1H), 8.97-8.95 (m, 1H), 8.45-8.43 (m, 1H), 8.33 (s, 1H), 8.14-8.68 (m, 3H), 7.42 (d, J=8.0 Hz, 1H), 7.23-7.09 (m, 4H), 6.62-6.60 (m, 1H), 4.69 (s, 1H), 3.55-3.52 (m, 2H), 3.40-3.36 (m, 2H), 2.28 (s, 3H).

MS: m/z 403.0 (M+H$^+$).

Example 14—2-((2-Hydroxy-ethyl)-{4-[N'-(1H-indol-3-ylmethylene)-hydrazino]-6-p-tolylamino-[1,3,5]triazin-2-yl}-amino)-ethanol

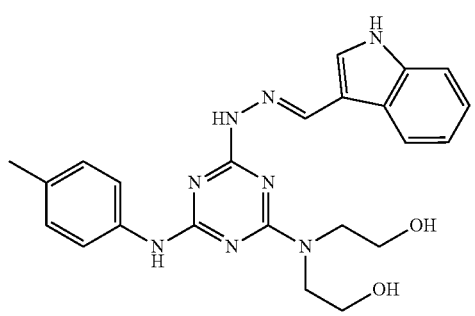 [SMILES: Cc1ccc(Nc2nc(N/N=C/c3c[nH]c4ccccc34)nc(N(CCO)CCO)n2)cc1]

The title compound was prepared using methods and procedures similar to those used in Example 13.

$^1$H NMR (400 MHz, DMSO-d6): δ=11.40 (brs, 1H), 10.48 (brs, 1H), 8.98 (brs, 1H), 8.44 (d, J=8.4 Hz, 1H), 8.34 (s, 1H), 7.90-7.68 (m, 3H), 7.41 (d, J=7.2 Hz, 1H), 7.24-6.70 (m, 4H), 5.01-4.74 (m, 2H), 3.69-3.66 (m, 8H), 2.28 (s, 3H).

MS: m/z 447.0 (M+H$^+$).

Example 15—{4-[N'-(1H-Indol-3-ylmethylene)-hydrazino]-6-piperidin-1-yl-[1,3,5]triazin-2-yl}-p-tolyl-amine

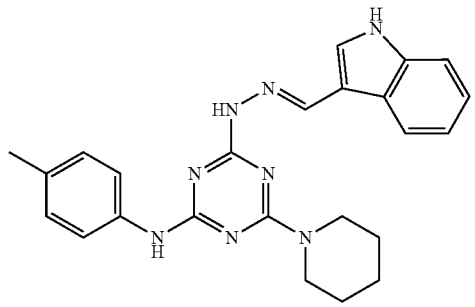 [SMILES: Cc1ccc(Nc2nc(N/N=C/c3c[nH]c4ccccc34)nc(N3CCCCC3)n2)cc1]

The title compound was prepared using methods and procedures similar to those used in Example 13.

$^1$H NMR (300 MHz, DMSO-d6): δ=11.42 (brs, 1H), 10.51 (brs, 1H), 9.01 (brs, 1H), 8.48-8.45 (m, 1H), 8.32 (s, 1H), 8.05-7.66 (m, 3H), 7.45-7.39 (m, 1H), 7.26-7.09 (m, 4H), 3.76-3.75 (m, 4H), 2.28 (s, 3H), 1.68-1.52 (m, 6H).

MS: m/z 427.0 (M+H$^+$).

Example 16—{4-[N'-(1H-Indol-3-ylmethylene)-hydrazino]-6-pyrrolidin-1-yl-[1,3,5]triazin-2-yl}-p-tolyl-amine

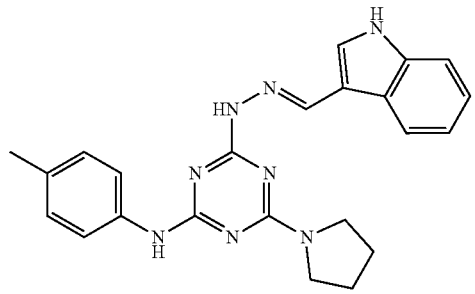 [SMILES: Cc1ccc(Nc2nc(N/N=C/c3c[nH]c4ccccc34)nc(N3CCCC3)n2)cc1]

The title compound was prepared using methods and procedures similar to those used in Example 13.

$^1$H NMR (300 MHz, DMSO-d6): δ=11.41 (brs, 1H), 10.54 (brs, 1H), 9.02 (brs, 1H), 8.49-8.46 (m, 1H), 8.33 (s, 1H), 7.93-7.66 (m, 2H), 7.43-7.41 (m, 1H), 7.26-7.22 (m, 1H), 7.12-7.09 (m, 4H), 3.56-3.53 (m, 4H), 2.28 (s, 3H), 1.92-1.90 (m, 4H).

MS: m/z 413.0 (M+H$^+$).

Example 17—[4-[N'-(1H-Indol-3-ylmethylene)-hydrazino]-6-(4-methyl-piperazin-1-yl)-[1,3,5]triazin-2-yl]-p-tolyl-amine

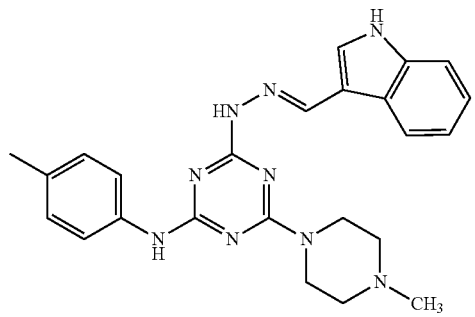 [SMILES: Cc1ccc(Nc2nc(N/N=C/c3c[nH]c4ccccc34)nc(N3CCN(C)CC3)n2)cc1]

The title compound was prepared using methods and procedures similar to those used in Example 13.

$^1$H NMR (300 MHz, DMSO-d6): δ=11.42 (brs, 1H), 10.55 (brs, 1H), 9.06 (brs, 1H), 8.45 (d, J=7.2 Hz, 1H), 8.31 (s, 1H), 7.97-7.68 (m, 3H), 7.42 (d, J=8.1 Hz, 1H), 7.27-7.09 (m, 4H), 3.77-3.76 (m, 4H), 2.36-2.35 (m, 4H), 2.28 (s, 3H), 2.22 (s, 3H).

MS: m/z 442.0 (M+H$^+$).

Example 18—{4-[N'-(1H-Indol-3-ylmethylene)-hydrazino]-6-piperazin-1-yl-[1,3,5]triazin-2-yl}-p-tolyl-amine

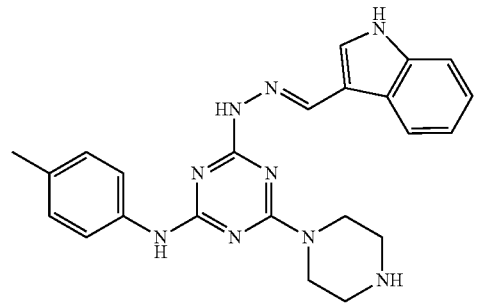 [SMILES: Cc1ccc(Nc2nc(N/N=C/c3c[nH]c4ccccc34)nc(N3CCNCC3)n2)cc1]

The title compound was prepared using methods and procedures similar to those used in Example 13.

$^1$H NMR (300 MHz, DMSO-d6): δ=11.41 (brs, 1H), 10.51 (brs, 1H), 9.03 (brs, 1H), 8.45 (d, J=7.2 Hz, 1H), 8.31 (s, 1H), 8.0-7.91 (m, 3H), 7.68-7.41 (m, 1H), 7.21-7.08 (m, 4H), 3.73-3.67 (m, 4H), 2.74-2.72 (m, 4H), 2.28 (s, 3H).

MS: m/z 428.3 (M+H$^+$).

Example 19—{4-[N'-(1H-Indol-3-ylmethylene)-hydrazino]-6-morpholin-4-yl-[1,3,5]triazin-2-yl}-o-tolyl-amine

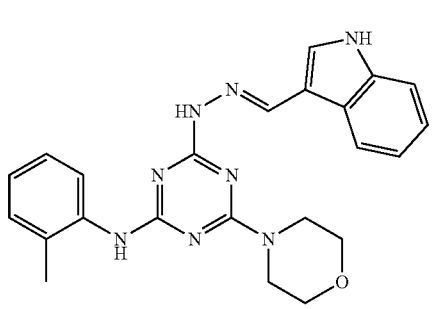 [SMILES: Cc1ccccc1Nc1nc(N/N=C/c2c[nH]c3ccccc23)nc(N2CCOCC2)n1]

The title compound was prepared using methods and procedures similar to those described for Example 10.

$^1$H NMR (400 MHz, DMSO-d$_6$): δ=11.36 (brs, 1H), 10.50 (brs, 1H), 8.57-8.00 (m, 3H), 7.85-7.44 (m, 2H), 7.39 (d, J=8.0 Hz, 1H), 7.29-7.13 (m, 3H), 7.13-6.96 (m, 2H), 4.05-3.50 (m, 8H), 2.27 (s, 3H).

MS: m/z 429.2 (M+H$^+$).

Example 20—(E)-4-(2-((1h-indol-3-yl)methylene)hydrazinyl)-6-morpholino-n-(4-(trifluoromethyl)phenyl)-1,3,5-triazin-2-amine

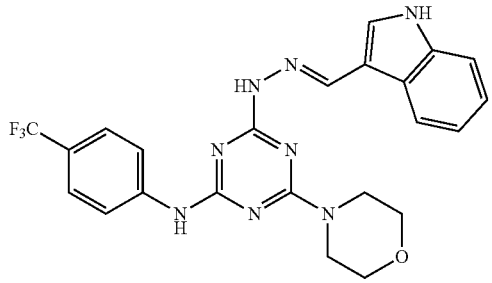

The title compound was prepared using methods and procedures similar to those described for Example 10.

$^1$H NMR (400 MHz, DMSO-d$_6$): δ=11.45 (brs, 1H), 10.76 (brs, 1H), 9.67 (m, 1H), 8.45 (d, J=8.0 Hz, 1H), 8.35-8.27 (m, 3H), 7.89 (s, 1H), 7.73-7.60 (m, 2H), 7.45-7.42 (m, 1H), 7.24-7.21 (m, 1H), 7.11-7.07 (m, 1H), 3.85-3.62 (m, 8H).

MS: m/z 483.2 (M+H$^+$)

Example 21—(E)-4-(2-((1h-indol-3-yl)methylene)hydrazinyl)-n-(4-bromophenyl)-6-morpholino-1,3,5-triazin-2-amine

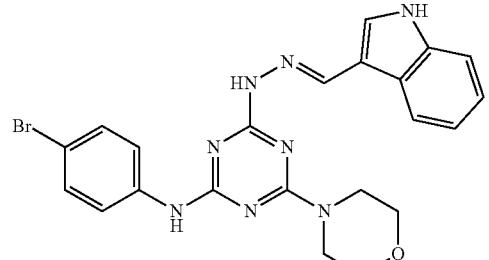

The title compound was prepared using methods and procedures similar to those described for Example 10.

$^1$H NMR (400 MHz, DMSO-d$_6$): δ=11.45 (brs, 1H), 10.68 (brs, 1H), 9.25 (brs, 1H), 8.42 (d, J=7.6 Hz, 1H), 8.33 (s, 1H), 8.06-8.05 (m, 1H), 7.71-7.63 (m, 2H), 7.46-7.41 (m, 3H), 7.23-7.20 (m, 1H), 7.13-7.09 (m, 1H), 3.80-3.60 (m, 8H).

MS: m/z 495.1 (M+H$^+$).

Example 22—(E)-4-((4-(2-((1H-indol-3-yl)methylene)hydrazinyl)-6-morpholino-1,3,5-triazin-2-yl)amino)benzonitrile

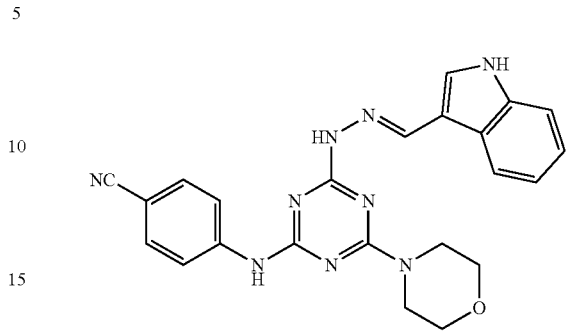

The title compound was prepared using methods and procedures similar to those described for Example 10.

$^1$H NMR (400 MHz, DMSO-d$_6$): δ=11.48 (brs, 1H), 10.75 (brs, 1H), 9.72 (brs, 1H), 8.43 (d, J=7.6 Hz, 1H), 8.39 (s, 1H), 8.35-8.30 (m, 1H), 8.18-7.90 (m, 1H), 7.74-7.63 (m, 3H), 7.73-7.65 (m, 1H), 7.25-7.07 (m, 2H), 4.02-3.83 (m, 8H).

MS: m/z 440.2 (M+H$^+$)

Example 23—[4-Morpholin-4-yl-6-(N'-pyridin-3-ylmethylene-hydrazino)-[1,3,5]triazin-2-yl]-p-tolyl-amine

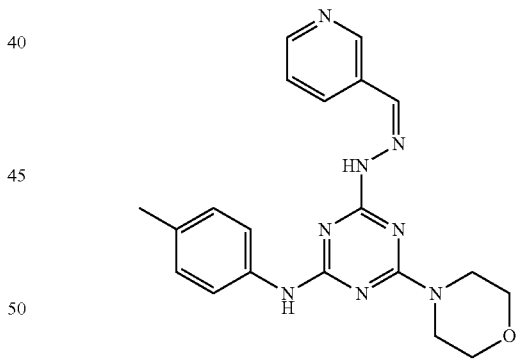

The title compound was prepared using methods and procedures similar to those described for Example 10.

$^1$H NMR (400 MHz, DMSO-d6): δ=11.06 (s, 1H), 9.23 (s, 1H), 8.82 (s, 1H), 8.58-8.53 (dd, J=4.8, 1.6 Hz, 1H), 8.17 (s, 1H). 8.08-8.03 (m, 1H), 7.68 (s, 2H), 7.50-7.44 (m, 1H), 7.08 (d, J=8.4 Hz, 2H), 3.81-3.62 (m, 8H), 2.25 (s, 3H).

MS: m/z 391.0 (M+H$^+$).

Example 24—{4-Morpholin-4-yl-6-[N'-(1H-pyrrol-3-ylmethylene)-hydrazino]-[1,3,5]triazin-2-yl}-p-tolyl-amine

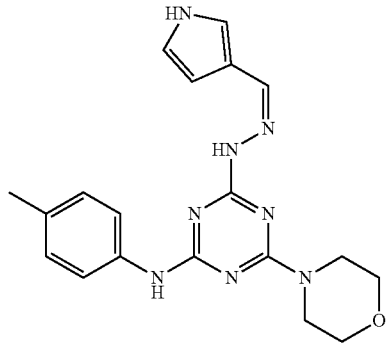 [SMILES: Cc1ccc(Nc2nc(N/N=C\c3cc[nH]c3)nc(N3CCOCC3)n2)cc1]

The title compound was prepared using methods and procedures similar to those described for Example 10.

$^1$H NMR (400 MHz, DMSO-d6): δ=11.02 (s, 1H), 10.37 (s, 1H), 9.14 (s, 1H), 8.04 (s, 1H), 7.70-7.66 (m, 2H), 7.07 (d, J=2.0 Hz, 1H), 7.06 (d, J=8.8 Hz, 2H), 6.80 (d, J=2.0 Hz, 1H), 6.36 (s, 1H), 3.78-3.59 (m, 8H), 2.24 (s, 3H).

MS: m/z 379.0 (M+H$^+$).

Example 25—(3-Chloro-phenyl)-{4-[N'-(1H-indol-3-ylmethylene)-hydrazino]-6-morpholin-4-yl-[1,3,5]triazin-2-yl}-amine

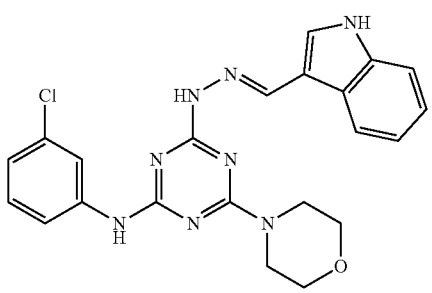 [SMILES: Clc1cccc(Nc2nc(N/N=C/c3c[nH]c4ccccc34)nc(N3CCOCC3)n2)c1]

The title compound was prepared using methods and procedures similar to those described for Example 10.

$^1$H NMR (400 MHz, DMSO-d$_6$): δ=11.44 (brs, 1H), 10.67 (brs, 1H), 9.60-9.11 (m, 1H), 8.41 (s, 1H), 8.35 (s, 1H), 8.16-7.57 (m, 3H), 7.42 (d, J=8.0 Hz, 1H), 7.37-7.24 (m, 1H), 7.20 (t, J=7.2 Hz, 1H), 7.12 (t, J=7.2 Hz, 1H), 7.07-6.94 (m, 1H), 3.96-3.55 (m, 8H).

MS: m/z 448.9 (M+H$^+$).

Example 26—(E)-4-(2-((1H-indol-3-yl)methylene)hydrazinyl)-6-morpholino-N-(4-nitrophenyl)-1,3,5-triazin-2-amine

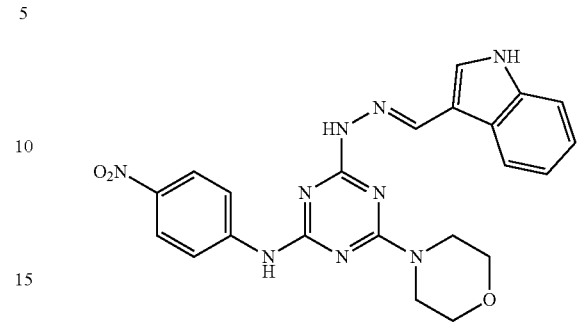

The title compound was prepared using methods and procedures similar to those described for Example 10.

$^1$H NMR (400 MHz, DMSO-d$_6$): δ=11.49 (brs, 1H), 10.85 (brs, 1H), 10.04 (brs, 1H), 8.46 (d, J=7.8 Hz, 1H), 8.43 (s, 2H), 8.37-8.16 (m, 2H), 8.08-8.07 (m, 1H), 7.75 (s, 1H), 7.47-7.43 (m, 1H), 7.26-7.20 (m, 2H), 3.91-3.62 (m, 8H).

MS: m/z 460.0 (M+H$^+$).

Example 27—N1-(4-(2-((1h-indol-3-yl)methylene)hydrazinyl)-6-morpholino-1,3,5-triazin-2-yl)benzene-1,4-diamine

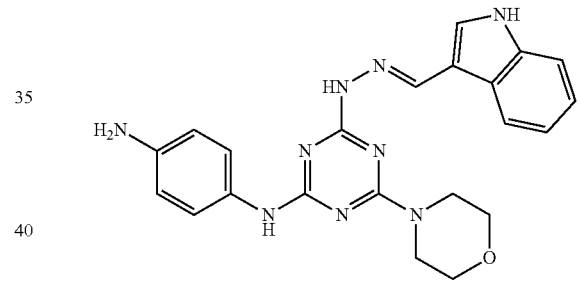

The title compound was prepared using methods and procedures similar to those described for Example 10.

$^1$H NMR (800 MHz, DMSO-d$_6$): δ=11.38 (brs, 1H), 10.46 (brs, 1H), 8.86-8.75 (m, 1H), 8.43-8.41 (m, 1H), 8.29 (s, 1H), 7.73-7.69 (m, 1H), 7.66-7.64 (m, 1H), 7.43-7.38 (m, 1H), 7.34-7.14 (m, 3H), 6.59-6.48 (m, 2H), 4.84-4.74 (m, 2H), 3.82-3.59 (m, 8H).

MS: m/z 430.2 (M+H$^+$)

Example 28—(E)-N-(4-((4-(2-((1H-indol-3-yl)methylene)hydrazinyl)-6-morpholino-1,3,5-triazin-2-yl)amino)phenyl)acetamide

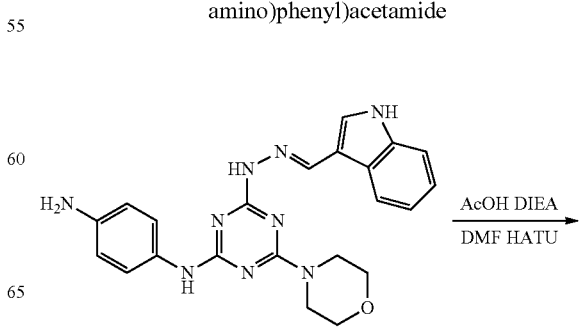

-continued

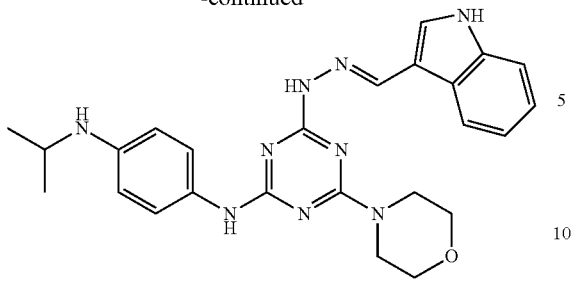

To a solution of (E)-4-(2-((1H-indol-3-yl)methylene)hydrazinyl)-N-(4-aminophenyl)-6-morpholino-1,3,5-triazin-2-amine (100 mg, 0.2 mmol) and AcOH (14 mg, 0.2 mmol) in DMF (15 mL) was added DIEA (90.3 mg, 0.6 mmol) and HATU (132.8 mg, 0.3 mmol). The solution was stirred at room temperature for 2 hrs under $N_2$ atmosphere. The solution was concentrated to give the residue. The residue was purified by prep-HPLC ($NH_4HCO_3$) to give (E)-N-(4-((4-(2-((1H-indol-3-yl)methylene)hydrazinyl)-6-morpholino-1,3,5-triazin-2-yl)amino)phenyl)acetamide (15 mg, yield: 13.6%).

$^1$H NMR (400 MHz, DMSO-$d_6$): δ=11.40 (brs, 1H), 10.60 (brs, 1H), 9.85 (brs, 1H), 9.12 (brs, 1H), 8.45-8.32 (m, 2H), 8.05-8.00 (m, 1H), 7.69-7.41 (m, 5H), 7.22-7.19 (m, 2H), 3.81-3.63 (m, 8H), 2.07-2.04 (m, 3H).

MS: m/z 472.0 (M+H$^+$)

Example 29—(E)-6-(2-((1H-Indol-3-yl)methylene)hydrazinyl)-N2,N2-bis(2-methoxyethyl)-N4-(p-tolyl)-1,3,5-triazine-2,4-diamine

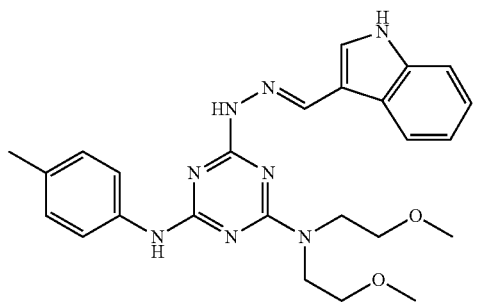 [SMILES: COCCN(CCOC)c1nc(N/N=C/c2c[nH]c3ccccc23)nc(Nc2ccc(C)cc2)n1]

The title compound was prepared using methods and procedures similar to those described for Example 13.

$^1$H NMR (400 MHz, DMSO-$d_6$): δ=11.40 (brs, 1H), 10.49 (brs, 1H), 9.13-8.81 (m, 1H), 8.46 (d, J=4.8 Hz, 1H), 8.30 (d, J=6.4 Hz, 1H), 7.67-7.63 (m, 3H), 7.42 (d, J=7.6 Hz, 1H), 7.21-7.10 (m, 4H), 3.76-3.72 (m, 4H), 3.61-3.50 (m, 4H), 3.29 (s, 6H), 2.28 (s, 3H).

MS: m/z 475.0 (M+H$^+$).

Example 30—(E)-6-(2-((1H-Indol-3-yl)methylene)hydrazinyl)-N2,N2-dimethyl-N4-(p-tolyl)-1,3,5-triazine-2,4-diamine

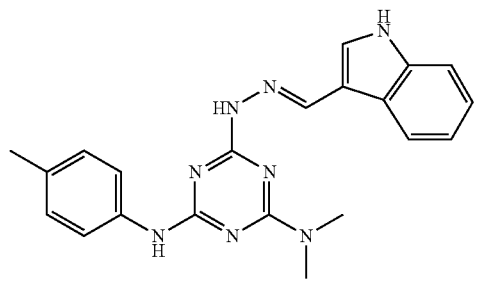 [SMILES: Cc1ccc(Nc2nc(N/N=C/c3c[nH]c4ccccc34)nc(N(C)C)n2)cc1]

The title compound was prepared using methods and procedures similar to those described for Example 13.

$^1$H NMR (400 MHz, DMSO-d6): δ=11.41 (brs, 1H), 10.50 (brs, 1H), 9.01 (brs, 1H), 8.46 (d, J=8.0 Hz, 1H), 8.33 (s, 1H), 8.10-7.65 (m, 3H), 7.42 (d, J=7.6 Hz, 1H), 7.25-7.03 (m, 4H), 3.13 (s, 6H), 2.28 (s, 3H).

MS: m/z 387.0 (M+H$^+$).

Example 31—[4-(N'-Benzo[b]thiophen-3-ylmethylene-hydrazino)-6-morpholin-4-yl-[1,3,5]triazin-2-yl]-p-tolyl-amine

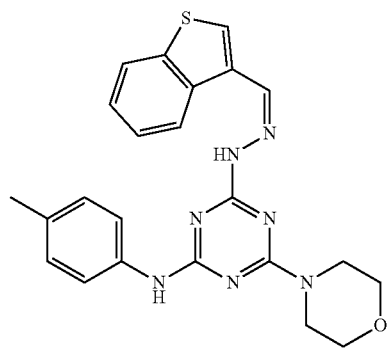

The title compound was prepared using methods and procedures similar to those described for Example 10.

$^1$H NMR (400 MHz, DMSO-d6): δ=10.91 (brs, 1H), 9.29-8.88 (m, 2H), 8.42 (s, 1H), 8.13-7.96 (m, 2H), 7.88-7.55 (m, 2H), 7.52-7.34 (m, 2H), 7.09 (d, J=8.0 Hz, 2H), 4.05-3.47 (m, 8H), 2.28 (s, 3H).

MS: m/z 446.0 (M+H$^+$).

Example 32—[4-Morpholin-4-yl-6-(N'-pyridin-4-ylmethylene-hydrazino)-[1,3,5]triazin-2-yl]-p-tolyl-amine

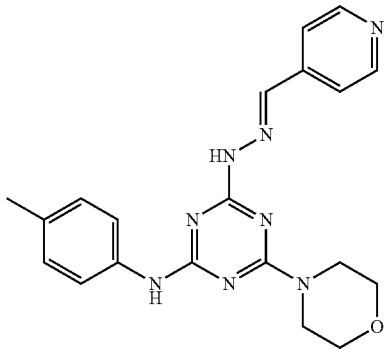 [SMILES: Cc1ccc(Nc2nc(N/N=C/c3ccncc3)nc(N3CCOCC3)n2)cc1]

The title compound was prepared using methods and procedures similar to those described for Example 10.

$^1$H NMR (400 MHz, DMSO-d6): δ=11.19 (brs, 1H), 9.27 (brs, 1H), 8.42 (s, 1H), 8.62 (d, J=6.0 Hz 2H), 8.10 (s, 1H), 7.79-7.63 (m, 2H), 7.60 (d, J=5.6 Hz, 2H), 7.09 (d, J=8.4 Hz, 2H), 3.84-3.61 (m, 8H), 2.26 (s, 3H).
MS: m/z 391.0 (M+H$^+$).

Example 33—[4-(N'-Benzylidene-hydrazino)-6-morpholin-4-yl-[1,3,5]triazin-2-yl]-p-tolyl-amine

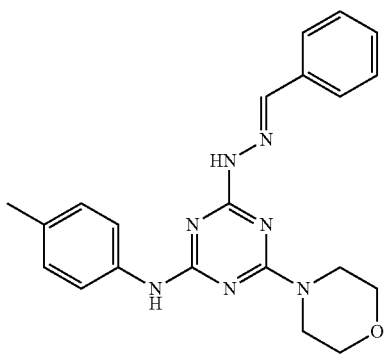 [SMILES: Cc1ccc(Nc2nc(N/N=C/c3ccccc3)nc(N3CCOCC3)n2)cc1]

The title compound was prepared using methods and procedures similar to those described for Example 10.

$^1$H NMR (400 MHz, DMSO-d6): δ=10.87 (s, 1H), 9.21 (s, 1H), 8.14 (s, 1H), 7.78-7.56 (m, 4H), 7.48-7.32 (m, 3H), 7.08 (d, J=8.4 Hz, 2H), 3.87-3.57 (m, 8H), 2.25 (s, 3H).
MS: m/z 390.0 (M+H$^+$).

Example 34—(E)-N1-(4-(2-((1H-indol-3-yl)methylene)hydrazinyl)-6-morpholino-1,3,5-triazin-2-yl)-N4,N4-dimethylbenzene-1,4-diamine

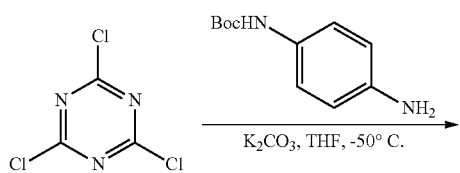

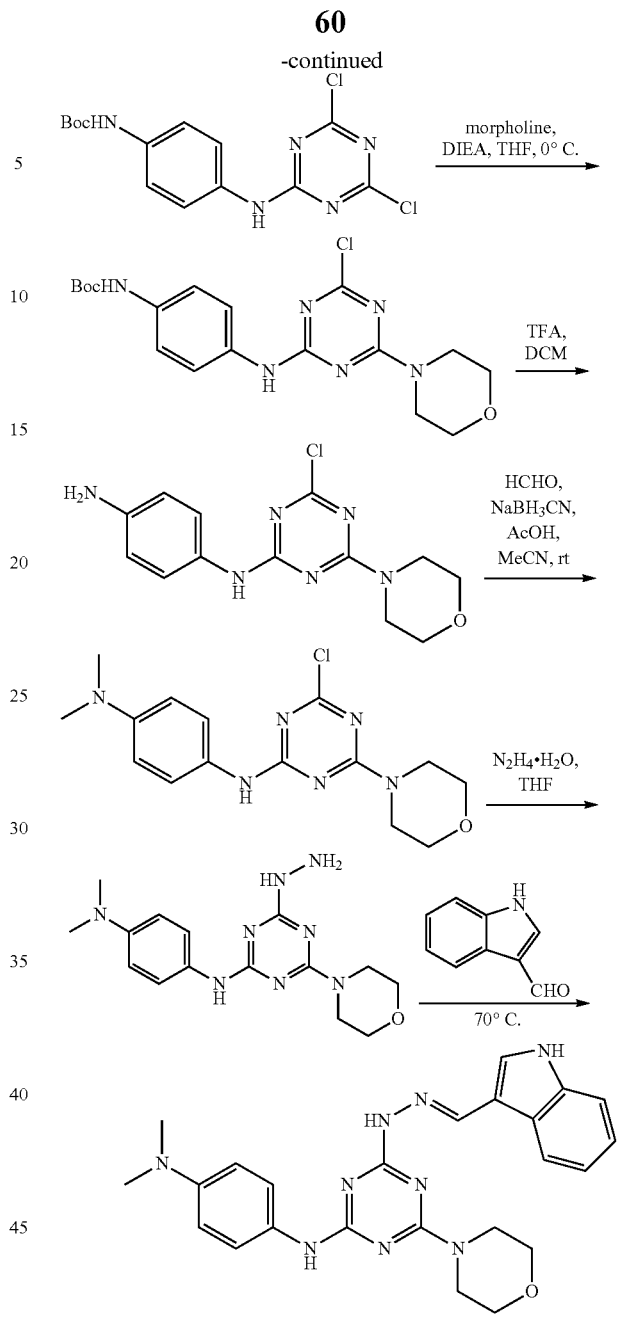

Step 1

To a solution of 2,4,6-trichloro-[1,3,5] triazine (6.7 g, 36.2 mmol) and K$_2$CO$_3$ (2.6 g, 18.8 mmol) in THF (160 mL) was slowly added a solution of tert-butyl (4-aminophenyl)carbamate (5.2 mg, 25.0 mmol) in THF (40 mL) at −50° C. under N$_2$ atmosphere. The resulting mixture was stirred at −50° C. for 2 hrs. THF was removed and H$_2$O (150 mL) was added. The mixture was extracted with EA (150 mL×3). The combined organic layer was washed with brine (150 mL) and concentrated to give the residue. The residue was purified by silica gel column (PE/EA=10/1) to yield tert-butyl (4-((4,6-dichloro-1,3,5-triazin-2-yl)amino)phenyl)carbamate (4.4 g, yield: 50%) as a white solid.

$^1$H NMR (400 MHz, CDCl$_3$): δ=7.57 (s, 1H), 7.42 (d, J=8.8 Hz, 2H), 7.38 (d, J=8.8 Hz, 2H), 6.54 (s, 1H), 1.53 (s, 9H).

Step 2

To a solution of (4-((4,6-dichloro-1,3,5-triazin-2-yl)amino)phenyl)carbamate (2 g, 5.6 mmol) and DIEA (726 mg, 5.6 mmol) in THF (50 mL) was added a solution of morpholine (489 mg, 5.6 mmol) in THF (15 mL) at 0° C. under N$_2$ atmosphere. The resulting mixture was stirred at 0° C. for 2 hrs. Then the solution was concentrated and purified by silica gel column (PE/EA=8/1) to yield tert-butyl (4-((4-chloro-6-morpholino-1,3,5-triazin-2-yl)amino)phenyl)carbamate (1.8 g, yield: 80%) as a white solid.

Step 3

A solution of tert-butyl (4-((4-chloro-6-morpholino-1,3,5-triazin-2-yl)amino)phenyl)carbamate (1 g, 2.5 mmol) in DCM/TFA (5/1) (20 mL) was stirred at room temperature overnight. The reactant was concentrated and the residue was partitioned between NaHCO$_3$(aq) and EA (each 50 mL). Then the organic phase was dried over Na$_2$SO$_4$ and concentrated to afford N1-(4-chloro-6-morpholino-1,3,5-triazin-2-yl)benzene-1,4-diamine as a gray solid (crude).

Step 4

To a solution of N1-(4-chloro-6-morpholino-1,3,5-triazin-2-yl)benzene-1,4-diamine (900 mg, 2.9 mmol) in MeCN (40 mL) was added HCHO (37%) (2.38 g, 29.3 mmol), NaBH$_3$CN (553.5 mg, 8.9 mmol) and HOAc (616.5 mg, 10.3 mmol), the solution was stirred at room temperature overnight. The reactant was concentrated and the residue was purified by silica gel column (PE/EA=5/1) to yield N1-(4-chloro-6-morpholino-1,3,5-triazin-2-yl)-N4,N4-dimethylbenzene-1,4-diamine (216.7 g, yield: 31%) as a yellow solid.

Step 5

To a solution of N1-(4-chloro-6-morpholino-1,3,5-triazin-2-yl)-N4,N4-dimethylbenzene-1,4-diamine (200 mg, 0.6 mmol) and THF (10 mL) was added N$_2$H$_4$·H$_2$O(0.5 mL). The reaction was continued stirring at 50° C. for additional 4 hrs. THF was removed and H$_2$O(30 mL) was added. The product was collected by filtration to afford N-(4-hydrazinyl-6-morpholino-1,3,5-triazin-2-yl)-N4,N4-dimethylbenzene-1,4-diamine (190 mg, yield 85%).

Step 6

The procedure for step 6 is similar to that used in step 4 of Example 10.

$^1$H NMR (400 MHz, DMSO-d$_6$): δ=11.40 (brs, 1H), 10.50 (brs, 1H), 8.90 (s, 1H), 8.45-8.45 (m, 1H), 8.31 (s, 1H), 7.91-7.90 (m, 1H), 7.68 (s, 1H), 7.48-7.41 (m, 2H), 7.22-7.11 (m, 2H), 6.73-6.71 (m, 2H), 3.80-3.62 (m, 8H), 2.86-2.82 (m, 6H).

MS: m/z 458.0 (M+H$^+$)

Example 35—(E)-6-(2-((1H-Indol-3-yl)methylene)hydrazinyl)-N2-ethyl-N2-methyl-N4-(p-tolyl)-1,3,5-triazine-2,4-diamine

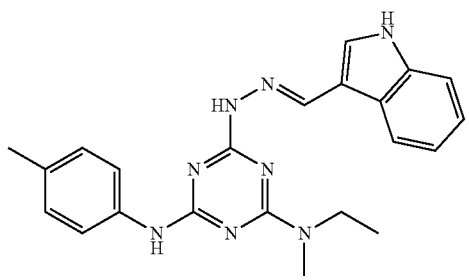 [SMILES: CCN(C)c1nc(N/N=C/c2c[nH]c3ccccc23)nc(Nc2ccc(C)cc2)n1]

The title compound was prepared using methods and procedures similar to those described for Example 13.

$^1$H NMR (400 MHz, DMSO-d6): δ=11.40 (brs, 1H), 10.49 (brs, 1H), 8.98 (brs, 1H), 8.48-8.40 (m, 1H), 8.33 (s, 1H), 8.08-7.67 (m, 3H), 7.42 (d, J=8.4 Hz, 1H), 7.26-7.09 (m, 4H), 3.64-3.65 (m, 2H), 3.10 (s, 3H), 2.28 (s, 3H), 1.17-1.14 (m, 3H).

MS: m/z 401.0 (M+H$^+$).

Example 36—(E)-4-(2-((1H-Indol-3-yl)methylene)hydrazinyl)-6-(azetidin-1-yl)-N-(p-tolyl)-1,3,5-triazin-2-amine

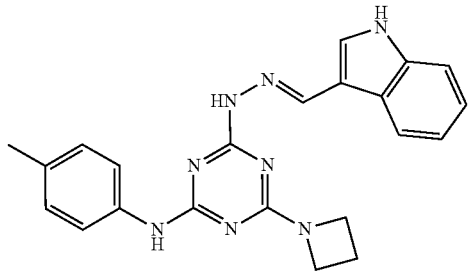 [SMILES: Cc1ccc(Nc2nc(N/N=C/c3c[nH]c4ccccc34)nc(N3CCC3)n2)cc1]

The title compound was prepared using methods and procedures similar to those described for Example 13.

$^1$H NMR (400 MHz, DMSO-d6): δ=11.43 (brs, 1H), 10.75 (brs, 1H), 9.18 (brs, 1H), 8.46 (d, J=8.0 Hz, 1H), 8.30 (d, J=6.4 Hz, 1H), 7.99-7.96 (m, 2H), 7.68 (s, 1H), 7.43 (d, J=6.4 Hz, 1H), 7.25-7.12 (m, 4H), 4.06-4.00 (m, 4H), 2.30-2.29 (m, 5H).

MS: m/z 399.0 (M+H$^+$).

Example 37—(E)-1-(4-(2-((1H-Indol-3-yl)methylene)hydrazinyl)-6-(p-tolylamino)-1,3,5-triazin-2-yl)piperidin-4-ol

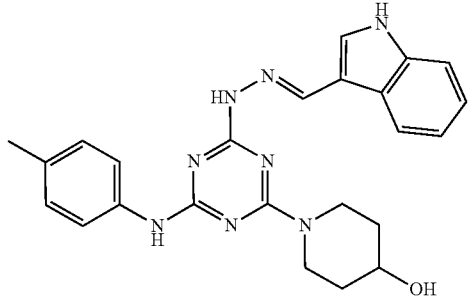 [SMILES: Cc1ccc(Nc2nc(N/N=C/c3c[nH]c4ccccc34)nc(N3CCC(O)CC3)n2)cc1]

The title compound was prepared using methods and procedures similar to those described for Example 13.

$^1$H NMR (400 MHz, DMSO-d6): δ=11.42 (brs, 1H), 10.53 (brs, 1H), 9.05 (brs, 1H), 8.47 (d, J=7.2 Hz, 1H), 8.32 (s, 1H), 8.07-7.68 (m, 3H), 7.43 (d, J=8.4 Hz, 1H), 7.22-7.10 (m, 4H), 4.73 (d, J=4.4 Hz, 1H), 4.33-4.29 (m, 2H), 3.75 (d, J=3.6 Hz, 1H), 3.28-3.27 (m, 2H), 2.28 (s, 3H), 1.80-1.78 (m, 2H), 1.35-1.33 (m, 2H).

MS: m/z 443.0 (M+H$^+$).

Example 38—(E)-4-(2-((1H-Indol-3-yl)methylene)hydrazinyl)-6-thiomorpholino-N-(p-tolyl)-1,3,5-triazin-2-amine

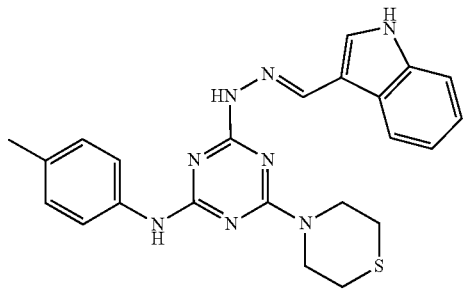 [SMILES: Cc1ccc(Nc2nc(N/N=C/c3c[nH]c4ccccc34)nc(N3CCSCC3)n2)cc1]

The title compound was prepared using methods and procedures similar to those described for Example 13.

$^1$H NMR (400 MHz, DMSO-d6): δ=11.42 (brs, 1H), 10.60 (brs, 1H), 9.13 (brs, 1H), 8.46 (d, J=6.0 Hz, 1H), 8.32 (s, 1H), 8.08-7.60 (m, 3H), 7.43 (d, J=8.0 Hz, 1H), 7.22-7.12 (m, 4H), 4.12-4.08 (m, 4H), 2.64-2.59 (m, 4H), 2.29 (s, 3H). MS: m/z 445.0 (M+H$^+$).

Example 39—{3-[N'-(1H-indol-3-ylmethylene)-hydrazino]-5-morpholin-4-yl-phenyl}-p-tolyl-amine

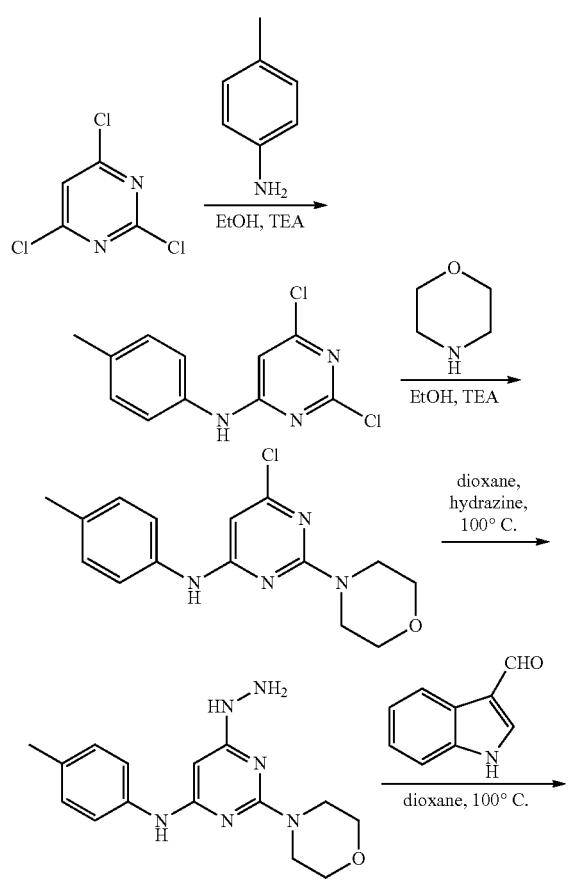

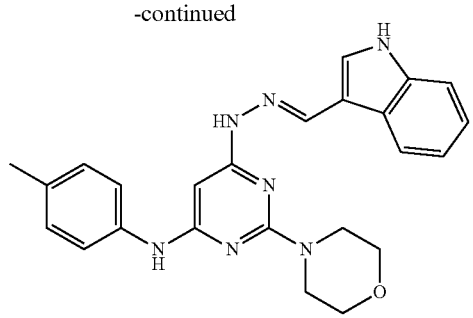

Step 1

To a solution of 2,4,6-trichloro-pyrimidine (1 g, 5.5 mmol) and p-tolylamine (588.5 mg, 5.5 mmol) in EtOH (15 mL) was added TEA (555.5 mg, 5.5 mmol). The reaction was stirred at room temperature overnight. The reaction solution was partitioned between EA (60 mL) and water (60 mL). The organic layer was washed with water (60 mL) and brine (60 mL), dried over Na$_2$SO$_4$ and concentrated in vacuum to give (2,6-dichloro-pyrimidin-4-yl)-p-tolyl-amine (1.4 g, crude) as a white solid. MS: m/z 253.8 (M+H)$^+$.

Step 2

To a solution of (2,6-dichloro-pyrimidin-4-yl)-p-tolyl-amine (1.4 g, 5.5 mmol) and morpholine (478.5 mg, 5.5 mmol) in EtOH (15 mL) was added TEA (555.5 mg, 5.5 mmol). The reaction was stirred at 80° C. for 4 hrs. The reaction solution was partitioned between EA (100 mL) and water (100 mL). The organic layer was washed with water (100 mL) and brine (100 mL), dried over Na$_2$SO$_4$ and concentrated in vacuum. The residue was purified by prep-TLC (PE/EA=15/1) to give (6-chloro-2-morpholin-4-yl-pyrimidin-4-yl)-p-tolyl-amine (900 mg, yield: 54%) as a white solid.

$^1$H NMR (400 MHz, CDCl$_3$): δ=7.17 (s, 4H), 6.50 (brs, 1H), 5.95 (s, 1H), 3.77-3.72 (m, 8H), 2.35 (s, 3H). MS: m/z 304.8 (M+H)$^+$.

Step 3

A solution of (6-chloro-2-morpholin-4-yl-pyrimidin-4-yl)-p-tolyl-amine (250 mg, 0.82 mmol) and hydrazine monohydrate (82 mg, 1.64 mmol) in dioxane (8 mL) was stirred at 80° C. for 4 hrs. The reaction was taken up with water (100 mL) and filtered. The filter cake was dried to give (6-hydrazino-2-morpholin-4-yl-pyrimidin-4-yl)-p-tolyl-amine (240 mg, yield: 97.6%) as a white solid. MS: m/z 300.9 (M+H)$^+$.

Step 4

A solution of {3-[N'-(1H-indol-3-ylmethylene)-hydrazino]-5-morpholin-4-yl-phenyl}-p-tolyl-amine (240 mg, 0.8 mmol) and 1H-indole-3-carbaldehyde (116 mg, 0.8 mmol) in dioxane (10 mL) was stirred at 100° C. for 2 hrs. The reaction was taken up with water (100 mL) and filtered. The filter cake was dried to give {3-[N'-(1H-indol-3-ylmethylene)-hydrazino]-5-morpholin-4-yl-phenyl}-p-tolyl-amine (198 mg, yield: 58%) as a red solid.

$^1$H NMR (400 MHz, DMSO-d6): δ=11.40 (d, J=2.0 Hz, 1H), 10.21 (s, 1H), 8.81 (s, 1H), 8.22-8.19 (m, 2H), 7.66 (d, J=1.6 Hz, 1H), 7.47-7.41 (m, 3H), 7.21 (t, J=7.2 Hz, 1H), 7.19-7.10 (m, 3H), 6.01 (s, 1H), 3.65 (s, 8H), 2.28 (s, 3H). MS: m/z 428.0 (M+H)$^+$.

Example 40—[2-morpholin-4-yl-6-(8H-pyrazolo[3,4-b]indol-1-yl)-pyrimidin-4-yl]-p-tolyl-amine Example 41—{2-[N'-(1H-indol-3-ylmethylene)-hydrazino]-6-morpholin-4-yl-pyrimidin-4-yl}-p-tolyl-amine

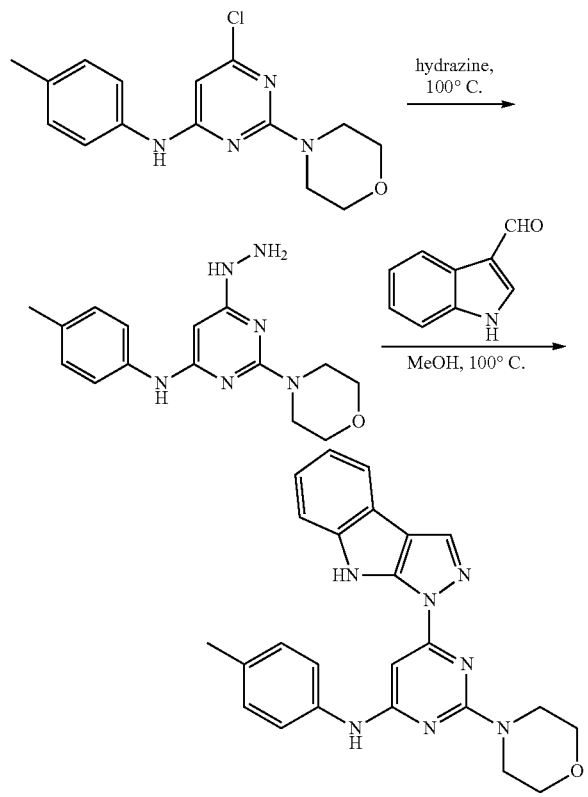

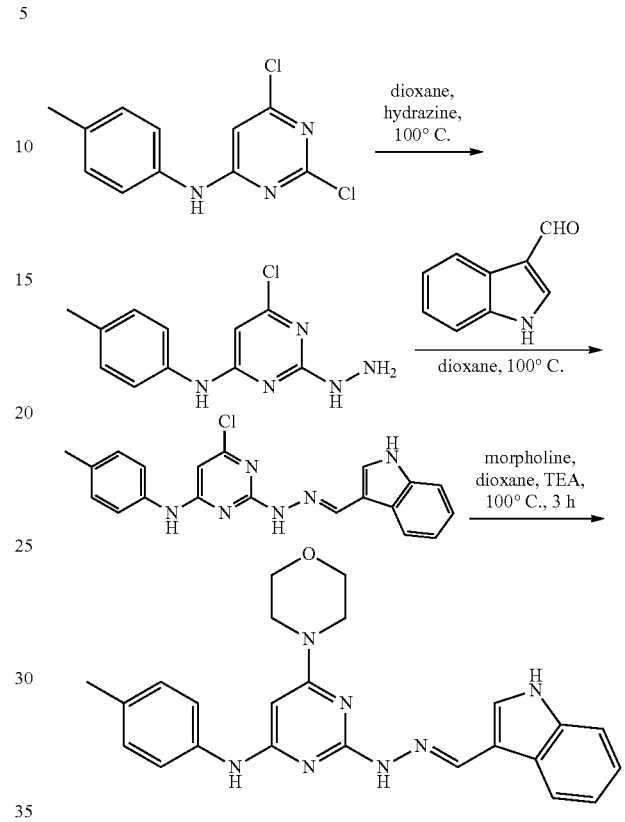

Step 1

A solution of (6-chloro-2-morpholin-4-yl-pyrimidin-4-yl)-p-tolyl-amine (156 mg, crude) in hydrazine monohydrate (5 mL) was stirred at 100° C. overnight. The reaction solution was partitioned between EA (60 mL) and water (60 mL). The organic layer was washed with water (60 mL) and brine (60 mL), dried over $Na_2SO_4$ and concentrated in vacuum to give (6-hydrazino-2-morpholin-4-yl-pyrimidin-4-yl)-p-tolyl-amine (74 mg, crude). MS: m/z 300.9 (M+H)$^+$.

Step 2

A solution of {3-[N'-(1H-indol-3-ylmethylene)-hydrazino]-5-morpholin-4-yl-phenyl}-p-tolyl-amine (74 mg, 0.25 mmol) and 1H-indole-3-carbaldehyde (36 mg, 0.25 mmol) in MeOH (5 mL) was stirred at 78° C. overnight. The reaction solution was partitioned between EA (60 mL) and water (60 mL). The organic layer was washed with water (60 mL) and brine (60 mL), dried over $Na_2SO_4$ and concentrated in vacuum. The residue was purified by prep-HPLC ($NH_3 \cdot H_2O$ as additive) to give [2-morpholin-4-yl-6-(8H-pyrazolo[3,4-b]indol-1-yl)-pyrimidin-4-yl]-p-tolyl-amine (9.6 mg, yield: 4.3%) as a yellow solid.

$^1$H NMR (400 MHz, DMSO-d6): δ=12.86 (s, 1H), 11.54 (s, 1H), 7.77-7.75 (m, 2H), 7.60 (s, 1H), 7.53 (d, J=8.4 Hz, 1H), 7.25-7.21 (m, 3H), 7.13-7.11 (m, 1H), 7.09-7.06 (m, 2H), 3.72-3.67 (m, 8H), 2.33 (s, 3H).

MS: m/z 426.0 (M+H)$^+$.

Step 1

A solution of (2,6-dichloro-pyrimidin-4-yl)-p-tolyl-amine (200 mg, 0.79 mmol) and hydrazine hydrate (39 mL, 0.79 mmol) in dioxane (5 mL) was stirred at 100° C. for 2 hrs. The reaction was triturated with water (100 mL) and filtered. The filter cake was dried to give (6-chloro-2-hydrazino-pyrimidin-4-yl)-p-tolyl-amine (140 mg, crude) as a white solid.

$^1$H NMR (400 MHz, DMSO-d6): δ=9.31 (s, 1H), 8.21 (s, 1H), 7.56 (d, J=8.0 Hz, 2H), 7.10 (d, J=8.4 Hz, 2H), 5.98 (s, 1H), 4.22 (s, 2H), 2.25 (s, 3H). MS: m/z 249.9 (M+H)$^+$.

Step 2

A solution of (6-chloro-2-hydrazino-pyrimidin-4-yl)-p-tolyl-amine (140 mg, 0.56 mmol) and 1H-indole-3-carbaldehyde (81.2 mg, 0.56 mmol) in dioxane (10 mL) was stirred at 100° C. for 3 hrs. The reaction was treated with water (100 mL) and filtered. The filter cake was dried to give {6-chloro-2-[N'-(1H-indol-3-ylmethylene)-hydrazino]-pyrimidin-4-yl}-p-tolyl-amine (164 mg, crude). MS: m/z 376.8 (M+H)$^+$.

Step 3

A solution of {6-chloro-2-[N'-(1H-indol-3-ylmethylene)-hydrazino]-pyrimidin-4-yl}-p-tolyl-amine (164 mg, 0.436 mmol) and morpholine (42 mg, 0.48 mmol) in dioxane (5 mL) was stirred at 100° C. for 3 hrs. The reaction was treated with water (100 mL) and filtered to get the solid. Then the solid was purified by prep-HPLC ($NH_3 \cdot H_2O$ as additive) to give {2-[N'-(1H-indol-3-ylmethylene)-hydrazino]-6-morpholin-4-yl-pyrimidin-4-yl}-p-tolyl-amine (8.8 mg, yield: 4.7%) as a white solid.

¹H NMR (400 MHz, DMSO-d6): δ=11.34 (s, 1H), 10.15 (s, 1H), 8.82 (s, 1H), 8.49 (d, J=8.0 Hz, 1H), 8.27 (s, 1H), 7.82-7.81 (m, 2H), 7.63 (s, 1H), 7.42 (d, J=7.6 Hz, 1H), 7.21 (t, J=7.6 Hz, 1H), 7.12-7.08 (m, 3H), 5.45 (s, 1H), 3.71-3.69 (m, 4H), 3.47 (s, 4H), 2.29 (s, 3H).

MS: m/z 427.8 (M+H)⁺.

Example 42—(2-Chloro-phenyl)-{4-[N'-(1H-indol-3-ylmethylene)-hydrazino]-6-morpholin-4-yl-[1,3,5]triazin-2-yl}-amine

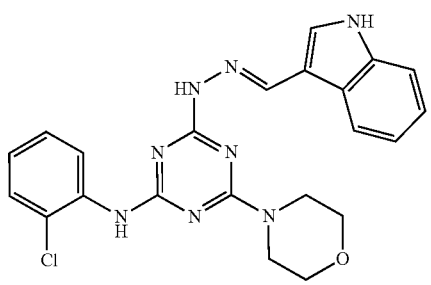 [SMILES: Clc1ccccc1Nc1nc(N/N=C/c2c[nH]c3ccccc23)nc(N2CCOCC2)n1]

The title compound was prepared using methods and procedures similar to those described for Example 10.

¹H NMR (400 MHz, DMSO-d₆): δ=11.40 (brs, 1H), 10.68 (brs, 1H), 8.62-8.21 (m, 3H), 8.15 (s, 1H), 7.68 (d, J=2.4 Hz, 1H), 7.50 (d, J=8.0 Hz, 1H), 7.42-7.32 (m, 2H), 7.18 (t, J=7.2 Hz, 2H), 7.09 (t, J=7.2 Hz, 1H), 4.05-3.56 (m, 8H). MS: m/z 448.9 (M+H⁺)

Example 43—[4-Morpholin-4-yl-6-(N'-pyridin-2-ylmethylene-hydrazino)-[1,3,5]triazin-2-yl]-p-tolyl-amine

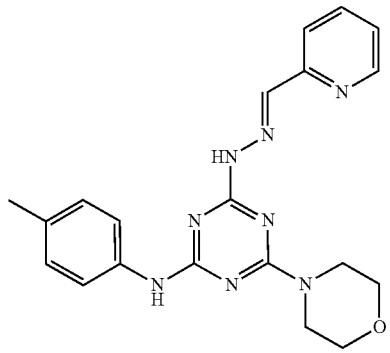 [SMILES: Cc1ccc(Nc2nc(N/N=C/c3ccccn3)nc(N3CCOCC3)n2)cc1]

The title compound was prepared using methods and procedures similar to those described for Example 10.

¹H NMR (400 MHz, DMSO-d6): δ=11.12 (brs, 1H), 9.26 (brs, 1H), 8.56 (d, J=4.4 Hz, 1H), 8.18 (s, 1H). 8.02-7.83 (m, 2H), 7.78-7.54 (m, 2H), 7.36 (d, J=5.4 Hz, 1H), 7.09 (d, J=8.8 Hz, 2H), 3.86-3.58 (m, 8H), 2.25 (s, 3H).

MS: m/z 391.0 (M+H⁺).

Example 44—{4-[N'-(1H-Indol-2-ylmethylene)-hydrazino]-6-morpholin-4-yl-[1,3,5]triazin-2-yl}-p-tolyl-amine

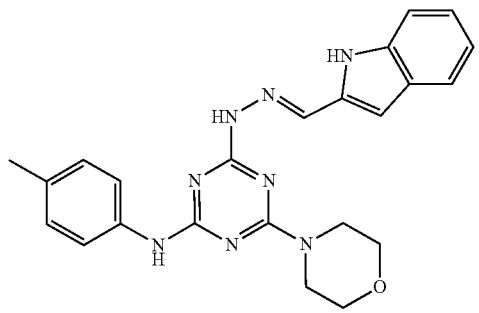 [SMILES: Cc1ccc(Nc2nc(N/N=C/c3cc4ccccc4[nH]3)nc(N3CCOCC3)n2)cc1]

The title compound was prepared using methods and procedures similar to those described for Example 10.

¹H NMR (400 MHz, DMSO-d6): δ=11.22 (s, 1H), 10.85 (s, 1H), 9.12 (s, 1H), 8.21 (s, 1H), 7.64 (d, J=8.4 Hz, 2H), 7.53 (d, J=7.6 Hz, 1H), 7.43 (d, J=8.0 Hz, 1H), 7.16-7.05 (m, 3H), 6.99 (t, J=6.8 Hz, 1H), 6.71 (s, 1H), 3.86-3.62 (m, 8H), 2.25 (s, 3H).

MS: m/z 429.0 (M+H⁺).

Example 45—{4-[N'-(1H-Indol-3-ylmethylene)-hydrazino]-6-morpholin-4-yl-[1,3,5]triazin-2-yl}-(5-methyl-pyridin-2-yl)-amine

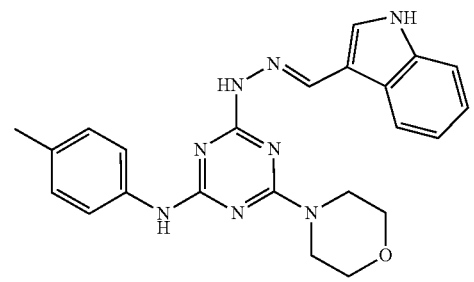 [SMILES: Cc1ccc(Nc2nc(N/N=C/c3c[nH]c4ccccc34)nc(N3CCOCC3)n2)cc1]

The title compound was prepared using methods and procedures similar to those described in Example 10.

¹H NMR (400 MHz, DMSO-d₆): δ=11.45 (brs, 1H), 10.73 (brs, 1H), 9.07 (s, 1H), 8.45 (d, J=8.0 Hz, 1H), 8.33 (s, 1H), 8.12 (s, 1H), 7.71 (s, 1H), 7.59 (d, J=9.2 Hz, 1H), 7.43 (d, J=9.2 Hz, 1H), 7.30-7.04 (s, 2H), 3.85-3.61 (m, 8H), 3.29 (s, 1H), 2.28 (s, 3H).

MS: m/z 430.0 (M+H⁺).

Example 46—(E)-N-(4-((4-(2-((1H-indol-3-yl)methylene)hydrazinyl)-6-morpholino-1,3,5-triazin-2-yl)amino)phenyl)methanesulfonamide

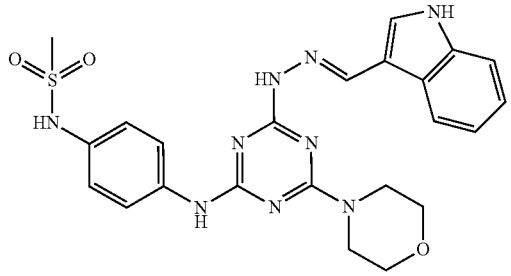 [SMILES: CS(=O)(=O)Nc1ccc(Nc2nc(N/N=C/c3c[nH]c4ccccc34)nc(N3CCOCC3)n2)cc1]

The title compound was prepared using methods and procedures similar to those described in Example 34.

$^1$H NMR (400 MHz, DMSO-d$_6$): δ=11.43 (brs, 1H), 10.62 (brs, 1H), 9.49-9.47 (m, 1H), 9.23 (s, 1H), 8.45-8.42 (m, 1H), 8.33-8.32 (m, 1H), 8.12-8.10 (m, 1H), 7.72-7.68 (m, 2H), 7.44-7.42 (m, 1H), 7.25-7.14 (m, 4H), 3.84-3.62 (m, 8H), 2.91 (s, 3H).

MS: m/z 508.0 (M+H$^+$)

Example 47—(E)-4-(2-((1H-Indol-3-yl)methylene)hydrazinyl)-6-(3,4-dihydroisoquinolin-2(1H)-yl)-N-(p-tolyl)-1,3,5-triazin-2-amine

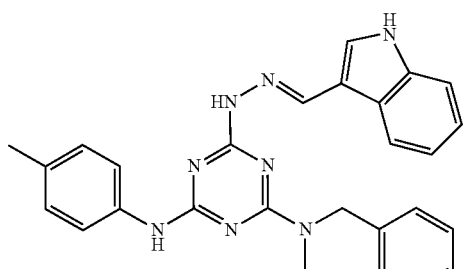

The title compound was prepared using methods and procedures similar to those described in Example 13.

$^1$H NMR (400 MHz, DMSO-d6): δ=11.44 (brs, 1H), 10.71 (brs, 1H), 9.33-9.16 (m, 1H), 8.57-8.45 (m, 1H), 8.34 (s, 1H), 8.00-7.70 (m, 3H), 7.44 (d, J=8.4 Hz, 1H), 7.23-7.10 (m, 8H), 4.92-4.89 (m, 2H), 4.02 (s, 2H), 2.90 (t, J=1.6 Hz, 2H), 2.30 (s, 3H).

MS: m/z 475.0 (M+H$^+$).

Example 48—(E)-4-(2-((1H-Indol-3-yl)methylene)hydrazinyl)-6-(2H-benzo[b][1,4]oxazin-4(3H)-yl)-N-(p-tolyl)-1,3,5-triazin-2-amine

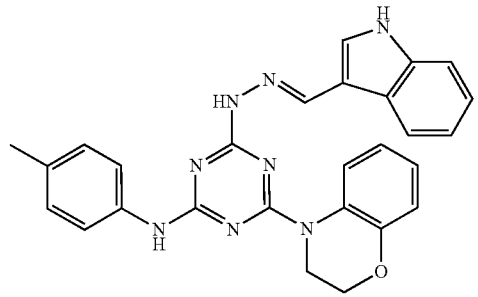 [SMILES: Cc1ccc(Nc2nc(N/N=C/c3c[nH]c4ccccc34)nc(N3CCOc4ccccc43)n2)cc1]

The title compound was prepared using methods and procedures similar to those described in Example 13.

$^1$H NMR (400 MHz, DMSO-d6): δ=11.47 (d, J=2.0 Hz, 1H), 10.80-10.71 (m, 1H), 9.33-9.16 (m, 1H), 8.57-8.38 (m, 2H), 8.19-8.02 (m, 1H), 7.72-7.64 (m, 2H), 7.43 (d, J=6.4 Hz, 1H), 7.24-6.90 (m, 8H), 4.31-4.21 (m, 4H), 2.28 (s, 3H).

MS: m/z 477.0 (M+H$^+$).

Example 49—(E)-4-(2-((1H-Indol-3-yl)methylene)hydrazinyl)-6-(4-methoxypiperidin-1-yl)-N-(p-tolyl)-1,3,5-triazin-2-amine

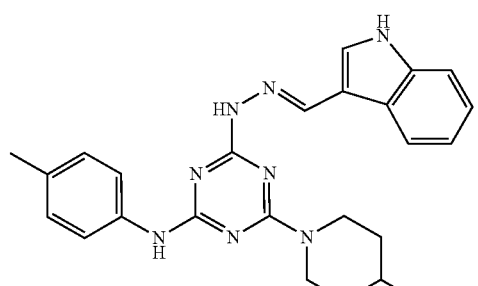

The title compound was prepared using methods and procedures similar to those described in Example 13.

$^1$H NMR (400 MHz, DMSO-d6): δ=11.42 (brs, 1H), 10.47 (brs, 1H), 9.06 (brs, 1H), 8.47 (d, J=7.2 Hz, 1H), 8.32 (s, 1H), 7.95-7.68 (m, 3H), 7.43 (d, J=7.6 Hz, 1H), 7.21-7.10 (m, 4H), 4.22-4.19 (m, 2H), 3.45-3.39 (m, 3H), 3.30 (s, 3H), 2.29 (s, 3H), 1.90-1.88 (m, 2H), 1.42-1.40 (m, 2H).

MS: m/z 457.3 (M+H$^+$).

Example 50—(E)-4-(2-((1H-Indol-3-yl)methylene)hydrazinyl)-6-(3-methylmorpholino)-N-(p-tolyl)-1,3,5-triazin-2-amine

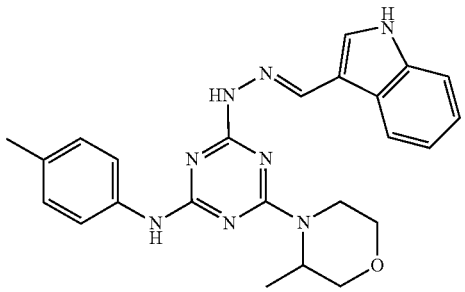 [SMILES: Cc1ccc(Nc2nc(N/N=C/c3c[nH]c4ccccc34)nc(N3CCOCC3C)n2)cc1]

The title compound was prepared using methods and procedures similar to those described in Example 13.

¹H NMR (400 MHz, DMSO-d6): δ=11.41 (brs, 1H), 10.56 (brs, 1H), 9.08 (m, 1H), 8.46 (d, J=7.2 Hz, 1H), 8.33 (s, 1H), 8.07-7.68 (m, 3H), 7.42 (d, J=8.0 Hz, 1H), 7.23-7.12 (m, 4H), 4.69 (s, 1H), 4.32 (s, 1H), 3.93-3.91 (m, 1H), 3.73-3.71 (m, 1H), 3.60-3.57 (m, 1H), 3.46-3.40 (m, 1H), 3.18-3.17 (m, 1H), 2.28 (s, 3H), 1.26-1.25 (m, 3H).

MS: m/z 443.0 (M+H⁺).

Example 51—(E)-6-(2-((1H-Indol-3-yl)methylene)hydrazinyl)-N2-isopropyl-N2-(2-methoxyethyl)-N4-(p-tolyl)-1,3,5-triazine-2,4-diamine

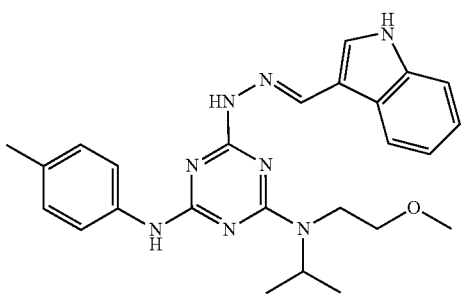 [SMILES: COCCN(c1nc(N/N=C/c2c[nH]c3ccccc23)nc(Nc2ccc(C)cc2)n1)C(C)C]

The title compound was prepared using methods and procedures similar to those described in Example 13.

¹H NMR (400 MHz, DMSO-d6): δ=11.40 (brs, 1H), 10.47 (brs, 1H), 8.99-8.98 (m, 1H), 8.46 (d, J=4.4 Hz, 1H), 8.33 (s, 1H), 7.97-7.67 (m, 3H), 7.42 (d, J=7.6 Hz, 1H), 7.21-7.09 (m, 4H), 4.99-4.98 (m, 1H), 3.71-3.48 (m, 4H), 3.31 (s, 3H), 2.28 (s, 3H), 1.23-1.17 (m, 6H).

MS: m/z 459.1 (M+H⁺).

Example 52—(E)-4-(2-((1H-Indol-3-yl)methylene)hydrazinyl)-6-(3-oxa-8-azabicyclo[3.2.1]octan-8-yl)-N-(p-tolyl)-1,3,5-triazin-2-amine

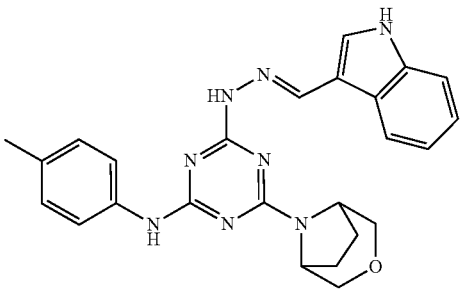 [SMILES: Cc1ccc(Nc2nc(N/N=C/c3c[nH]c4ccccc34)nc(N3C4CCC3COC4)n2)cc1]

The title compound was prepared using methods and procedures similar to those described in Example 13.

¹H NMR (400 MHz, DMSO-d6): δ=11.43 (d, J=2.0 Hz, 1H), 10.64 (brs, 1H), 9.15 (brs, 1H), 8.45 (d, J=6.4 Hz, 1H), 8.32 (s, 1H), 8.10-7.60 (m, 3H), 7.43 (d, J=8.4 Hz, 1H), 7.23-7.13 (m, 4H), 4.60-4.59 (m, 2H), 3.67-3.59 (m, 4H), 2.29 (s, 3H), 1.99-1.92 (m, 4H).

MS: m/z 455.0 (M+H⁺).

Example 53—4-(2-(benzofuran-3-ylmethylene)hydrazinyl)-6-morpholino-N-(p-tolyl)-1,3,5-triazin-2-amine

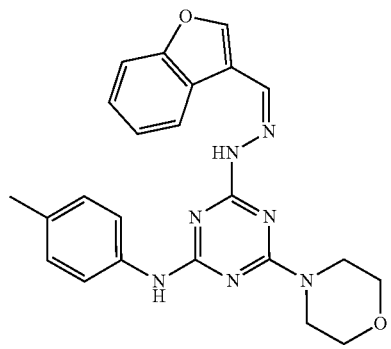 [SMILES: Cc1ccc(Nc2nc(N/N=C\c3coc4ccccc34)nc(N3CCOCC3)n2)cc1]

The title compound was prepared according to the methods and procedures similar to those described herein for Example 10.

¹H NMR (400 MHz, DMSO-d6): δ=11.07 (s, 1H), 9.44 (m, 1H), 8.16 (s, 1H), 7.70-7.57 (m, 4H), 7.37 (t, J=8.4 Hz, 1H), 7.28 (t, J=7.6 Hz, 1H), 7.19 (s, 1H), 7.09 (d, J=8.4 Hz, 2H), 3.80-3.60 (m, 8H), 2.25 (s, 3H).

MS: m/z 430.2 (M+H⁺).

Example 54—N2-(2-(1H-indol-3-yl)ethyl)-6-morpholino-N4-(p-tolyl)-1,3,5-triazine-2,4-diamine

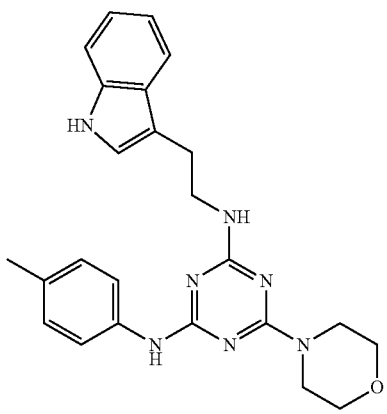 [SMILES: Cc1ccc(Nc2nc(NCCc3c[nH]c4ccccc34)nc(N3CCOCC3)n2)cc1]

The title compound was prepared according to the methods and procedures similar to those described herein for Example 1.

$^1$H NMR (400 MHz, DMSO-d6): δ=10.82 (d, J=8.0 Hz, 1H), 8.86 (s, 1H), 7.65-7.57 (m, 2H), 7.54 (t, J=8.0 Hz, 1H), 7.33 (d, J=8.0 Hz, 1H), 7.16 (s, 1H), 7.10-6.91 (m, 5H), 3.75-3.46 (m, 10H), 2.93 (t, J=8.0 Hz, 2H), 2.22 (s, 3H).

MS: m/z 430.0 (M+H$^+$).

Example 55—(E)-4-(2-((1H-indol-3-yl)methylene)hydrazinyl)-6-morpholino-N-(naphthalen-1-yl)-1,3,5-triazin-2-amine

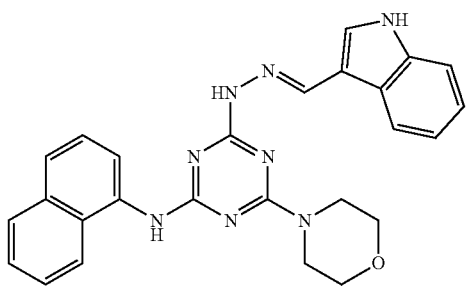 [SMILES: C(=N\Nc1nc(Nc2cccc3ccccc23)nc(N2CCOCC2)n1)/c1c[nH]c2ccccc12]

The title compound was prepare according to the methods an procedures similar to those described herein for Examples 1-52.

Example 56—(E)-4-(azepan-1-yl)-6-(2-((2-methyl-1H-indol-3-yl)methylene)hydrazinyl)-N-(4-nitrophenyl)-1,3,5-triazin-2-amine

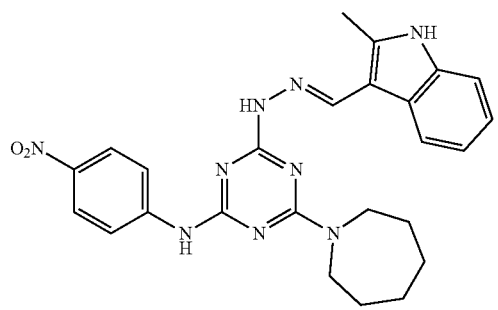 [SMILES: Cc1[nH]c2ccccc2c1/C=N/Nc1nc(Nc2ccc([N+](=O)[O-])cc2)nc(N2CCCCCC2)n1]

The title compound was prepared according to the methods and procedures similar to those described herein for Examples 1-52.

Example A—U251 Vacuolization Assay Data (24h) for Compounds of Examples 8-56

TABLE 8

| Ex No. | Structure | EC$_{50}$ (µM) |
|---|---|---|
| 8 | 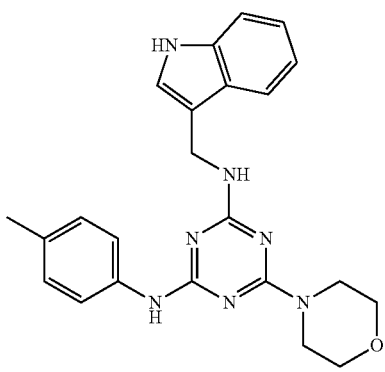 [SMILES: Cc1ccc(Nc2nc(NCc3c[nH]c4ccccc34)nc(N3CCOCC3)n2)cc1] | ++ |

TABLE 8-continued
| Ex No. | Structure | EC$_{50}$ (μM) |
|---|---|---|
| 9 | 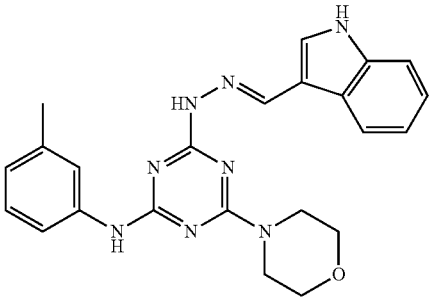 [SMILES: Cc1cccc(Nc2nc(N/N=C/c3c[nH]c4ccccc34)nc(N3CCOCC3)n2)c1] | + |
| 10 | 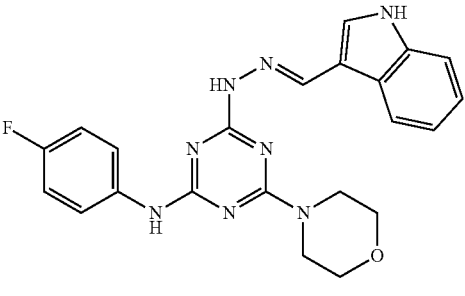 [SMILES: Fc1ccc(Nc2nc(N/N=C/c3c[nH]c4ccccc34)nc(N3CCOCC3)n2)cc1] | + |
| 11 | 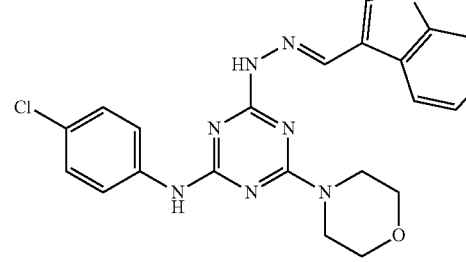 | + |
| 12 | 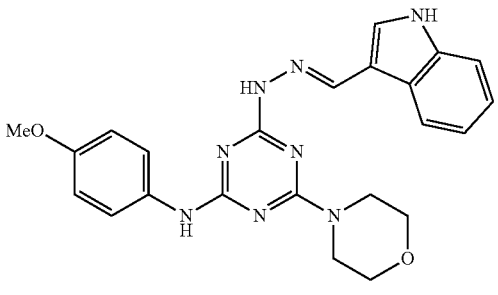 [SMILES: COc1ccc(Nc2nc(N/N=C/c3c[nH]c4ccccc34)nc(N3CCOCC3)n2)cc1] | + |
| 13 | 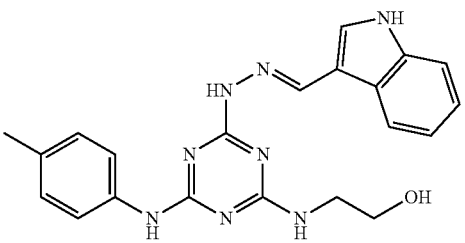 [SMILES: Cc1ccc(Nc2nc(NCCO)nc(N/N=C/c3c[nH]c4ccccc34)n2)cc1] | ++++ |

TABLE 8-continued
| Ex No. | Structure | EC$_{50}$ (μM) |
|---|---|---|
| 14 | 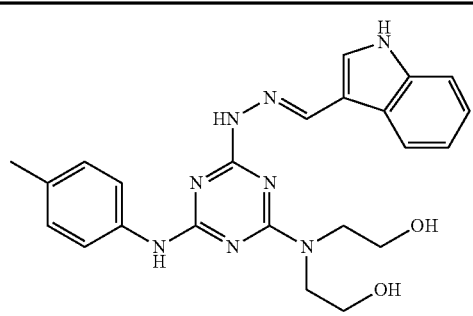 | ++++ |
| 15 | 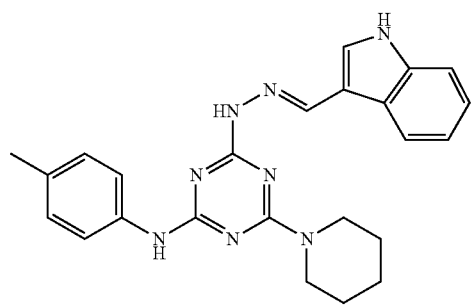 [SMILES: Cc1ccc(Nc2nc(N/N=C/c3c[nH]c4ccccc34)nc(N3CCCCC3)n2)cc1] | ++++ |
| 16 | 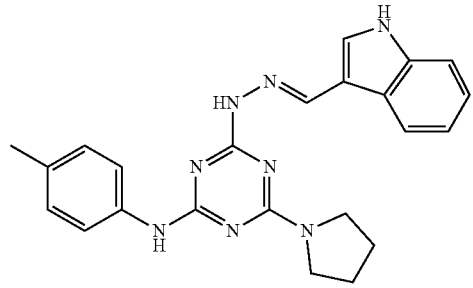 [SMILES: Cc1ccc(Nc2nc(N/N=C/c3c[nH]c4ccccc34)nc(N3CCCC3)n2)cc1] | ++++ |
| 17 | 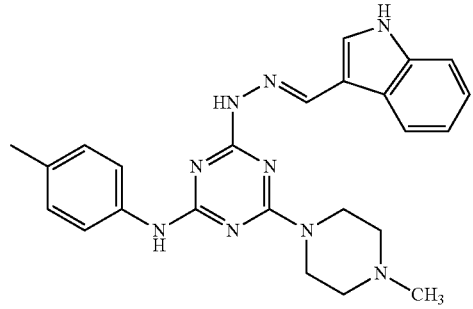 | ++++ |
| 18 | 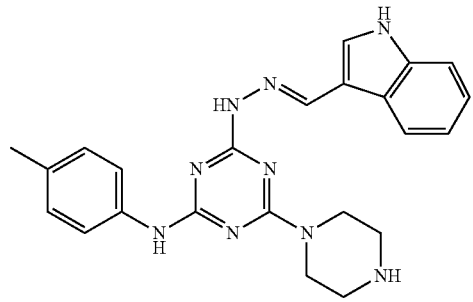 [SMILES: Cc1ccc(Nc2nc(N/N=C/c3c[nH]c4ccccc34)nc(N3CCNCC3)n2)cc1] | ++++ |

TABLE 8-continued

| Ex No. | Structure | EC$_{50}$ (μM) |
|---|---|---|
| 19 | 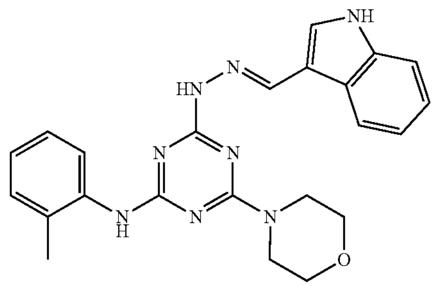 [SMILES: Cc1ccccc1Nc1nc(N/N=C/c2c[nH]c3ccccc23)nc(N2CCOCC2)n1] | + |
| 20 | 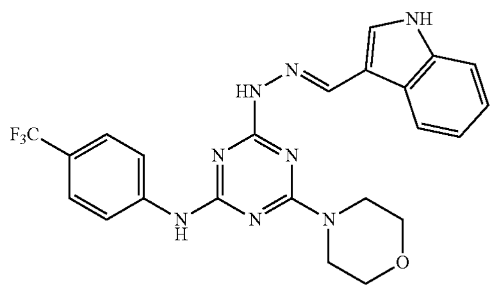 [SMILES: FC(F)(F)c1ccc(Nc2nc(N/N=C/c3c[nH]c4ccccc34)nc(N3CCOCC3)n2)cc1] | + |
| 21 | 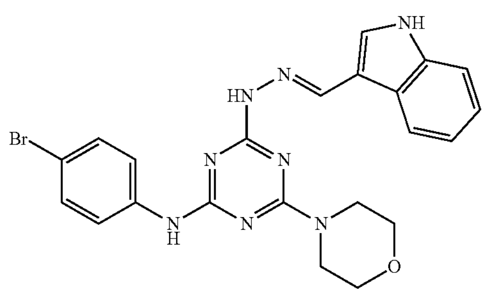 [SMILES: Brc1ccc(Nc2nc(N/N=C/c3c[nH]c4ccccc34)nc(N3CCOCC3)n2)cc1] | + |
| 22 | 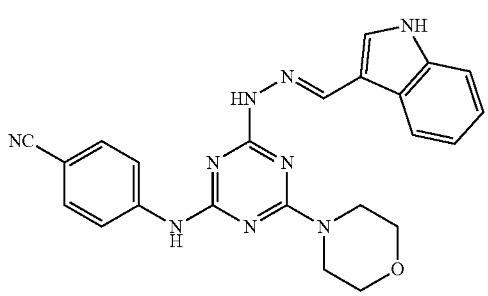 [SMILES: N#Cc1ccc(Nc2nc(N/N=C/c3c[nH]c4ccccc34)nc(N3CCOCC3)n2)cc1] | + |
| 23 | 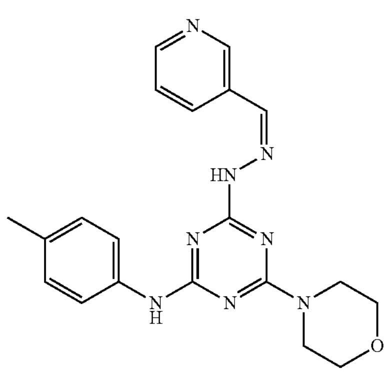 [SMILES: Cc1ccc(Nc2nc(N/N=C\c3cccnc3)nc(N3CCOCC3)n2)cc1] | ++ |

TABLE 8-continued

| Ex No. | Structure | EC$_{50}$ (μM) |
| --- | --- | --- |
| 24 | 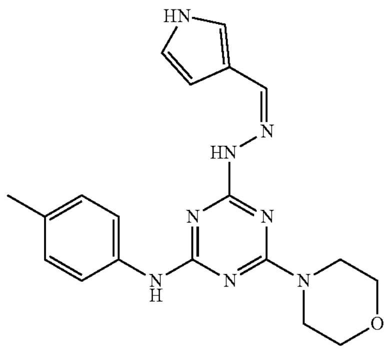 [SMILES: Cc1ccc(Nc2nc(N/N=C\c3cc[nH]c3)nc(N3CCOCC3)n2)cc1] | +++ |
| 25 | 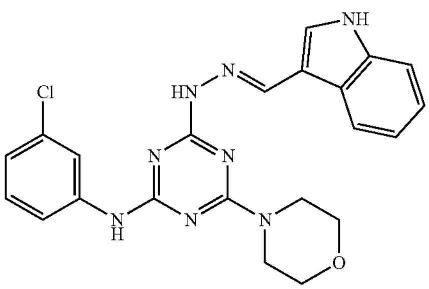 [SMILES: Clc1cccc(Nc2nc(N/N=C/c3c[nH]c4ccccc34)nc(N3CCOCC3)n2)c1] | + |
| 26 | 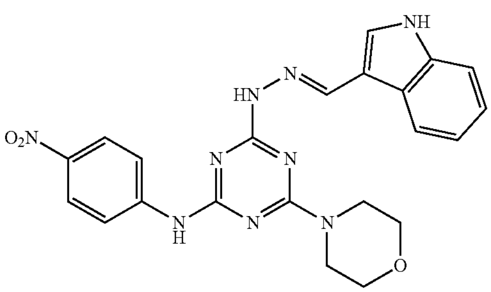 | + |
| 27 | 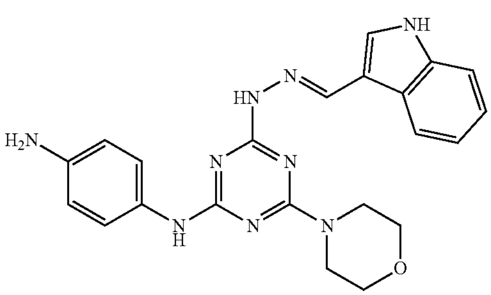 [SMILES: O=[N+]([O-])c1ccc(Nc2nc(N/N=C/c3c[nH]c4ccccc34)nc(N3CCOCC3)n2)cc1] | + |
| 28 | 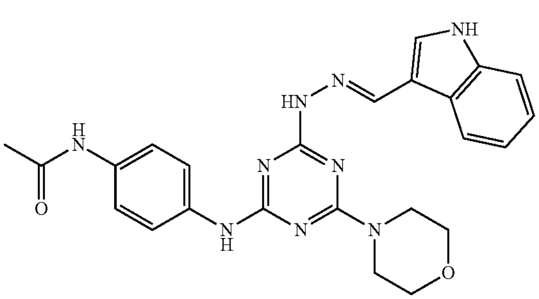 [SMILES: CC(=O)Nc1ccc(Nc2nc(N/N=C/c3c[nH]c4ccccc34)nc(N3CCOCC3)n2)cc1] | + |

TABLE 8-continued

| Ex No. | Structure | EC$_{50}$ (µM) |
|---|---|---|
| 29 | 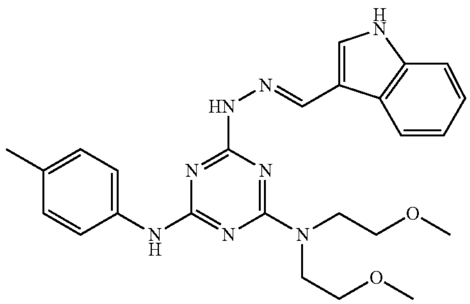 [SMILES: COCCN(CCOC)c1nc(N/N=C/c2c[nH]c3ccccc23)nc(Nc2ccc(C)cc2)n1] | ++++ |
| 30 | 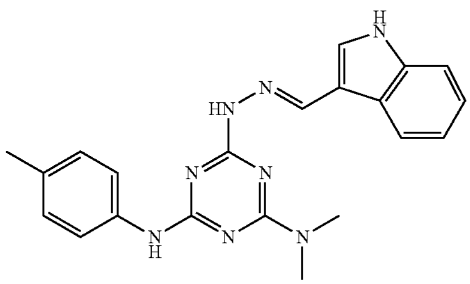 [SMILES: Cc1ccc(Nc2nc(N/N=C/c3c[nH]c4ccccc34)nc(N(C)C)n2)cc1] | ++++ |
| 31 | 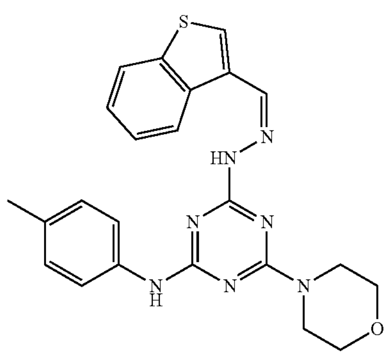 [SMILES: Cc1ccc(Nc2nc(N/N=C\c3csc4ccccc34)nc(N3CCOCC3)n2)cc1] | ++ |
| 32 | 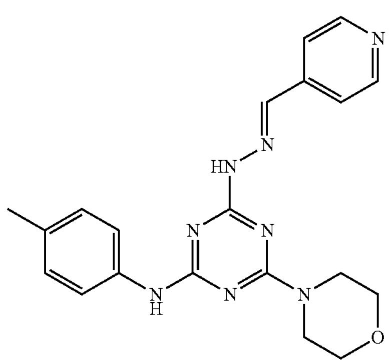 [SMILES: Cc1ccc(Nc2nc(N/N=C/c3ccncc3)nc(N3CCOCC3)n2)cc1] | ++ |

TABLE 8-continued

| Ex No. | Structure | EC$_{50}$ (μM) |
|---|---|---|
| 33 | 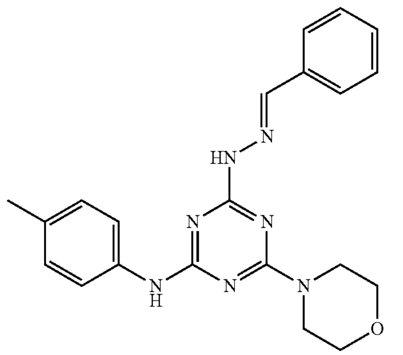 [SMILES: Cc1ccc(Nc2nc(N/N=C/c3ccccc3)nc(N3CCOCC3)n2)cc1] | + |
| 34 | 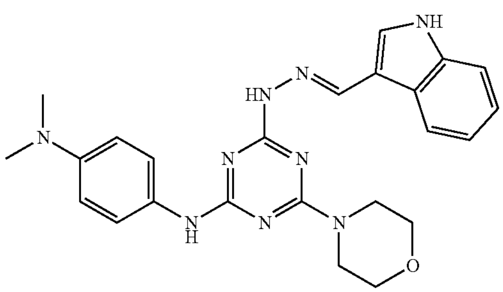 [SMILES: CN(C)c1ccc(Nc2nc(N/N=C/c3c[nH]c4ccccc34)nc(N3CCOCC3)n2)cc1] | + |
| 35 | 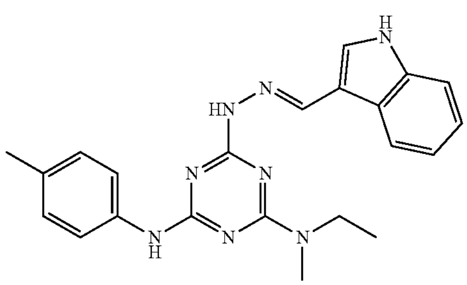 [SMILES: CCN(C)c1nc(N/N=C/c2c[nH]c3ccccc23)nc(Nc2ccc(C)cc2)n1] | ++++ |
| 36 | 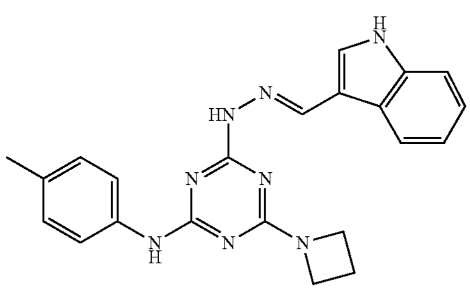 [SMILES: Cc1ccc(Nc2nc(N/N=C/c3c[nH]c4ccccc34)nc(N3CCC3)n2)cc1] | ++++ |
| 37 | 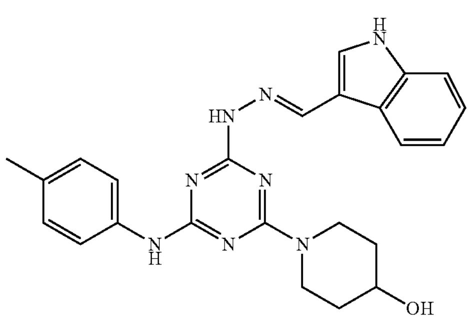 [SMILES: Cc1ccc(Nc2nc(N/N=C/c3c[nH]c4ccccc34)nc(N3CCC(O)CC3)n2)cc1] | ++++ |

TABLE 8-continued

| Ex No. | Structure | EC$_{50}$ (μM) |
| --- | --- | --- |
| 38 | 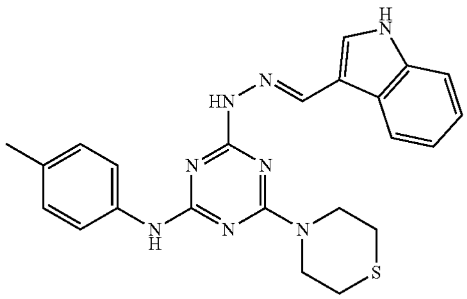 [SMILES: Cc1ccc(Nc2nc(N/N=C/c3c[nH]c4ccccc34)nc(N3CCSCC3)n2)cc1] | ++++ |
| 39 | 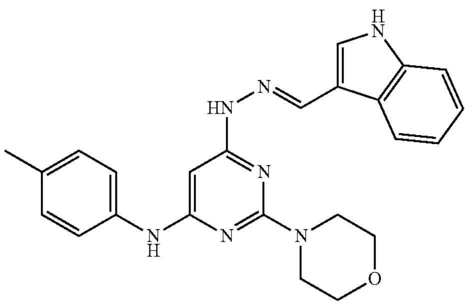 [SMILES: Cc1ccc(Nc2cc(N/N=C/c3c[nH]c4ccccc34)nc(N3CCOCC3)n2)cc1] | ++ |
| 40 | 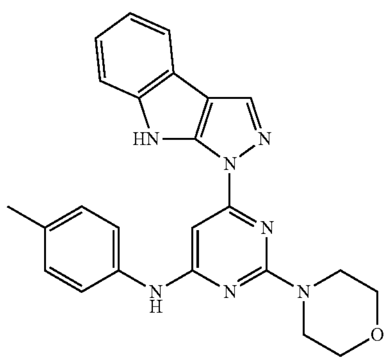 [SMILES: Cc1ccc(Nc2cc(-n3ncc4c5ccccc5[nH]c43)nc(N3CCOCC3)n2)cc1] | +++ |
| 41 | 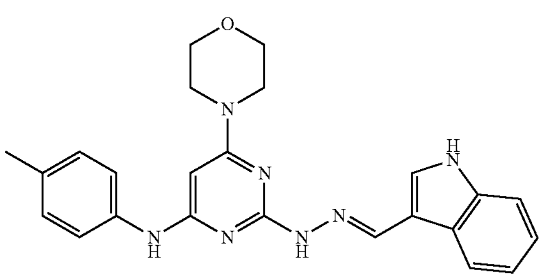 [SMILES: Cc1ccc(Nc2cc(N3CCOCC3)nc(N/N=C/c3c[nH]c4ccccc34)n2)cc1] | ++ |
| 42 | 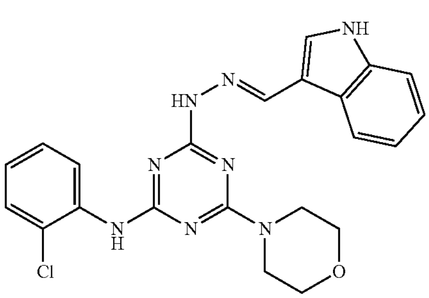 [SMILES: Clc1ccccc1Nc1nc(N/N=C/c2c[nH]c3ccccc23)nc(N2CCOCC2)n1] | + |

TABLE 8-continued

| Ex No. | Structure | EC$_{50}$ (μM) |
|---|---|---|
| 43 | 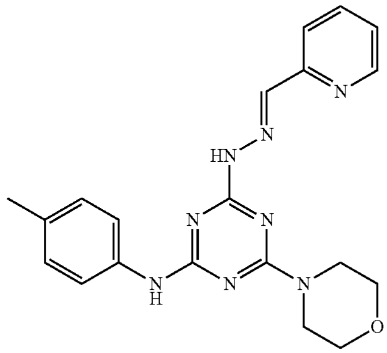 | ++ |
| 44 | 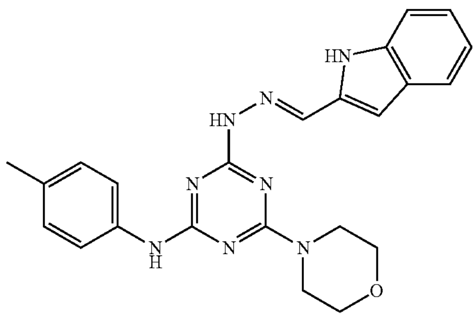 [SMILES: Cc1ccc(Nc2nc(N/N=C/c3cc4ccccc4[nH]3)nc(N3CCOCC3)n2)cc1] | ++ |
| 45 | 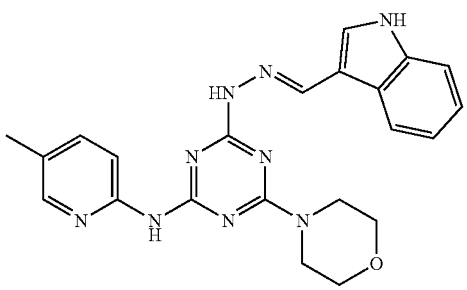 [SMILES: Cc1ccc(Nc2nc(N/N=C/c3c[nH]c4ccccc34)nc(N3CCOCC3)n2)nc1] | + |
| 46 | 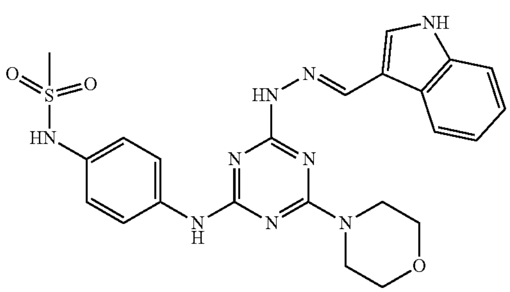 [SMILES: CS(=O)(=O)Nc1ccc(Nc2nc(N/N=C/c3c[nH]c4ccccc34)nc(N3CCOCC3)n2)cc1] | + |
| 47 | 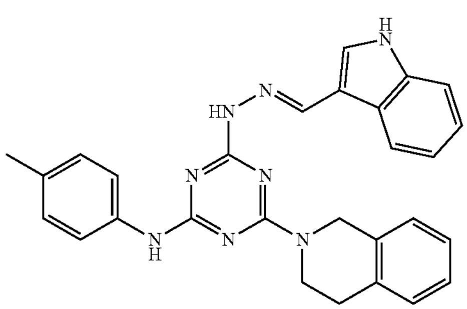 [SMILES: Cc1ccc(Nc2nc(N/N=C/c3c[nH]c4ccccc34)nc(N3CCc4ccccc4C3)n2)cc1] | + |

TABLE 8-continued

| Ex No. | Structure | EC$_{50}$ (μM) |
|---|---|---|
| 48 | 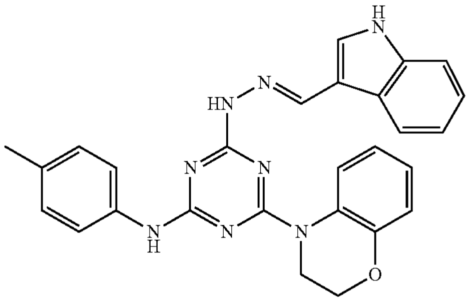 [SMILES: Cc1ccc(Nc2nc(N/N=C/c3c[nH]c4ccccc34)nc(N3CCOc4ccccc43)n2)cc1] | ++++ |
| 49 | 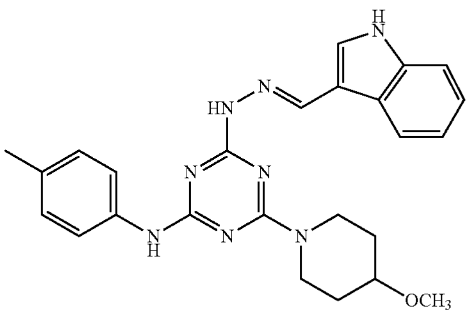 [SMILES: COC1CCN(c2nc(N/N=C/c3c[nH]c4ccccc34)nc(Nc3ccc(C)cc3)n2)CC1] | ++++ |
| 50 | 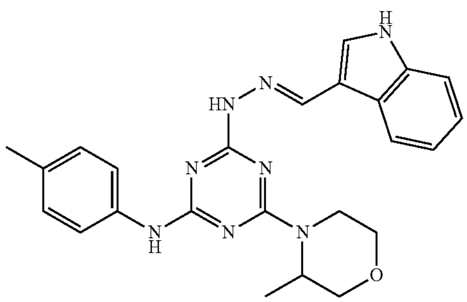 [SMILES: Cc1ccc(Nc2nc(N/N=C/c3c[nH]c4ccccc34)nc(N3CCOCC3C)n2)cc1] | + |
| 51 | 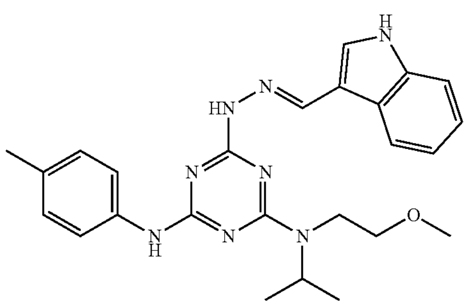 [SMILES: COCCN(c1nc(N/N=C/c2c[nH]c3ccccc23)nc(Nc2ccc(C)cc2)n1)C(C)C] | ++ |
| 52 | 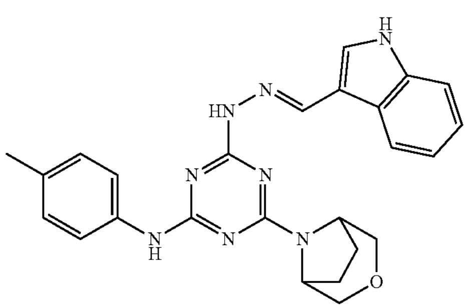 [SMILES: Cc1ccc(Nc2nc(N/N=C/c3c[nH]c4ccccc34)nc(N3C4CCC3COC4)n2)cc1] | ++ |

TABLE 8-continued
| Ex No. | Structure | EC$_{50}$ (μM) |
|---|---|---|
| 53 | 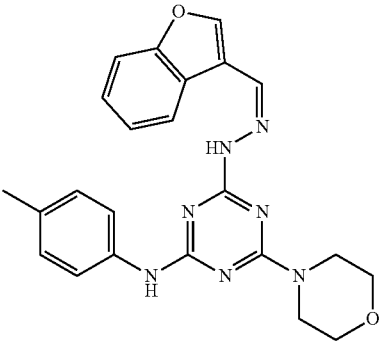 | ++++ |
| 54 | 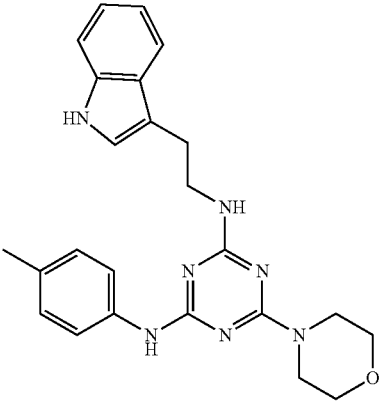 [SMILES: Cc1ccc(Nc2nc(NCCc3c[nH]c4ccccc34)nc(N3CCOCC3)n2)cc1] | ++++ |
| 55 | 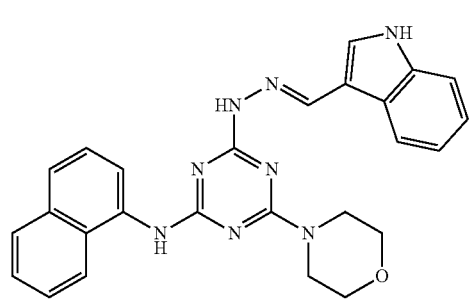 [SMILES: C(=N\Nc1nc(Nc2cccc3ccccc23)nc(N2CCOCC2)n1)/c1c[nH]c2ccccc12] | + |
| 56 | 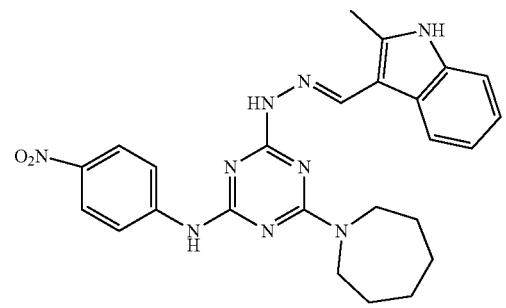 [SMILES: Cc1[nH]c2ccccc2c1/C=N/Nc1nc(Nc2ccc([N+](=O)[O-])cc2)nc(N2CCCCCC2)n1] | ++++ |
+ EC$_{50}$ is ≤ 1 μM.
++ EC$_{50}$ is 1 < 10 μM
+++ EC$_{50}$ is 10 ≤ 50 μM
++++ EC$_{50}$ is > 50 μM Other Embodiments It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A compound selected from:

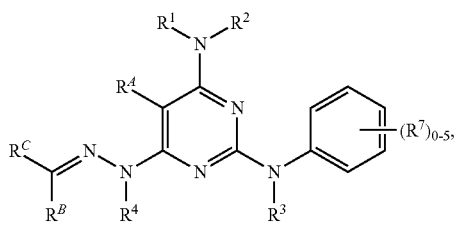

or a pharmaceutically acceptable salt thereof, wherein:
$R^1$ is selected from H and $C_{1-6}$ alkyl optionally substituted with $OR^{a2}$;
$R^2$ is $C_{1-6}$ alkyl optionally substituted with $OR^{a2}$; or
$R^1$ and $R^2$ together form a 4-7 membered heterocycloalkyl, which is optionally substituted with 1, 2, or 3 substituents independently selected $R^8$;
each $R^8$ is selected from $C_{1-6}$ alkyl and $OR^{a2}$;
$R^{a2}$ is selected from H and $C_{1-6}$ alkyl;
$R^3$ is selected from H, $C_{1-6}$ alkyl, and $C_{1-6}$ haloalkyl;
$R^4$ is selected from H, $C_{1-6}$ alkyl, and $C_{1-6}$ haloalkyl;
each $R^7$ is selected from halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;
$R^{a1}$, $R^{c1}$, and $R^{d1}$ are each independently selected from H, $C_{1-6}$ alkyl, and $C_{1-4}$ haloalkyl;
each $R^{b1}$ is independently selected from $C_{1-6}$ alkyl and $C_{1-4}$ haloalkyl;
$R^A$ is selected from H, $C_{1-6}$ alkyl, and $C_{1-6}$ haloalkyl;
$R^B$ is selected from H, $C_{1-6}$ alkyl, and $C_{1-6}$ haloalkyl;
$R^C$ is selected from $C_{6-10}$ aryl, 5-membered heteroaryl, and 7-10 membered heteroaryl, each of which is optionally substituted with 1, 2, or 3 substituents independently selected from halo, CN, $NO_2$, $C_{1-6}$ alkyl, $C_{1-6}$ haloalkyl, $OR^{a3}$, $NR^{c3}R^{d3}$ $NR^{c3}C(O)R^{b3}$, and $NR^{c3}S(O)_2R^{b3}$;
$R^{a3}$, $R^{c3}$, and $R^{d3}$ are each independently selected from H, $C_{1-6}$ alkyl, and $C_{1-4}$ haloalkyl; and
each $R^{b3}$ is independently selected from $C_{1-6}$ alkyl and $C_{1-4}$ haloalkyl.

2. The compound of claim 1, wherein:
$R^1$ and $R^2$ together with N to which they are attached form a ring selected from morpholinyl, thiomorpholinyl, piperidinyl, pyrrolidinyl, piperazinyl, azetidinyl, and 3-oxa-8-azabicyclo[3.2.1]octanyl, each of which is optionally substituted with 1, 2, or 3 independently selected $R^8$;
$R^3$ and $R^4$ are each H;
$R^7$ is selected from halo, CN, $NO_2$, $C_{1-6}$ alkyl, $C_{1-6}$ haloalkyl, $OR^{a1}$, $NR^{c1}R^{d1}$ $NR^{c1}C(O)R^{b1}$, and $NR^{c1}S(O)_2R^{b1}$;
$R^A$ is H;
$R^B$ is H; and
$R^C$ is selected from phenyl, indolyl, pyrrolyl, benzofuranyl, and thiophenyl, each of which is optionally substituted with 1 or 2 substituents independently selected from methyl, trifluoromethyl, methoxy, fluoro, chloro, bromo, CN, $NO_2$, amino, dimethylamino, NHC(O)$CH_3$, and $NHS(O)_2CH_3$.

3. The compound of claim 1, wherein:
$R^1$ is selected from H and $C_{1-6}$ alkyl optionally substituted with $OR^{a2}$;
$R^2$ is $C_{1-6}$ alkyl optionally substituted with $OR^{a2}$; $R^3$ and $R^4$ are each H;
each $R^7$ is independently selected from halo, CN, $NO_2$, $C_{1-6}$ alkyl, $C_{1-6}$ haloalkyl, $OR^{a1}$, $NR^{c1}R^{d1}$, $NR^{c1}C(O)R^{b1}$, and $NR^{c1}S(O)_2R^{b1}$; $R^A$ is H;
$R^B$ is H; and
$R^C$ is selected from phenyl, indolyl, pyrrolyl, benzofuranyl, and thiophenyl, each of which is optionally substituted with 1 or 2 substituents independently selected from methyl, trifluoromethyl, methoxy, fluoro, chloro, bromo, CN, $NO_2$, amino, dimethylamino, NHC(O)$CH_3$, and $NHS(O)_2CH_3$.

4. The compound of claim 1, wherein:
$R^1$ and $R^2$ together with N to which they are attached form a ring selected from morpholinyl, thiomorpholinyl, piperidinyl, pyrrolidinyl, piperazinyl, azetidinyl, and 3-oxa-8-azabicyclo[3.2.1]octanyl, each of which is optionally substituted with 1, 2, or 3 independently selected $R^8$;
$R^3$ and $R^4$ are each H;
each $R^7$ is selected from halo, CN, $NO_2$, $C_{1-6}$ alkyl, $C_{1-6}$ haloalkyl, $OR^{a1}$, $NR^{c1}R^{d1}$, $NR^{c1}C(O)R^{b1}$, and $NR^{c1}S(O)_2R^{b1}$;
$R^A$ is H;
$R^B$ is H; and
$R^C$ is selected from phenyl, indolyl, pyrrolyl, benzofuranyl, and thiophenyl, each of which is optionally substituted with 1 or 2 substituents independently selected from methyl, trifluoromethyl, methoxy, fluoro, chloro, bromo, CN, $NO_2$, amino, dimethylamino, NHC(O)$CH_3$, and $NHS(O)_2CH_3$.

5. The compound of claim 1, wherein the compound is:

| Ex No. | Structure |
|---|---|
| 3 | 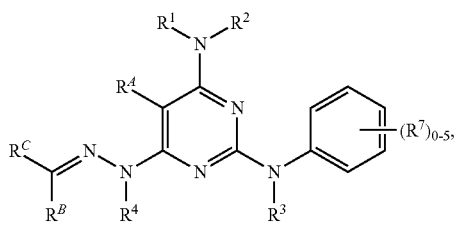 | or a pharmaceutically acceptable salt thereof.

6. A pharmaceutical composition comprising a compound of claim 1, or a pharmaceutically acceptable salt thereof, and a pharmaceutically acceptable carrier.

7. A method of:
inhibiting phosphatidylinositol-3-phosphate 5-kinase type III (PIKfyve) in a glioblastoma, malignant peripheral nerve sheath tumor (MPNST) or colorectal cancer cell; and/or inducing cytoplasmic vacuolization in a glioblastoma, malignant peripheral nerve sheath tumor (MPNST) or colorectal cancer cell; and/or blocking secretion of IL12/23 in a cell; and/or inhibiting phosphatidylinositol-3-phosphate 5-kinase type III (PIKfyve) in a subject; and/or inducing cytoplasmic vacuolization in a glioblastoma, malignant peripheral nerve sheath tumor (MPNST) or colorectal cancer cell of a subject; and/or treating a cancer in a subject; and/or treating an inflammatory disease or condition in a subject;

the method comprising contacting the cell with an effective amount of, or administering to a subject in need thereof a therapeutically effective amount of, a compound of claim 1, or a pharmaceutically acceptable salt thereof.

8. The compound of claim 1, wherein $R^B$ is H; and $R^C$ is selected from indolyl, pyrrolyl, and benzofuranyl, each of which is optionally substituted with 1, 2, or 3 substituents independently selected from halo, CN, $NO_2$, $C_{1-6}$ alkyl, $C_{1-6}$ haloalkyl, $OR^{a3}$, $NR^{c3}R^{d3}$, and $NR^{c3}C(O)R^{b3}$.

9. The compound of claim 1, wherein $R^B$ is H; and $R^C$ is indolyl.

10. The compound of claim 1, wherein $R^B$ is H; and $R^C$ is selected from indolyl, pyrrolyl, and benzofuranyl, each of which is optionally substituted with 1, 2, or 3 substituents independently selected from halo, CN, $NO_2$, $C_{1-6}$ alkyl, $C_{1-6}$ haloalkyl, $OR^{a3}$, $NR^{c3}R^{d3}$, and $NR^{c3}C(O)R^{b3}$.

11. The compound of claim 8, wherein $R^B$ is H; and $R^C$ is selected from indolyl, pyrrolyl, and benzofuranyl, each of which is optionally substituted with 1, 2, or 3 substituents independently selected from halo, CN, $NO_2$, $C_{1-6}$ alkyl, $C_{1-6}$ haloalkyl, and $OR^{a3}$.

12. The compound of claim 11, wherein $R^B$ is H; and $R^C$ is selected from indolyl, and pyrrolyl, each of which is optionally substituted with 1, 2, or 3 substituents independently selected from halo, CN, $C_{1-6}$ alkyl, and $C_{1-6}$ haloalkyl.

13. The compound of claim 12, wherein $R^B$ is H; and $R^C$ is selected from indolyl, and pyrrolyl, each of which is optionally substituted with 1, 2, or 3 substituents independently selected from halo, and $C_{1-6}$ alkyl.

14. The compound of claim 13, wherein $R^B$ is H; and $R^C$ is indolyl optionally substituted with 1, 2, or 3 substituents independently selected from halo, and $C_{1-3}$ alkyl.

15. A pharmaceutical composition comprising the compound of claim 8, or a pharmaceutically acceptable salt thereof, and a pharmaceutically acceptable carrier.

16. A pharmaceutical composition comprising a compound of claim 11, or a pharmaceutically acceptable salt thereof, and a pharmaceutically acceptable carrier.

17. A pharmaceutical composition comprising a compound of claim 12, or a pharmaceutically acceptable salt thereof, and a pharmaceutically acceptable carrier.

18. A pharmaceutical composition comprising a compound of claim 13, or a pharmaceutically acceptable salt thereof, and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 12,030,896 B2 | Page 1 of 1 |
| APPLICATION NO. | : 17/255810 | |
| DATED | : July 9, 2024 | |
| INVENTOR(S) | : Richard J. Bram, Eduard Serguienko and Anthony B. Pinkerton | |

It is certified that error appears in the above-identified patent and that said Letters Patent is hereby corrected as shown below:

In the Claims

In Column 95, Line 49, In Claim 1, delete "$NR^{c3}R^{d3}$" and insert -- $NR^{c3}R^{d3}$, --.

In Column 95, Line 64, In Claim 2, delete "$NR^{c1}R^{d1}$" and insert -- $NR^{c1}R^{d1}$. --.

Signed and Sealed this
Seventh Day of October, 2025

John A. Squires
*Director of the United States Patent and Trademark Office*